(12) United States Patent
Moore et al.

(10) Patent No.: US 11,596,525 B2
(45) Date of Patent: Mar. 7, 2023

(54) IMPLANTS AND INSTRUMENTS WITH FLEXIBLE FEATURES

(71) Applicant: K2M, Inc., Leesburg, VA (US)

(72) Inventors: Jennifer Anne Moore, Leesburg, VA (US); Todd M. Wallenstein, Ashburn, VA (US); Clint Boyd, Leesburg, VA (US); Jordan Floyd, Westlake, OH (US); Patrick Ayerle, Severna Park, MD (US)

(73) Assignee: K2M, Inc., Leesburg, VA (US)

( * ) Notice: Subject to any disclaimer, the term of this patent is extended or adjusted under 35 U.S.C. 154(b) by 53 days.

(21) Appl. No.: 16/961,512

(22) PCT Filed: Jan. 11, 2019

(86) PCT No.: PCT/US2019/013260
§ 371 (c)(1),
(2) Date: Jul. 10, 2020

(87) PCT Pub. No.: WO2019/140240
PCT Pub. Date: Jul. 18, 2019

(65) Prior Publication Data
US 2020/0337856 A1    Oct. 29, 2020

Related U.S. Application Data

(60) Provisional application No. 62/616,078, filed on Jan. 11, 2018, provisional application No. 62/616,071, (Continued)

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/30985* (2013.01)

(58) Field of Classification Search
CPC combination set(s) only.
See application file for complete search history.

(56) References Cited

U.S. PATENT DOCUMENTS 4,863,538 A    9/1989  Deckard
4,944,817 A    7/1990  Bourell et al.
(Continued)

OTHER PUBLICATIONS

Papp, Donald, "Hackday: 3D Printing Flexible Surfaces out of Non-Flexible Material", Retrieved from the Internet <https://hackaday.com/2017/08/05/3d-printing-flexible-surfaces-out-of-non-flexible-material/, Aug. 5, 2017, 10 pages.
(Continued)

*Primary Examiner* — Jan Christopher L Merene
(74) *Attorney, Agent, or Firm* — Lerner, David, Littenberg, Krumholz & Mentlik, LLP

(57) ABSTRACT

According to one embodiment of the disclosure, an implant includes a body having a surface with a flexible pattern defined by a plurality of material segments including a first material segment and a second material segment. The first material segment abuts the second material segment. Further, the first material segment includes a first non-linear shape extending between a first end and a second end while the second material segment includes a second non-linear shape extending between a first end and a second end. The two material segments are interconnected such that one of the first end and the second end of the first non-linear shape is interconnected with one of the first end and the second end of the second non-linear shape.

16 Claims, 35 Drawing Sheets

Related U.S. Application Data filed on Jan. 11, 2018, provisional application No. 62/616,073, filed on Jan. 11, 2018, provisional application No. 62/616,062, filed on Jan. 11, 2018, provisional application No. 62/616,076, filed on Jan. 11, 2018.

(56) References Cited

U.S. PATENT DOCUMENTS

| | | |
|---|---|---|
| 5,017,753 A | 5/1991 | Deckard |
| 5,076,869 A | 12/1991 | Bourell et al. |
| 5,609,635 A | 3/1997 | Michelson |
| 6,136,031 A * | 10/2000 | Middleton ............... A61F 2/442 623/17.16 |
| 7,537,664 B2 | 5/2009 | O'Neill et al. |
| 8,034,080 B2 * | 10/2011 | Malandain ......... A61B 17/7065 606/279 |
| 8,303,663 B2 | 11/2012 | Jimenez et al. |
| 8,636,746 B2 | 1/2014 | Jimenez et al. |
| 8,771,360 B2 | 7/2014 | Jimenez et al. |
| 8,932,302 B2 | 1/2015 | Jimenez et al. |
| 9,358,125 B2 | 6/2016 | Jimenez et al. |
| 9,474,626 B2 | 10/2016 | Jimenez et al. |
| 9,498,270 B2 | 11/2016 | Jimenez et al. |
| 2002/0161443 A1 | 10/2002 | Michelson |
| 2003/0040802 A1 * | 2/2003 | Errico ..................... A61F 2/442 623/17.14 |
| 2004/0010318 A1 * | 1/2004 | Ferree ..................... A61F 2/442 623/17.11 |
| 2007/0260324 A1 | 11/2007 | Joshi et al. |
| 2012/0191189 A1 * | 7/2012 | Huang .................. A61F 2/4425 623/17.11 |
| 2013/0096685 A1 | 4/2013 | Ciupik et al. |
| 2016/0296342 A1 * | 10/2016 | Woods ............... A61B 17/8625 |
| 2016/0377113 A1 | 12/2016 | Jimenez et al. |
| 2019/0105172 A1 | 4/2019 | Sournac et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2020/0038198 A1 | 2/2020 | Miccio |

OTHER PUBLICATIONS

International Search Report and Written Opinion for PCT/US2019/013260, dated Apr. 15, 2019.

* cited by examiner

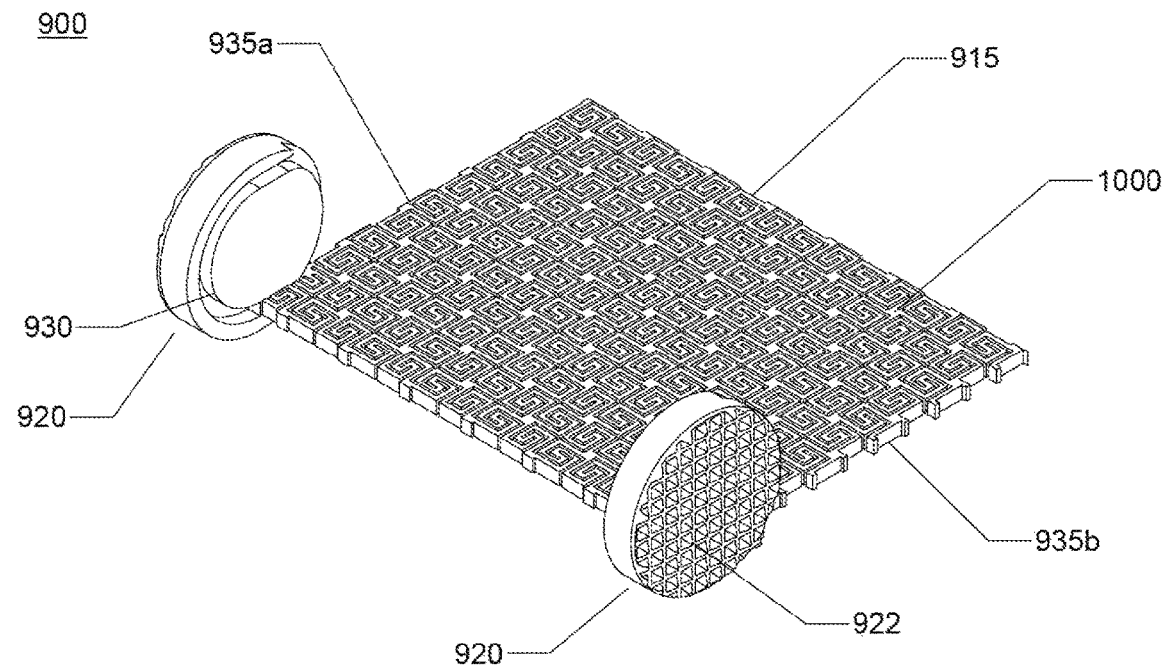
*FIG. 22A*
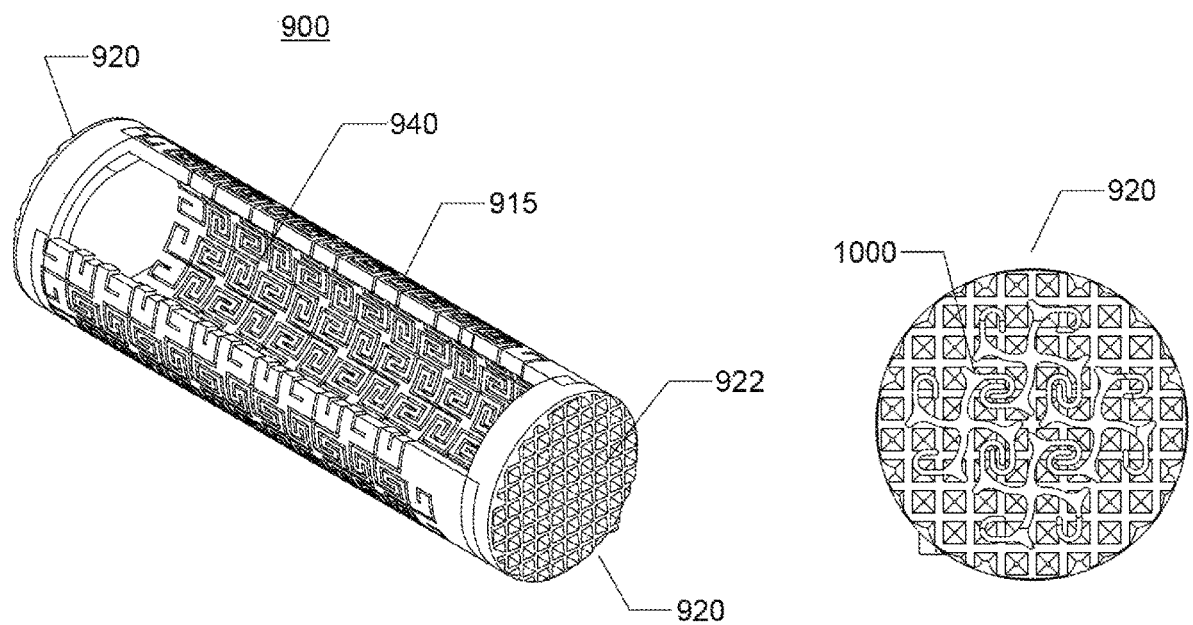
*FIG. 22B*  *FIG. 22C*

IMPLANTS AND INSTRUMENTS WITH FLEXIBLE FEATURES

CROSS-REFERENCE TO RELATED APPLICATIONS

This application is a national phase entry under 35 U.S.C. § 371 of International Application No. PCT/US2019/013260, filed Jan. 11, 2019, which claims the benefit of U.S. Provisional Patent Application Nos. 62/616,062 filed Jan. 11, 2018, 62/616,071 filed Jan. 11, 2018, 62/616,073 filed Jan. 11, 2018, 62/616,076 filed Jan. 11, 2018, and 62/616,078 filed Jan. 11, 2018, the disclosures of which are incorporated by reference herein in their entirety.

FIELD OF THE INVENTION

The invention relates generally to implants and instruments comprising at least one surface with a flexible pattern, wherein the flexible pattern includes a continuous line of material.

BACKGROUND OF THE INVENTION

Various implants and instruments are used in spinal surgery. Many of these include rigid surfaces that may be an impediment to optimal use of such implants and instruments. Specific non-limiting illustrations of challenges associated with use of these elements are outlined below.

Flexible Interbody

After a partial or complete discectomy in which a damaged intervertebral disc is removed, a normally occupied space between adjacent vertebral bodies is subject to collapse and/or misalignment due to the absence of all or a part of the intervertebral disc. In such situations, a physician may insert one or more prosthetic interbodies between the affected vertebrae to maintain normal disc spacing and/or the normal amount of lordosis in the affected region. The normally occupied disc space is not a consistent size between vertebrae. Additionally, the disc space is different in different patients. For this reason, prosthetic interbodies are made of varying size and dimensions so that a physician can select an interbody that most closely matches the disc space.

However, current prosthetic interbodies include rigid surfaces that do not mimic the curvatures of the adjacent vertebral bodies. For this reason, gaps are present between the vertebral body and the prosthetic interbody that may take an extended period of time before bone growth has occurred. There exists a possibility that prosthetic interbodies may be dislodged or moved from their desired implantation location due to movement by the patient before sufficient bone growth has occurred.

Therefore, a need exists for prosthetic interbody that provides a desired amount of lordosis, allows for bone growth between adjacent vertebrae, maintains the space between adjacent vertebrae during bone ingrowth, and resists dislocation from its implantation site.

Fixation Member

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed posteriorly, it is common practice to place bone screws into the vertebral bodies and then connect a metal rod between the screws, thus creating a rigid structure between adjacent vertebral bodies. In some cases, the use of these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body. Because different patients have different anatomies, there exists the potential that a screw may need to be implanted in a different direction than the final trajectory of the screw. For example, most procedures are done through very small incisions. Access into the vertebral body may be at a different angle than the angle at which the surgeon wants the screw to be inserted. For example, if a screwdriver is inserted at an orientation perpendicular to the table/patient, the screw may need to be inserted into the vertebral body at a 45° angle to the patient. The small incision makes it difficult for the surgeon to angle the screwdriver to 45° without increasing the size of the incision.

Additionally, the anatomy of the patient may interfere with a surgeon's ability to insert a screw. For example, when trying to insert a caudally oriented screw into the neck at a high cervical level, i.e., C1-C3, the patient's chin may prevent the surgeon from being able to angle the screwdriver to match the desired insertion angle of the screw.

Therefore, a continuing need exists for an improved fixation member that could reduce the time and labor required by a user to insert the fixation member, such as a screw, into a vertebra, while also protecting the spinal nerves and preventing redirection.

Flexible Instrument

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In a spine fusion, at least two vertebral bodies are rigidly connected using screws implanted into the respective vertebral bodies with a solid metal rod spanning the distance between the screws. The insertion of pedicle or facet screws is relatively straightforward and can be accomplished through a minimal incision. The difficulty arises upon the introduction of a length of rod into a very small incision with extremely limited access and visibility. The minimal incision should be maintained in an open and accessible condition (i.e. as wide as practicable) for introduction of the rod.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

What is needed is a device that works with current instruments to provide the necessary, and possibly limited, retraction needed in a spinal procedure with an ease of use and without impairing a view of the surgical field.

Flexible Rod

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed posteriorly, it is common practice to place bone screws into the vertebral bodies and then connect a metal rod between the screws, thus creating a rigid structure between adjacent vertebral bodies. In some cases, the use of these devices may be permanently implanted in the patient. In other cases, the devices may be implanted only as a temporary means of stabilizing or fixing the bones or bone fragments, with subsequent removal when no longer needed.

The process of properly inserting a rod into the receiving slot of a bone anchor and then securing that connecting rod in place can often require that the surgeon use a number of instruments and expend a great deal of time and effort. When bone anchors in several adjacent vertebrae are to be securely connected by a spinal rod, the repeated process of inserting the rod into the heads of the bone anchors and then securing the rod in place for each respective bone anchor can be difficult, tiresome and time consuming. Further, the alignment of the rod as it connects to each of the sequential bone anchors may require adjustment during the procedure and, therefore it is necessary that the rod can be reduced into the head of each of the sequentially aligned bone anchors and, as necessary, easily adjusted so as to facilitate the process for the surgeon with minimal effort and loss of time.

Additionally, there are sometimes clinical issues that arise in an area between an instrumented level with a non-flexible rod and a non-instrumented level. In particular, this area may experience higher stresses that may lead to future damage of the anatomy.

Corpectomy

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Corpectomy involves removal of the vertebral body as well as the adjacent intervertebral discs.

One of the challenges during surgery is to rebuild a prosthetic vertebral implant, in real time, that matches the curvature of the spine and the dimensions of the vertebral body.

Therefore, a need exists for devices to be used in spinal surgeries that provide a user, such as a surgeon, with the ability to quickly and accurately design a corpectomy device with a curvature and dimensions that are approximate to the discarded vertebral body.

BRIEF SUMMARY OF THE INVENTION

In one aspect, there is disclosed an interbody including at least one surface including a flexible pattern, wherein the flexible pattern includes a continuous line of material.

In some examples, the interbody has at least two surfaces each having an independent flexible pattern. In other examples, the interbody has up to six surfaces each having an independent flexible pattern. In still further examples, the interbody is symmetric. In others, it is asymmetric. In some examples, the flexible pattern includes a plurality of segments that interconnect to form rows and columns. In some examples, each segment of the plurality of segments has a first end and a second end. The first end of each segment may interconnect with at least one second end of another segment of the plurality of segments. In some examples, a first end of each segment interconnects with three different segments. In variants of these examples, a second end of each segment may interconnect with three different segments. In some examples, the interbody has at least one non-flexible surface. In some examples, the interbody may have at least one smooth surface. In yet another example, the at least one flexible surface includes a smooth surface. In some examples, the interbody has at least one surface with a plurality of projections and grooves.

In one aspect, there is disclosed a fixation member comprising a head and at least one surface including a flexible pattern. The flexible pattern may include a continuous line of material.

In some examples, the flexible pattern includes a plurality of segments that interconnect to form rows and columns. In other examples, each segment of the plurality of segments has a first end and a second end. The first end of each segment may interconnect with at least one second end of another segment of the plurality of segments. A first end of each segment may interconnect with three different segments. Further, a second end of each segment may interconnect with three different segments. In some examples, a distal end may include a non-flexible surface. In other examples, a body of the fixation member may include an exterior helical thread. In still further examples, the head may include an exterior helical thread. In some examples, the head may include a keyed inner surface. In some examples, the flexible pattern extends at least quarter of a length of the fixation member. The flexible pattern may extend at least half of a length of the fixation member.

In another aspect, there is disclosed a method for inserting a fixation member performed by inserting the fixation member into an insertion hole and applying a force to a head of the fixation member.

In one aspect, there is disclosed a flexible instrument including an arm and an elongated portion including at least one surface with a flexible pattern having a continuous line of material.

In some examples, the elongated portion is configured and dimensioned to retract tissue. The flexible pattern may include a plurality of segments that interconnect to form rows and columns. In some examples, each segment of the plurality of segments has a first end and a second end. The first end of each segment may interconnect with at least one second end of another segment of the plurality of segments. A first end of each segment may interconnect with three different segments. A second end of each segment may interconnect with three different segments. In some examples, the flexible instrument also includes at least one non-flexible surface.

In one aspect, there is disclosed a rod comprising a first end, a second end, and a body with a flexible pattern having a continuous line of material.

In some examples, the flexible pattern includes a plurality of segments that interconnect to form rows and columns. In other examples, each segment of the plurality of segments has a first end and a second end. The first end of each segment may interconnect with at least one second end of another segment of the plurality of segments. A first end of each segment may interconnect with three different segments. And, a second end of each segment may interconnect with three different segments. In some examples, the flexible pattern extends at least quarter of a length of the rod. The flexible pattern may extend at least a half of a length of the rod. In some examples, the body includes a surface with a flexible pattern and a non-flexible surface.

In one aspect, there is disclosed an adjustable cage device that includes at least one surface with a flexible pattern having a continuous line of material.

In some examples, the cage includes at least one endplate. The at least one endplate may include a flexible pattern. Alternatively or additionally, the endplate may include a channel configured and dimensioned to receive the at least one surface. In some examples, the cage includes an opening. A bone support matrix may be included within the opening. In some examples, the cage includes a housing. In other examples, the cage includes a support member. In further examples, the cage includes a top surface. Any one of the housing, support member or top surface may include the flexible pattern.

In one aspect, the present disclosure relates to a flexible pattern defined by a plurality of segments including a first segment and a second segment. The first segment includes a first non-linear shape that extends between a first end and a second end and the second segment includes a second non-linear shape that extends between a first end and a second end. In this structure, one of the first end and the second end of the first non-linear shape is interconnected with one of the first end and the second end of the second non-linear shape.

In some examples, the flexible surface may be included in an implant. In some examples, the implant may be a fixation member. Where the implant is a fixation member, the fixation member may include an exterior helical thread. The fixation member may include a head with a keyed inner surface. The flexible pattern may extend at least half of a length of the fixation member. In further examples, the implant may be a rod. In some examples, the implant may be an adjustable cage device. The adjustable cage device may include an endplate. In some of these examples, the endplate may include a flexible pattern. In other examples, the endplate may include a channel configured and dimensioned to receive the flexible surface. In some examples where the implant is an adjustable cage device, the adjustable cage device may include a housing that has a flexible pattern. In others, the adjustable cage device may include a support member that includes a flexible pattern. In still others, the adjustable cage device may include a top surface that includes a flexible pattern. In some examples, the implant may be an interbody adapted for placement in a mammalian spine. In other examples, the flexible surface may be included in an instrument. The instrument may be a blade and the blade may be configured and dimensioned to retract tissue.

In some examples, the plurality of segments may include a third segment that abuts the first segment such that a first axis through a center of the first and second segments is orthogonal to a second axis through a center of the first and third segments. In other examples, the plurality of segments may interconnect to form rows and columns. In some examples, the plurality of segments may include a continuous line of material. In some examples, the first non-linear shape may be the same as the second non-linear shape. In further examples, the flexible surface may also include a second flexible surface with a second flexible pattern different from the first flexible pattern. In some examples, the first segment may include two bends between the first end and the second end. In some examples, the flexible surface may include at least two surfaces with the first flexible pattern on the first surface and a second flexible pattern on a second surface. In some examples, the flexible surface may include six surfaces each having a flexible pattern. In some examples, the first end of the first segment may interconnect with three other segments. In some examples, the second end of the first segment may interconnect with three other segments.

In some examples, the flexible surface may be included in a body of one of an implant and an instrument. In some examples, the body has at least one non-flexible surface. In further examples, the body may have at least one smooth surface. In some examples, the body may have at least one surface with a plurality of projections and a plurality of grooves. In other examples, the plurality of segments may be bordered by cut outs in the body that extend through the body. In some examples, the plurality of segments may be bordered by cut outs in the body that extend through less than an entirety of the body. In still further examples, the plurality of segments may be bordered by cut outs in the body and at least two cut outs are oriented at different angles relative to the flexible surface.

In another aspect, the present disclosure relates to a flexible surface that includes a flexible pattern defined by a plurality of material cut outs in the flexible surface. The material cut outs include at least a first material cut out with a first material cut out line having a first end and a second end. The plurality of material cut outs are located adjacent to one another such that the plurality of material cut outs, combined with one another, form rows and columns over the flexible surface.

In some examples, the flexible surface may be included in an implant. In some examples, the implant may be a fixation member. Where the implant is a fixation member, the fixation member may include an exterior helical thread. The fixation member may include a head with a keyed inner surface. The flexible pattern may extend at least half of a length of the fixation member. In further examples, the implant may be a rod. In some examples, the implant may be an adjustable cage device. The adjustable cage device may include an endplate. In some of these examples, the endplate may include a flexible pattern. In other examples, the endplate may include a channel configured and dimensioned to receive the flexible surface. In some examples where the implant is an adjustable cage device, the adjustable cage device may include a housing that has a flexible pattern. In others, the adjustable cage device may include a support member that includes a flexible pattern. In still others, the adjustable cage device may include a top surface that includes a flexible pattern. In some examples, the implant may be an interbody adapted for placement in a mammalian spine. In other examples, the flexible surface may be included in an instrument. The instrument may be a blade and the blade may be configured and dimensioned to retract tissue.

In some examples, the plurality of material cut outs may be positioned so that an axis through the first material cut out line passes through a second cut out line on a second material cut out and a third cut out line on a third material cut out, the second and the third material cut outs being immediately adjacent to the first material cut out. In some variations of this example, the first material cut out may include a first transverse cut out line with the same shape as the first material cut out line, the first transverse cut out line crossing a center of the first material cut out line and oriented at ninety degrees relative to the first material cut out line. In other examples, the flexible surface may include a second flexible surface with a second flexible pattern different from the first flexible pattern. In some examples, the flexible surface may include at least two surfaces with the first flexible pattern on the first surface and a second flexible pattern on a second surface. In some examples, the flexible surface may include six surfaces each having a flexible pattern.

In some examples, the flexible surface may be included in a body of one of an implant and an instrument. In some examples, the body has at least one non-flexible surface. In further examples, the body may have at least one smooth surface. In some examples, the body may have at least one surface with a plurality of projections and a plurality of grooves. In other examples, the material cut outs may extend through the body. In further examples, the material cut outs extend through less than an entirety of the body. In some example, the plurality of material cut outs may include at least two cut outs that are oriented at different angles relative to the flexible surface.

In one aspect, the present disclosure relates to a flexible surface with a flexible pattern defined by a plurality of slits. The plurality of slits are grouped into separate pairs including a first pair and a second pair. The first pair of slits includes a first slit and a second slit, the first slit crossing the second slit. The second pair of slits is adjacent to the first pair of slits and has the same shape as the first pair of slits. The plurality of slits define rows and columns.

In some examples, the flexible surface may be included in an implant. In some examples, the implant may be a fixation member. Where the implant is a fixation member, the fixation member may include an exterior helical thread. The fixation member may include a head with a keyed inner surface. The flexible pattern may extend at least half of a length of the fixation member. In further examples, the implant may be a rod. In some examples, the implant may be an adjustable cage device. The adjustable cage device may include an endplate. In some of these examples, the endplate may include a flexible pattern. In other examples, the endplate may include a channel configured and dimensioned to receive the flexible surface. In some examples where the implant is an adjustable cage device, the adjustable cage device may include a housing that has a flexible pattern. In others, the adjustable cage device may include a support member that includes a flexible pattern. In still others, the adjustable cage device may include a top surface that includes a flexible pattern. In some examples, the implant may be an interbody adapted for placement in a mammalian spine. In other examples, the flexible surface may be included in an instrument. The instrument may be a blade and the blade may be configured and dimensioned to retract tissue.

In some examples, the flexible slits may also include a first curved portion, a central portion and a second curved portion such that the second curved portion is separated from the first curved portion by the central portion. In these examples, each of the first and second curved portions may have a hooked shape. A first axis may extend along a portion of a length of the central portion. The first curved portion may be on a first side of the first axis and the second curved portion may be on a second side of the first axis. A second axis transverse to the first axis may extend through a center of the central portion such that the first curved portion is on a first side of the second axis and the second curved portion is on a second side of the second axis.

In some examples, the first slit may cross the second slit at approximately a midway point on a length of each of the first and second slits. In some examples, the flexible surface may include at least two surfaces with the first flexible pattern on the first surface and a second flexible pattern on a second surface. In some examples, the flexible surface includes six surfaces each having a flexible pattern.

In some examples, the flexible surface is included in a body of an implant or an instrument. In some of these examples, the body may include at least one non-flexible surface. In other examples, the body may have at least one smooth surface. In some examples, the body may have at least one surface with a plurality of projections and a plurality of grooves. In some examples, the plurality of slits may extend through the body. In other examples, the plurality of slits may extend through less than an entirety of the body. In some examples, the plurality of slits may include at least two slits that are oriented at different angles relative to the flexible surface.

In another aspect, the present disclosure relates to an interbody implant that includes a body. The body includes a first opening that defines a first pathway and a second opening that defines a second pathway transverse to the first pathway. The first opening is bound by a first inner surface of the body, the first inner surface being curved and having a flexible surface region thereon. The flexible surface region includes a continuous segment adjacent to a first slit on one side and a second slit on a second side and extends from a first end to a second end with at least two bends therebetween.

In some examples, the first slit may be C-shaped and the second slit may be T-shaped. In some examples, the continuous segment may include a protrusion in between the first end and the second end. In some examples, the second opening may be bound by a second inner surface of the body, the second inner surface being curved and having a hook-shaped element extending therefrom to a free end. In some examples, the hook-shaped element may include a tip extending into the second pathway of the second opening.

Additional objects and advantages of the disclosure will be set forth in part in the description which follows or may be learned by practice of the embodiments of the disclosure.

It is to be understood that both the foregoing general description and the following detailed description are exemplary and explanatory only and are not restrictive of the embodiments of the disclosure, as claimed.

BRIEF DESCRIPTION OF THE DRAWINGS

Various embodiments of the present disclosure are described herein below with reference to the drawings, wherein:

FIG. 22A is an exploded view of an adjustable cage according to one embodiment of the disclosure.
FIG. 22B is an isometric view of the adjustable cage of FIG. 22A.
FIG. 22C is a top view of one example of an endplate for the adjustable cage of FIG. 22A.

DETAILED DESCRIPTION

Figure 1A:
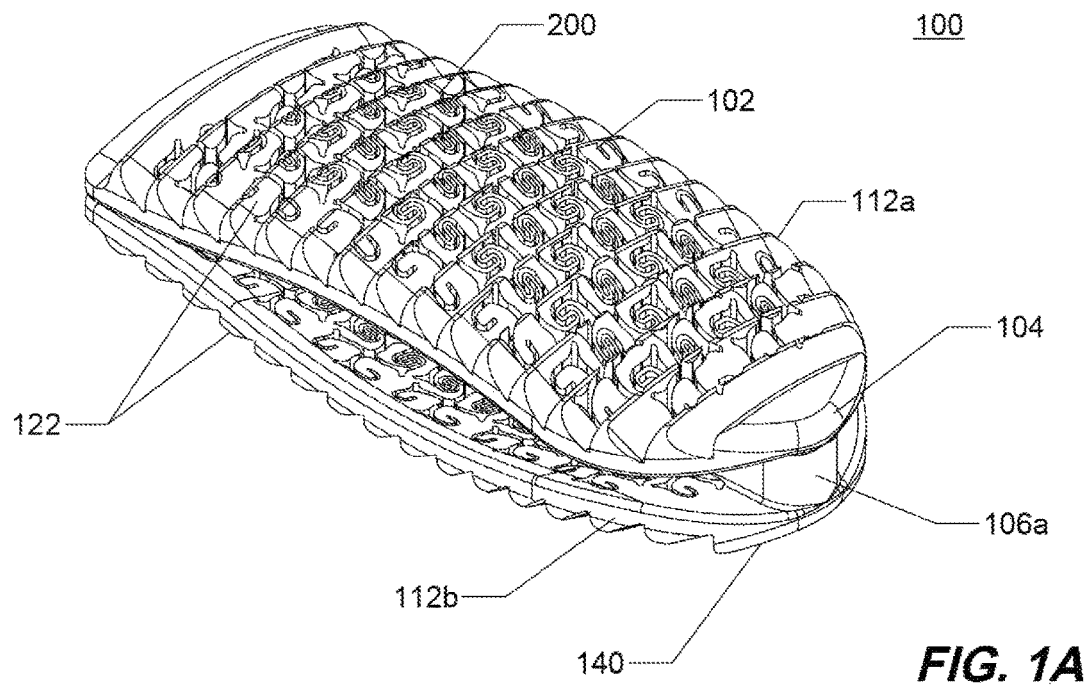
FIG. 1A is an isometric view of an interbody.

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

In the drawings and in the description that follows, the term "proximal" refers to the portion of the device that is closest to the operator, while the term "distal" refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Flexible Interbody

In one aspect, the present disclosure is directed an interbody comprising at least one surface with a flexible pattern, wherein the flexible pattern includes a continuous line of material. The flexibility of a surface can be determined by various techniques including determining the stiffness of a surface, i.e., the resistance of a surface to elastic deformation. Stiffness is a measure of the applied force divided by the deflection of the surface. Variables associated with the flexible pattern can alter the stiffness of the surface. By selecting certain variables, a specific stiffness can be achieved in response to a given load. The flexible pattern can provide a stiffness to a surface that can be measured, for example, using a compressive load. The stiffness of a surface including a flexible pattern relative to another surface without the flexible pattern can vary from about 25% to about 100%, for example, from about 35% to about 90%, and as a further example from about 50% to about 80%.

Referring now to FIGS. 1A-1C, 11A-11C, 13A-13D, 14A-14D, and 15A-15B, there is disclosed an embodiment of an interbody 100 for engagement between vertebrae. As can be seen from the various Figures, an interbody 100 can have various configurations and the present application is intended to cover various configurations such as those illustrated in the Figures. The interbody 100 can have at least one surface, such as two surfaces each independently with a flexible pattern 200. In an aspect, the interbody 100 can have up to six surfaces each independently with a flexible pattern 200. The interbody 100 includes a body 102 having a substantially contoured first end surface 104 at a distal or leading end of the body 102 and a second end surface 108 opposite thereto at a proximal or trailing end of the body 102. The body 102 extends between the first and second end surfaces 104 and 108 to define respective top and bottom vertebral engaging surfaces 112a, 112b, as well as opposed side surfaces 162a, 162b. The top and bottom vertebral engaging surfaces 112a, 112b are disposed opposite to one another.

Figure 11A:
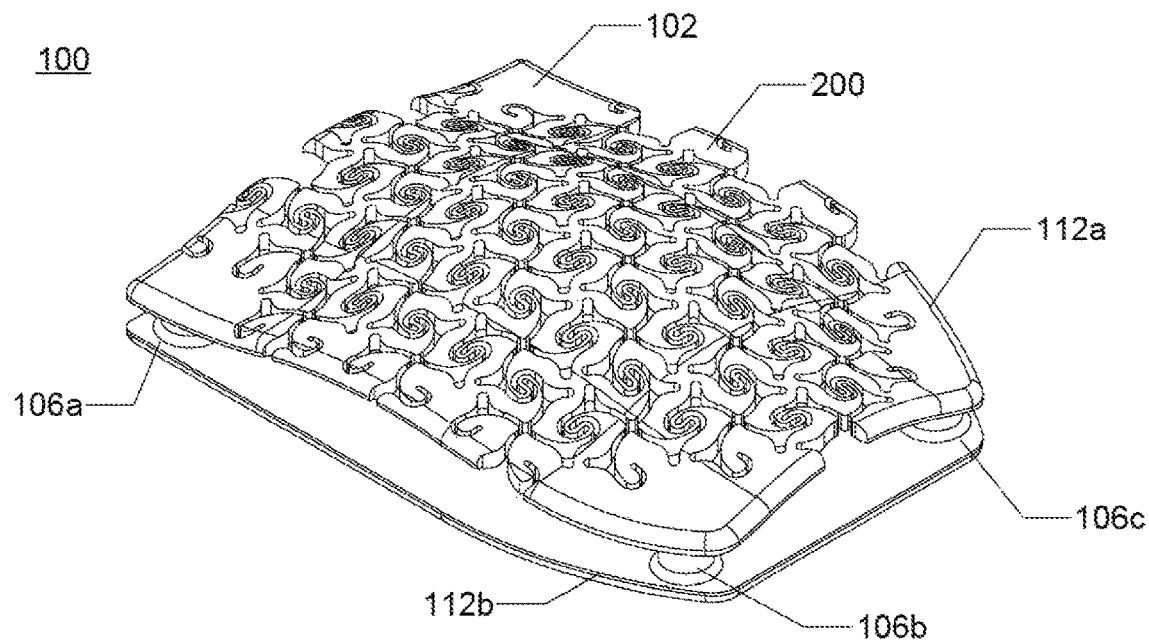
FIG. 11A is an isometric view of an aspect of an interbody with a flexible pattern.
Figure 11B:
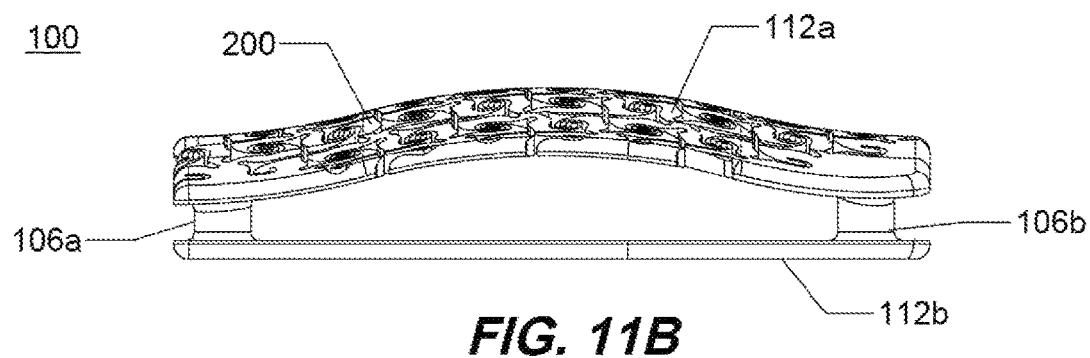
FIG. 11B is a side view of FIG. 11A.
Figure 11C:
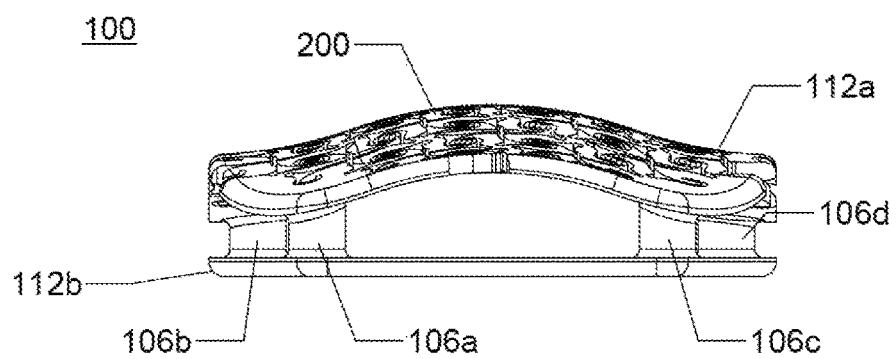
FIG. 11C is a front view of FIG. 11A.

The body 102 can be configured such that the top and bottom vertebral engaging surfaces 112a, 112b intersect the side surfaces 162a, 162b, respectively, to provide a substantially quadrilateral cross-section with rounded corners 140, as illustrated in FIGS. 13A, 13C, 13D, and 14D. The body 102 has, by way of example, a substantially rectangular cross-section, although other quadrilateral shapes such as a square are also contemplated, as illustrated in FIGS. 11A-11C. In addition, the cross-section shape may also be hexagonal or other suitable multilateral shape. The shape of the body 102 is not limited in this context.

Figure 1B:
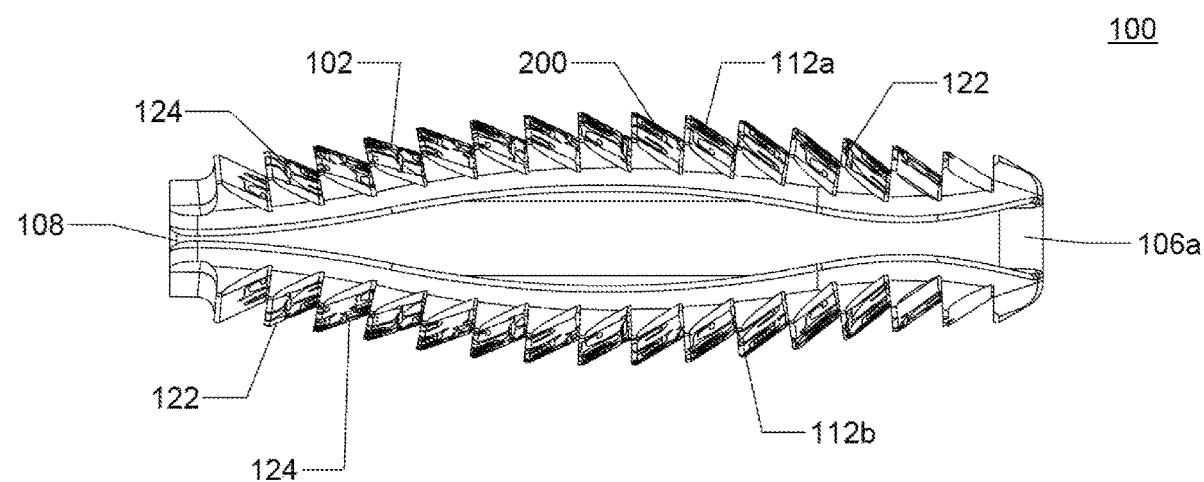
FIG. 1B is a side view of FIG. 1A.
Figure 1C:
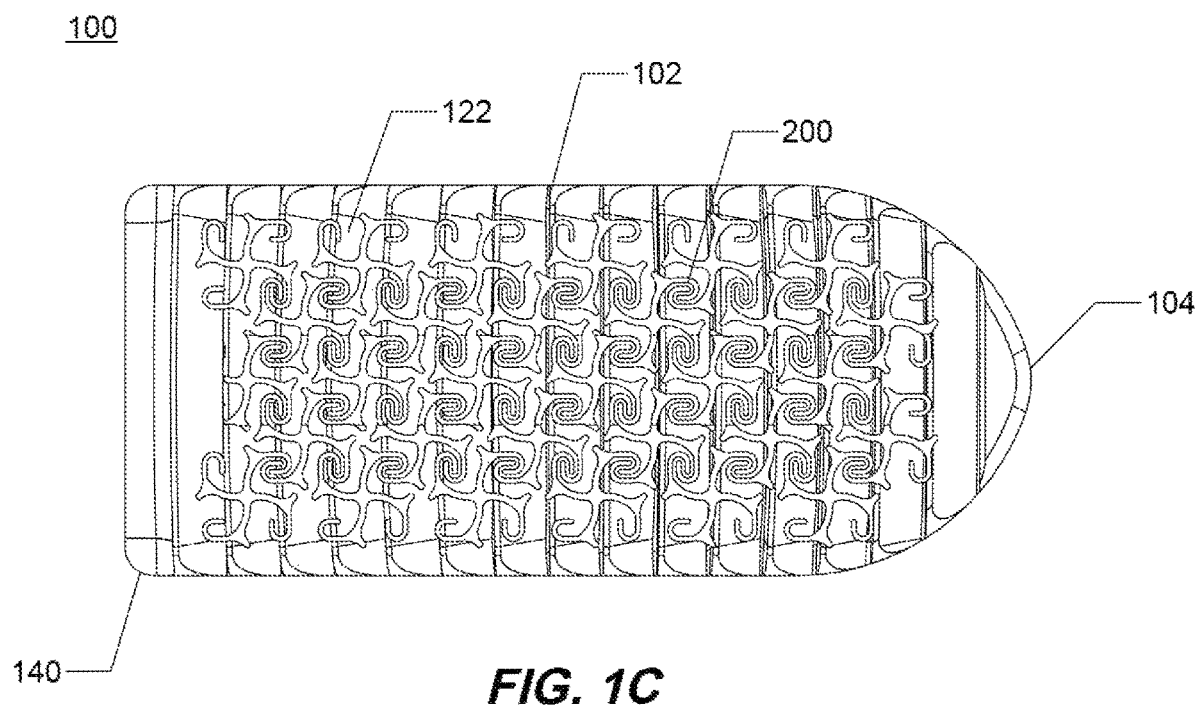
FIG. 1C is a top view of FIG. 1A.
Figure 13A:
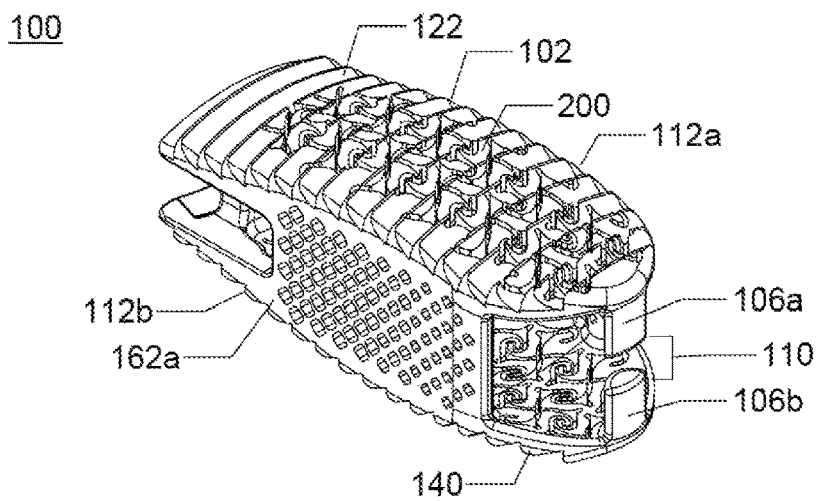
FIG. 13A is an isometric view of an interbody with a flexible pattern.
Figure 13B:
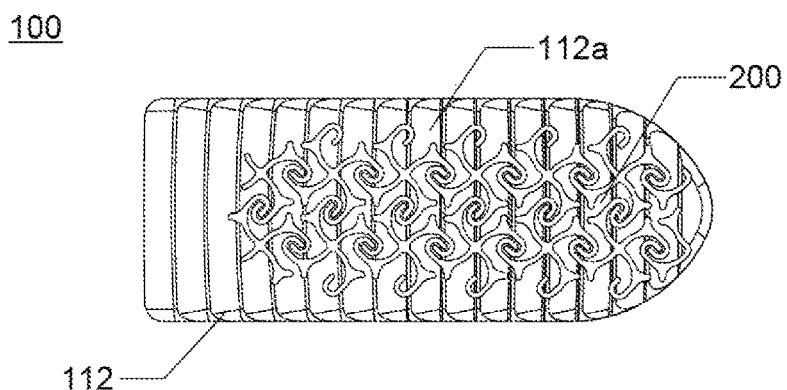
FIG. 13B is a top view of FIG. 13A.
Figure 13C:
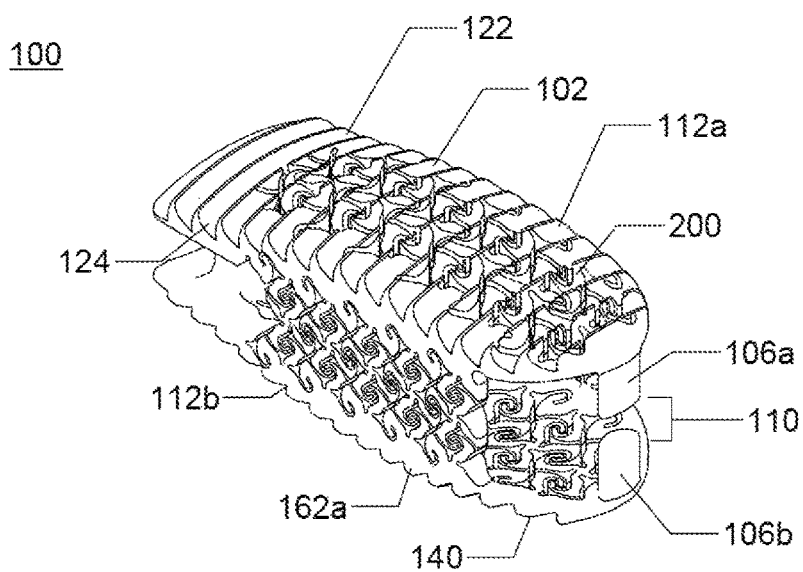
FIG. 13C is an isometric view of an interbody with a flexible pattern according to another aspect.
Figure 13D:
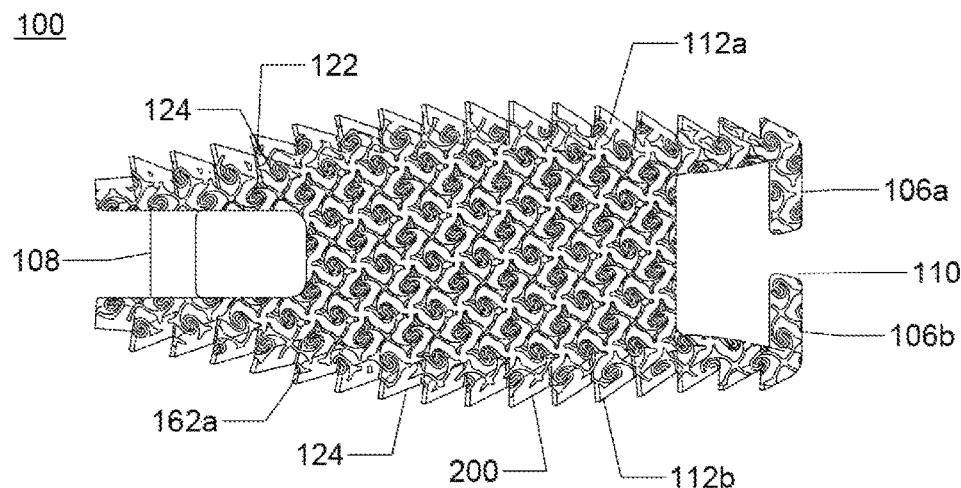
FIG. 13D is a side view of FIG. 13C.
Figure 14A:
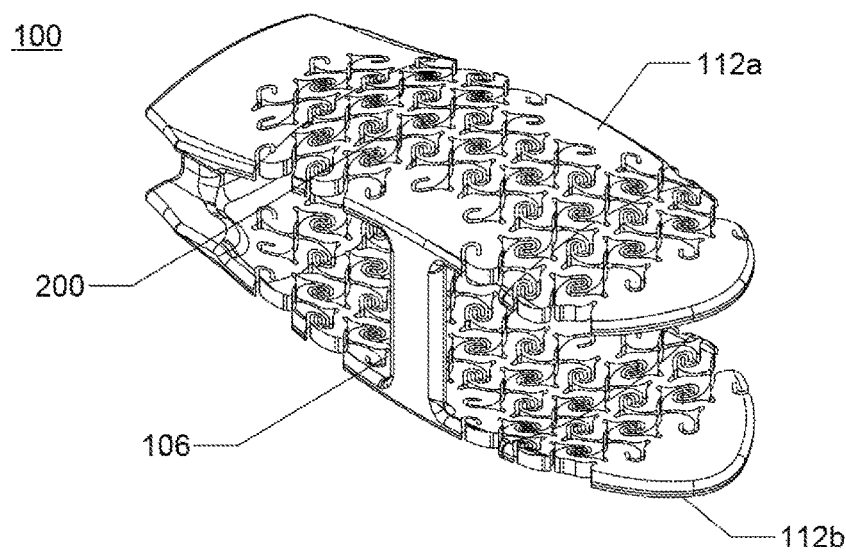
FIG. 14A is an isometric view of an interbody with a flexible pattern.
Figure 14B:
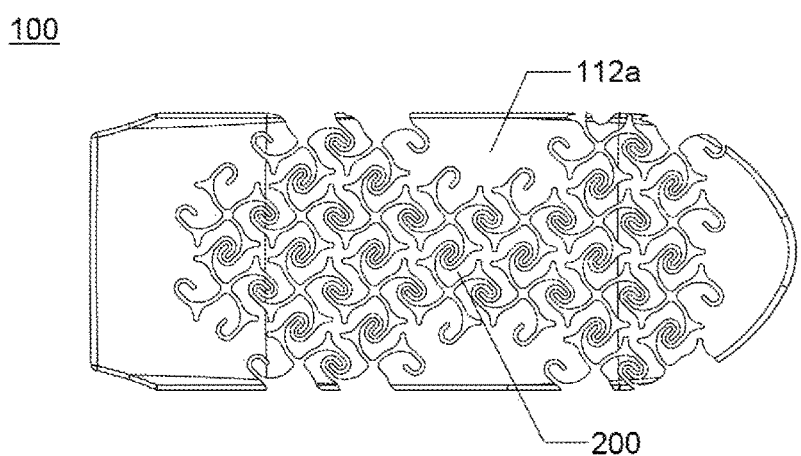
FIG. 14B is a top view of FIG. 14A.
Figure 14C:
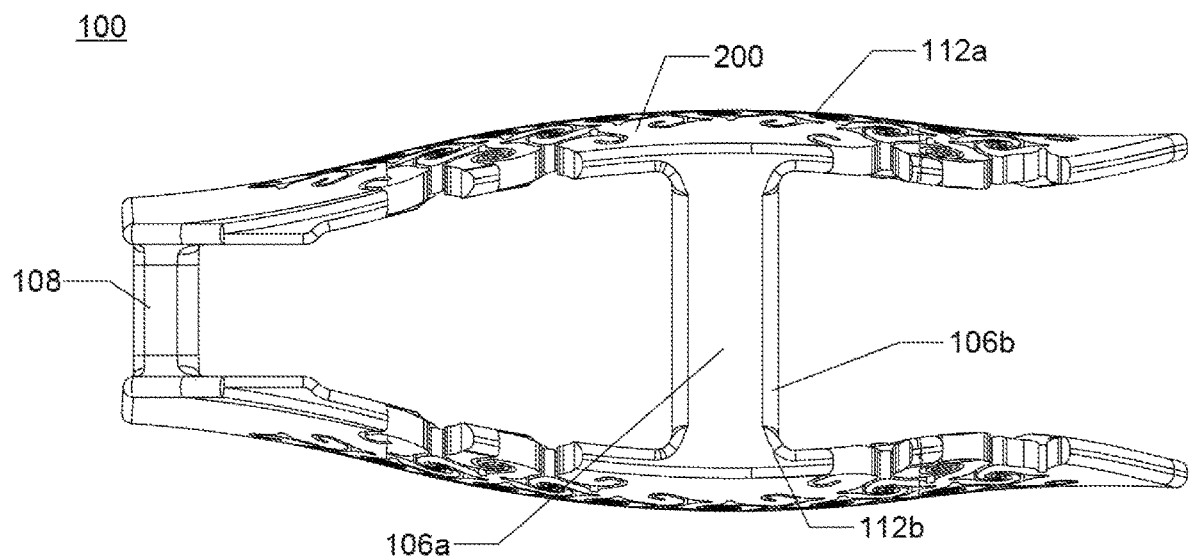
FIG. 14C is a side view of FIG. 14A.
Figure 14D:
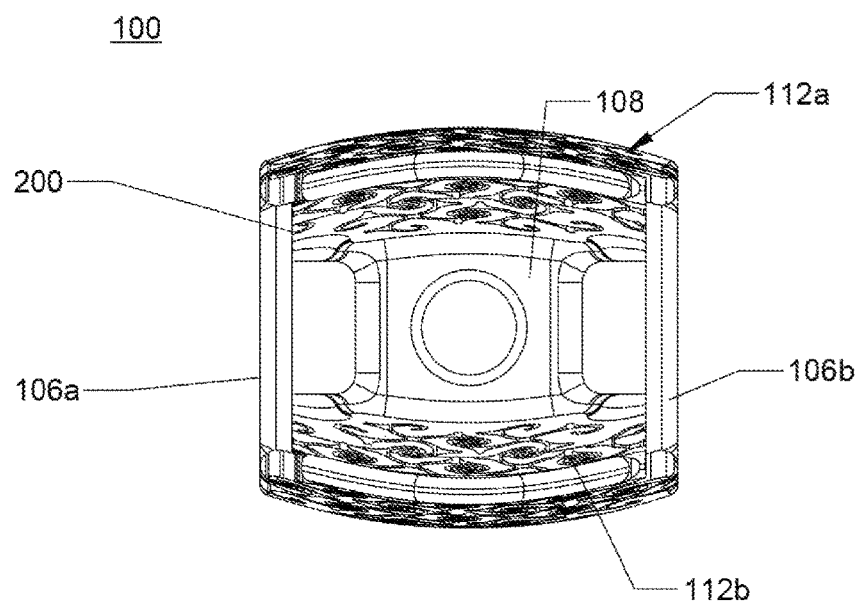
FIG. 14D is a front view of FIG. 14A.

In another aspect, the body 102 can be configured such that the top and bottom vertebral engaging surfaces 112a, 112b intersect posts 106, to provide support to the body 102 with minimal structural elements, as illustrated in FIGS. 14A, 14C and 14D. The posts 106 can be located at a corner of the body, as illustrated in FIGS. 11A-C. In another aspect, a post 106a can extend from the top vertebral engaging surface 112a, and another post 106b can extend from the bottom engaging surface 112b with a gap 110 between the posts 106a, 106b, as illustrated in FIGS. 13A, 13C, and 13D. In another aspect, the post 106 can be located at first end surface 104, as illustrated in FIGS. 1A and 1B. The post 106 can be located anywhere between the top and bottom vertebral engaging surfaces 112a, 112b. The body 102 can include more than one post 106. The post 106 can provide support to the body 102 while reducing the amount of material needed to make the body 102, and increasing the open space within the body 102 to allow for bone ingrowth.

The body 102 can also be configured such that the top and bottom vertebral engaging surfaces 112a, 112b have a convex profile, as illustrated in FIGS. 1A, 1B, 11A-11C, 13A, 13C, 14A, and 15B. In another aspect, the body 102 can be configured so that the top and bottom vertebral engaging surfaces 112a, 112b have a flat, planar profile; a convex profile, or a profile that varies across a length of the body 102. The body 102 can be configured to be symmetrical around a centerline axis X-X that extends from the first end 104 to the second end 108. The body 102 can be configured so that the side surfaces 162a, 162b have an atraumatic blunt nose profile with respect to the contoured first end 104.

In an aspect, the top and bottom vertebral engaging surfaces 112a, 112b can be the same or different. In particular, each of the top and bottom vertebral engaging surfaces 112a, 112b can independently have a smooth configuration or a plurality of protrusions 122 in a particular configuration. A smooth configuration is shown in FIGS. 11A-11C, 14A-14D, and 15A-15B. As shown in FIGS. 1A-1C, and 13A-13D, the plurality of protrusions 122 define a set of grooves 124 that face towards the second end 108. Each groove of the set of grooves 124 has a position along the top and bottom vertebral engaging surfaces 112a, 112b. Each groove of the set of grooves 124 includes a first face that is orthogonal to the top and bottom vertebral engaging surfaces 112a, 112b, i.e., to the axis X-X, at the respective position of the groove. Each groove of the set of grooves 124 includes a second opposing face that can be sloped or inclined with respect to the top and bottom vertebral engaging surfaces 112a, 112b so that the surfaces converge at the bottom of the groove 124.

The interbody 100 can comprise at least one surface with a flexible pattern 200, in which the flexible pattern 200 includes a continuous line of material. As discussed herein, the interbody 100 can include top and bottom vertebral engaging surfaces 112a, 112b, post 106, side surfaces 162a, 162b, first end 104, and second end 108. The interbody 100 can include at least two surfaces each with a flexible pattern 200, as shown in FIGS. 1A, 1B, 13A, 13C, 14A, 14C, and 14D. In an aspect, the interbody 100 can have one, two, three, four, five, or up to six surfaces each independently with a flexible pattern 200. For example, the interbody 100 can include a top surface 112a with a flexible pattern 100, a bottom surface 112b with a flexible pattern 200, first end 104 and second end 108 each with a flexible pattern 200, and two side surfaces 162a, 162b with a flexible pattern 200.

Each surface of the interbody 100 can be independent from any other surface of the interbody 100 in terms of variables, such as degree of flexibility, degree of rigidity, density of the flexible pattern 200, form of the flexible pattern 200, thickness of the surface including the flexible pattern 200, and etc. One of these variables may impact another variable. For example, a thick top surface 112a with a flexible pattern 200 can have a higher degree of rigidity as compared to a thin bottom surface 112b with a flexible pattern 200 within the same interbody 100.

Figure 16A:
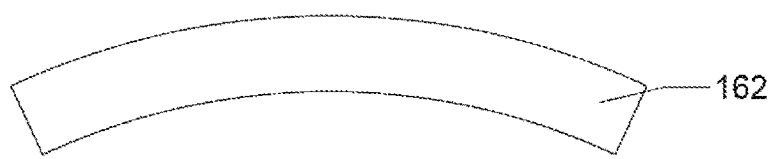
FIGS. 16A-C are a side view illustrating degrees of curvature of a surface including a flexible pattern.
Figure 16B:
Figure 16C:
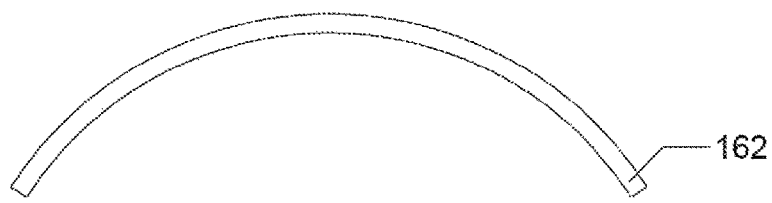
Figure 17A:
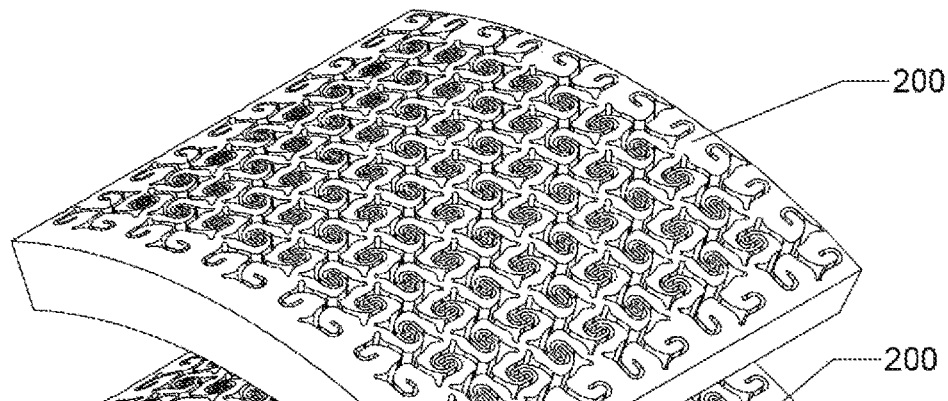
FIGS. 17A-C are isometric views of FIGS. 16A-C, respectively.
Figure 17B:
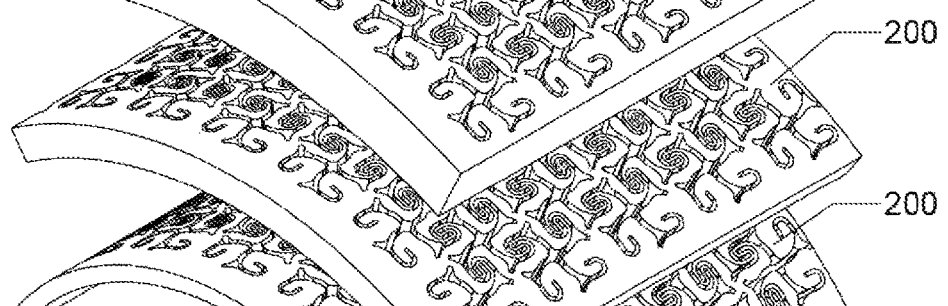
Figure 17C:
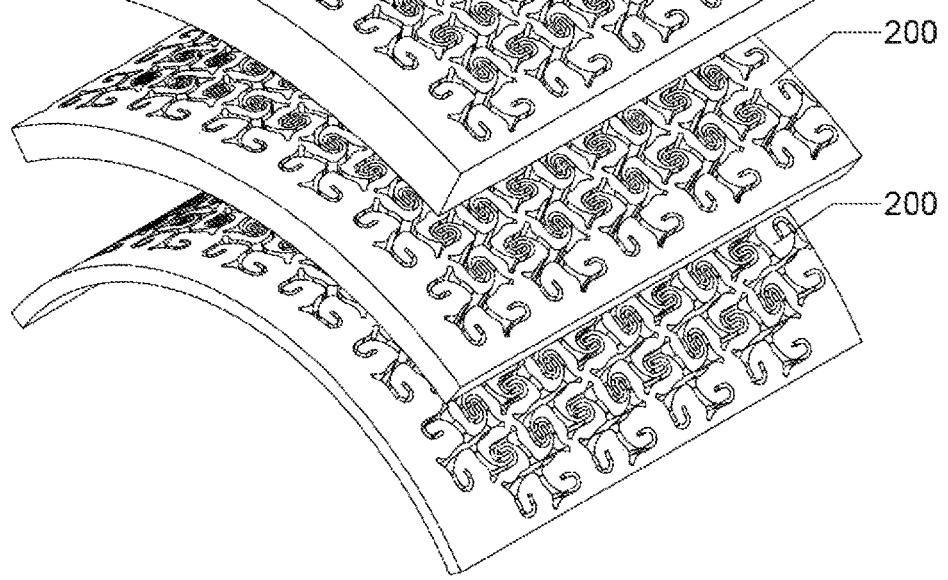

FIGS. 16A-C illustrate the side view of, for example, a surface having a flexible pattern 200, as shown in FIGS. 17A-C, respectively. FIG. 16A illustrates a surface that is thicker than a surface as shown in FIG. 16B, which is thicker than a surface as shown in FIG. 16C. FIGS. 16A-C and FIGS. 17A-C illustrate that a thin surface with a flexible pattern 200 (see, e.g., FIGS. 16C and 17C) can have a greater degree of flexibility as compared to a thicker surface with a flexible pattern 200 (see, e.g., FIGS. 16A and 17A).

Figure 2A:
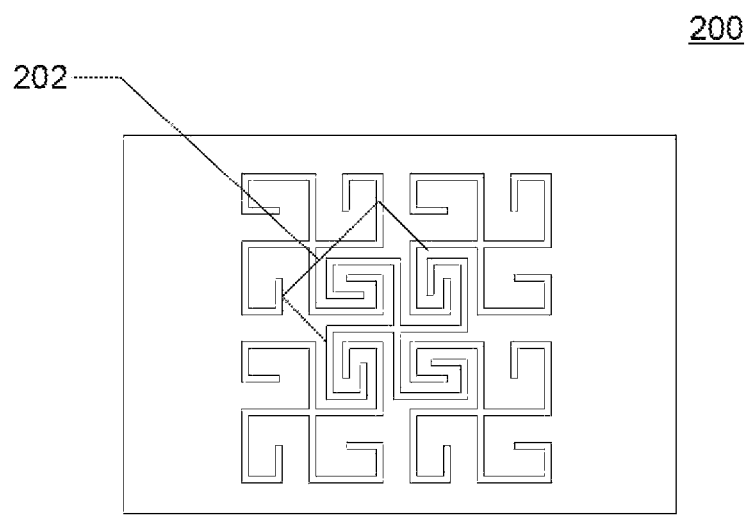
FIG. 2A illustrates an example of a flexible pattern.
Figure 3A:
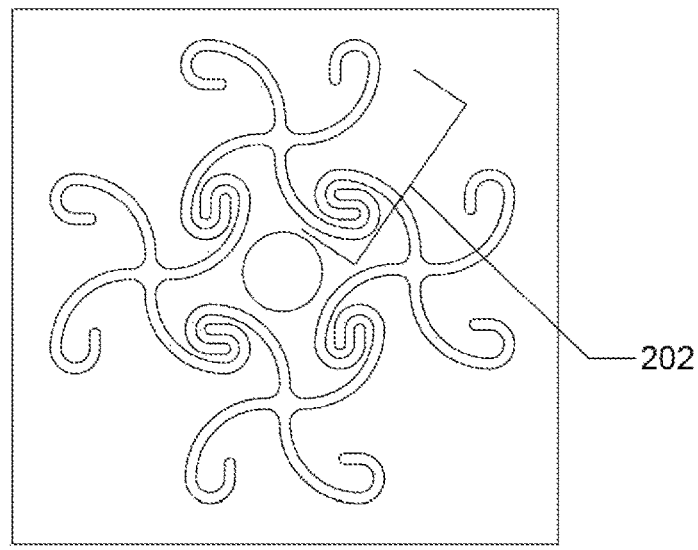
FIG. 3A illustrates an example of a flexible pattern.
Figure 3B:
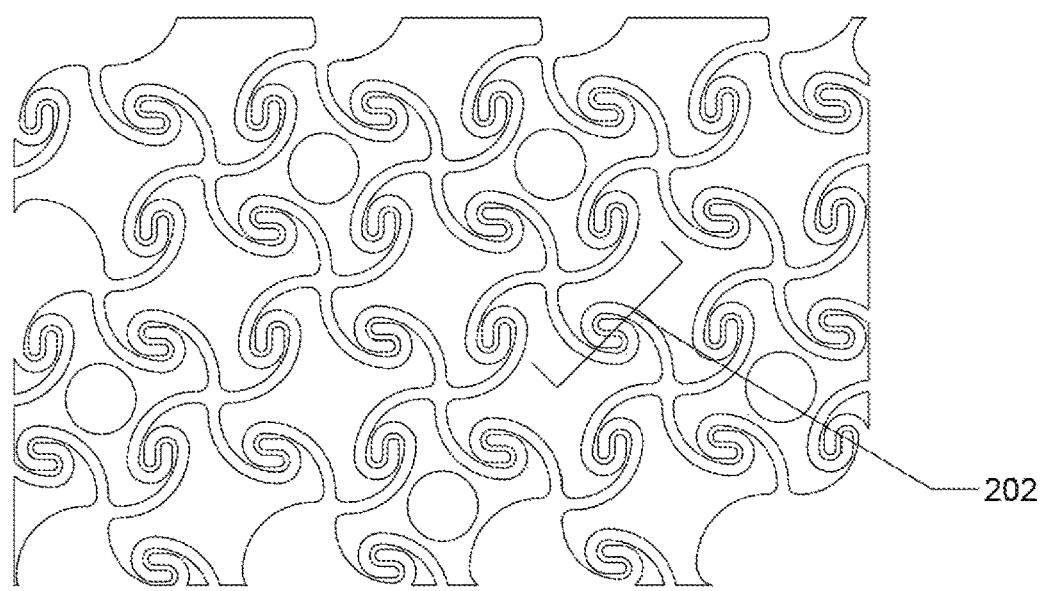
FIG. 3B illustrates another example of the flexible pattern of FIG. 3A.
Figure 4A:
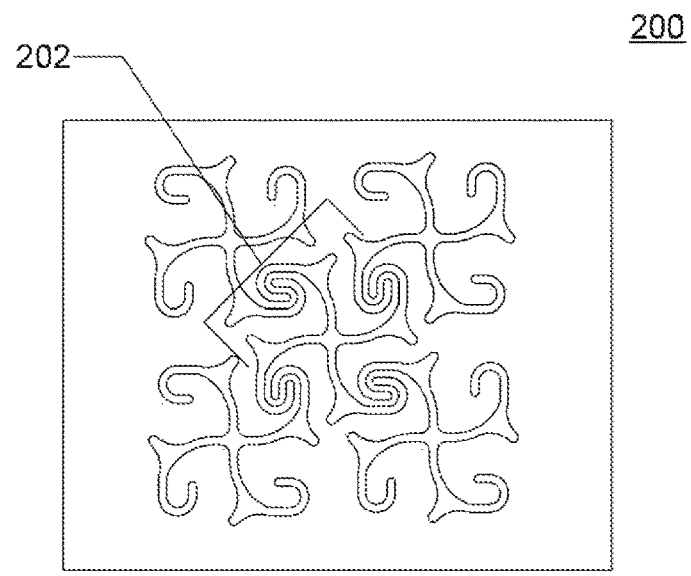
FIG. 4A illustrates an example of a flexible pattern.
Figure 4B:
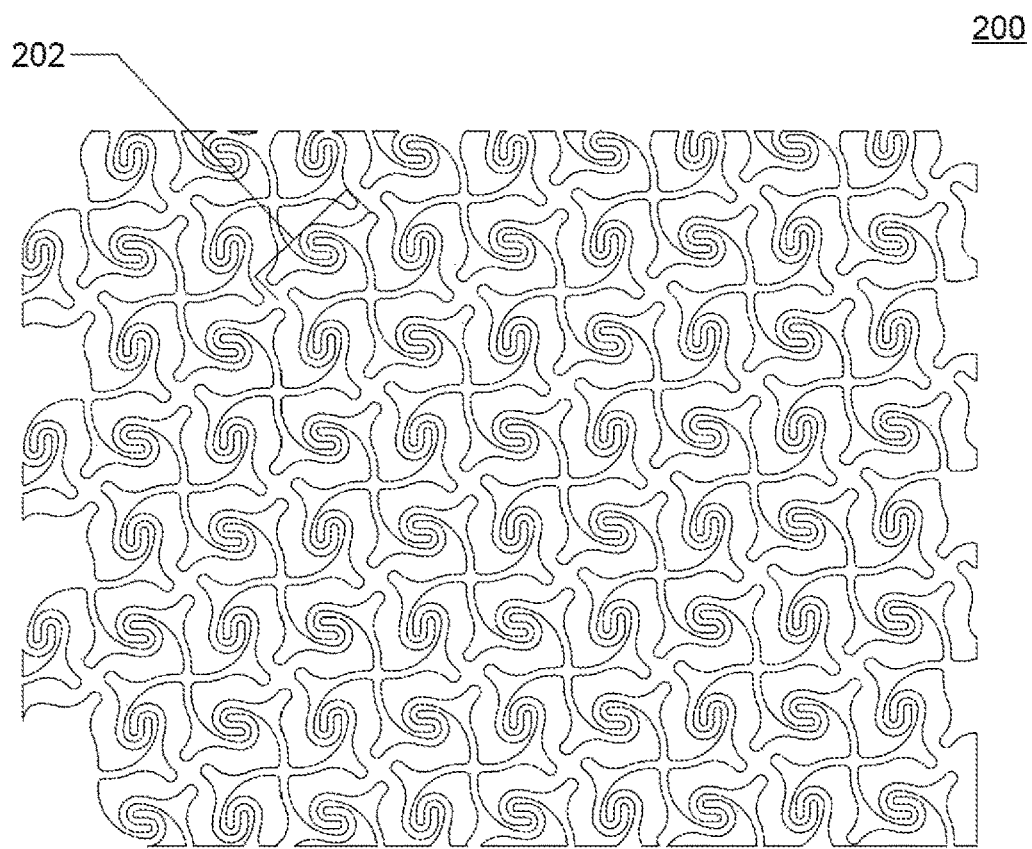
FIG. 4B illustrates another example of the flexible pattern of FIG. 4A.
Figure 15A:
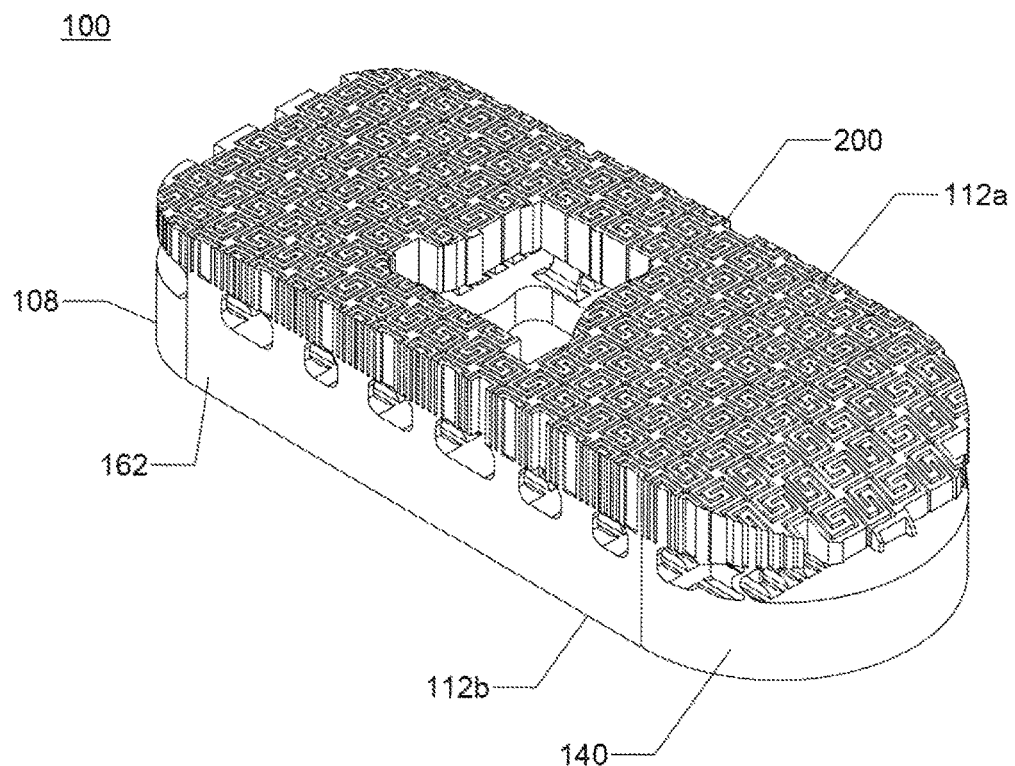
FIG. 15A is an isometric view of an interbody with a flexible pattern according to an aspect.
Figure 15B:
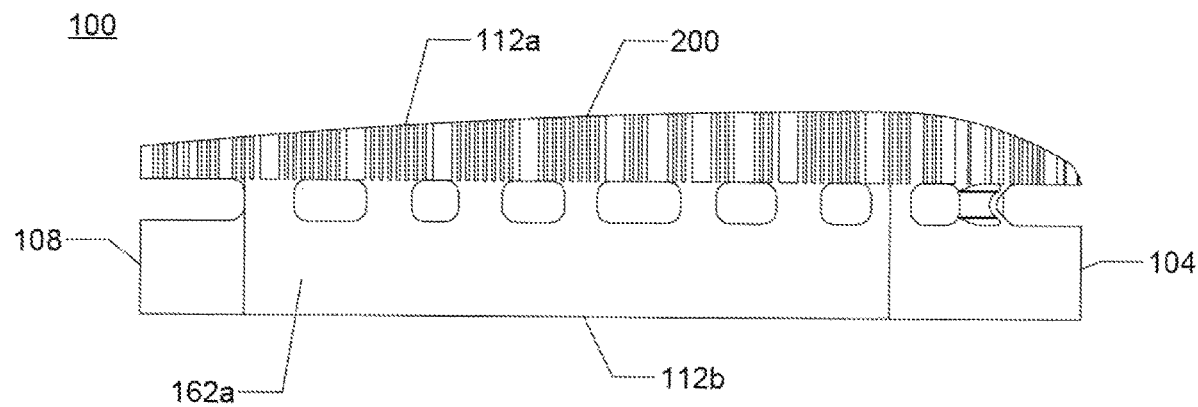
FIG. 15B is a side view of FIG. 15A.

As another example, of how one variable of the flexible pattern 200 can effect another variable of the flexible pattern 200, an end surface 108 can have a dense flexible pattern 200 including curved line as shown in FIG. 3B, a side surface 162a can have a less dense flexible pattern 200 comprising squared lines as shown in FIG. 2A, and a top surface 112a can have a varied thickness across the length of the interbody as shown in FIG. 15B. It is appreciated that each surface with a flexible pattern 200 of an interbody 100 can be designed to meet the requirements for its particular use.

As shown in FIGS. 2A, 2B, 3A, 3B, 4A, 4B, and 5A-5D, the flexible pattern 200 can include a continuous line of material. As shown in FIGS. 2A, 2B, 3A, 3B, 4A, 4B, and 5A-5D the shaded area is the continuous line of material forming the flexible pattern 200. The white area is the absence of material. The flexible pattern 200 can include a plurality of segments 202 that interconnect to form rows and columns. A segment 202 can include a first end and a second end in which the first end of each segment 200 can interconnect with at least one second end of another segment of the plurality of segments, for example in an adjacent row or column. In an aspect, a first end of a segment 202 can interconnect with three different segments to form the flexible pattern 200 with a continuous line of material. In a further aspect, a second end of a segment 202 can interconnect with three different segments to form the flexible pattern 200 with a continuous line of material.

Figure 5A:
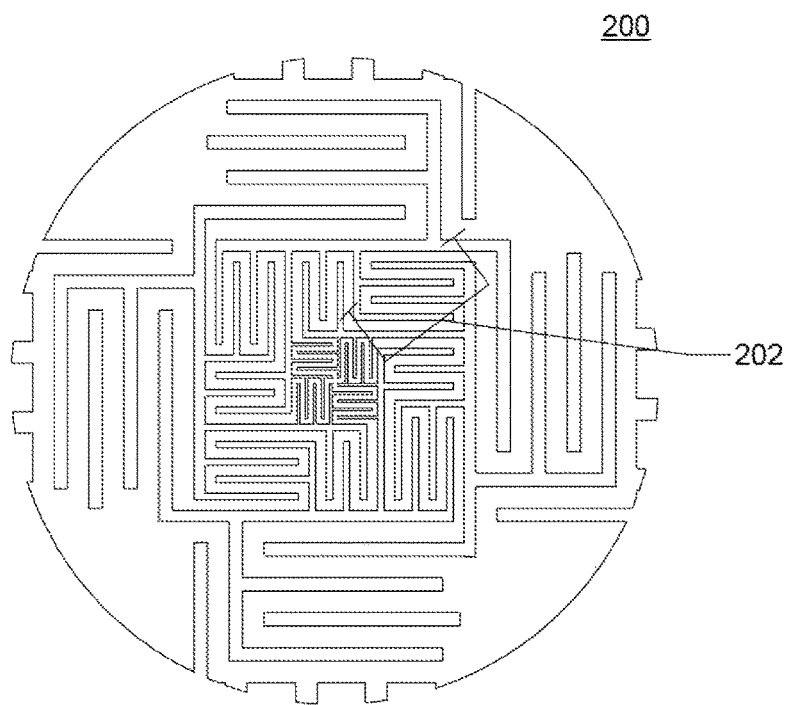
FIG. 5A illustrates an additional example of the flexible pattern according to other aspects.
Figure 5B:
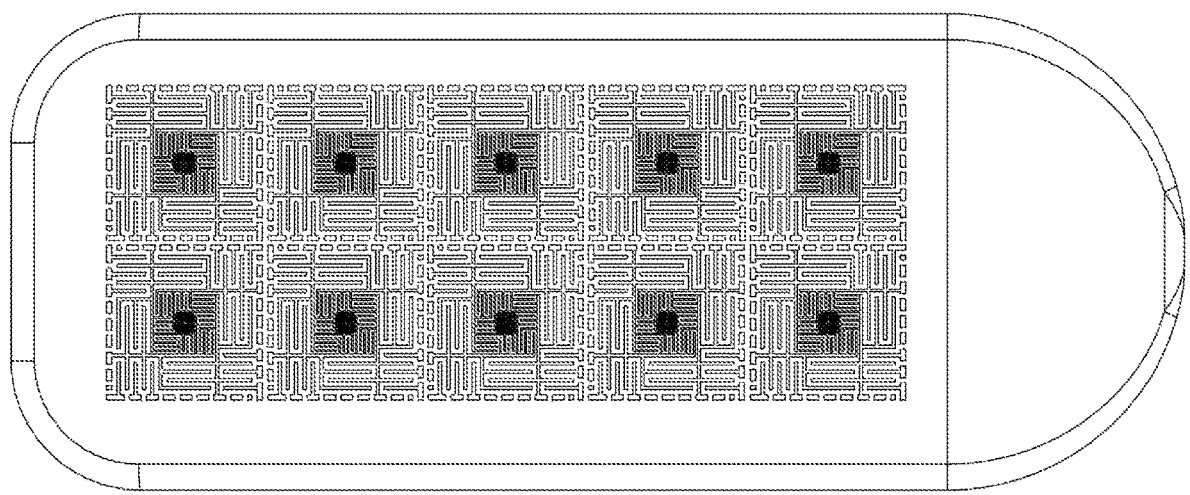
FIG. 5B illustrates a top view of a surface including the flexible pattern of FIG. 5A.

In another aspect as shown in FIG. 5A, the segment 202 can flip orientations within the continuous line of material so that in a first configuration the segment forms rows and in an adjacent second configuration the segment forms columns. The flexible pattern can also increase in size. For example, as shown in FIG. 5A, the innermost columns and rows are smaller in size than the outermost columns and rows. Accordingly, the stiffness in the interior of the flexible pattern 200 is expected to be lower than a stiffness along the outer edges, e.g., perimeter, of the flexible pattern 200. The flexible pattern 200 illustrated in FIG. 5A can be a single continuous radius across an entire or a portion of a surface. In another aspect, the flexible pattern 200 illustrated in FIG. 5A can be multiple separate squares across an entire or a portion of a surface, as shown in FIG. 5B.

Figure 5C:
FIG. 5C illustrates an additional example of the flexible pattern according to other aspects.
Figure 5D:
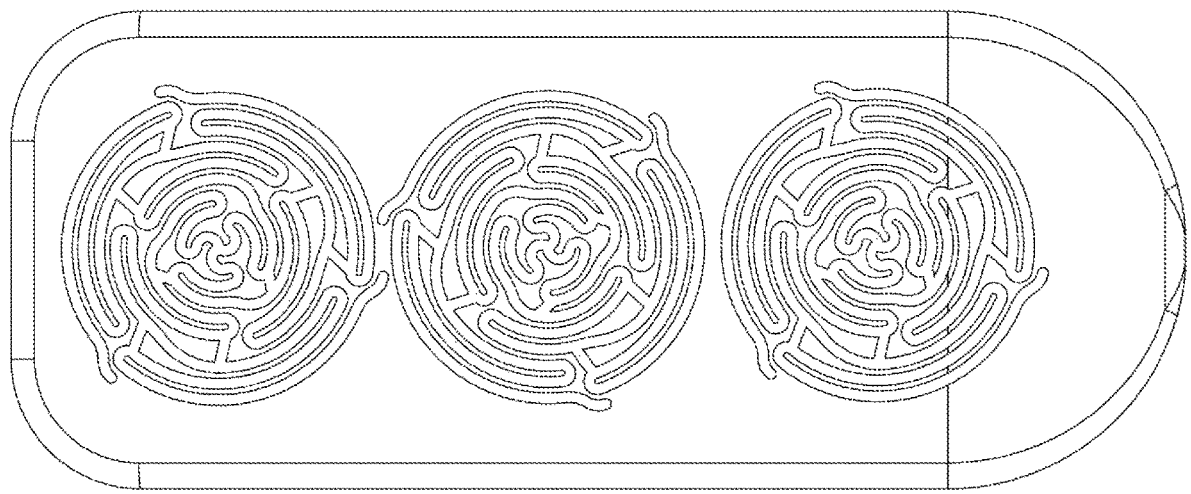
FIG. 5D illustrates a top view of a surface including the flexible pattern of FIG. 5C.

In another aspect as shown in FIG. 5C, the flexible pattern 200 may include a plurality of segments that interconnect to mimic a pattern of cortical bone. The segments switch back and forth in an arching pattern and/or curlicue pattern. The stiffness in the interior of the flexible pattern 200 is expected to be higher than a stiffness along the outer edges, e.g., perimeter, of the flexible pattern 200. The flexible pattern 200 illustrated in FIG. 5C can be a single continuous radius across an entire or a portion of a surface. In another aspect, the flexible pattern 200 illustrated in FIG. 5C can be multiple separate spheres across an entire or a portion of a surface, as shown in FIG. 5D.

The flexible pattern 200 can flex under application of a force. In an aspect, a first area of the flexible pattern 200 can move in a direction relative to a second area of the flexible pattern 200 under an applied force.

Figure 2B:
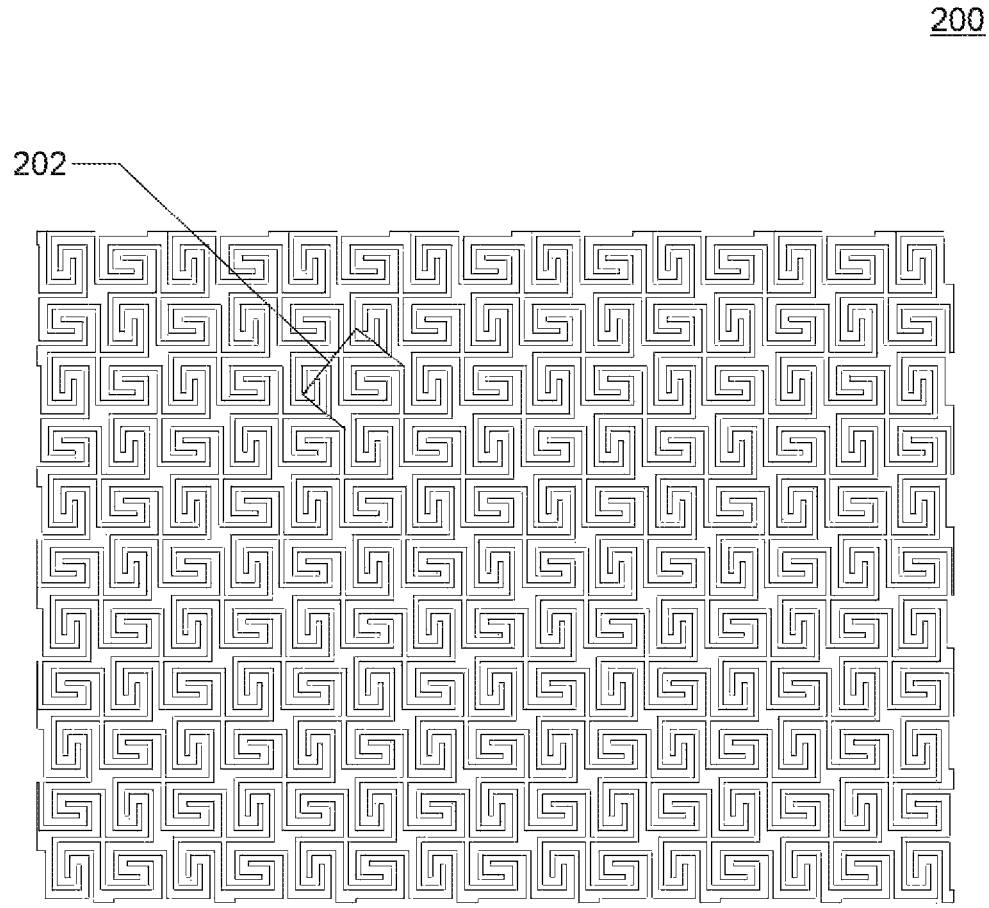
FIG. 2B illustrates another example of the flexible pattern of FIG. 2A.

As shown in FIGS. 2A, 2B, and 5A, the flexible pattern 200 can include a continuous line of material that forms corners, which can be used to form smaller or denser patterns. A flexible pattern 200 with corners can be harder to manufacture. As shown in FIGS. 3A, 3B, 4A, 4B, and 5C, the flexible pattern 200 can comprise curves, arches, and/or curlicues, which can be used to form larger or less dense patterns. A flexible pattern 200 with curves, arches, and/or curlicues can be easier to manufacture.

Figure 6:
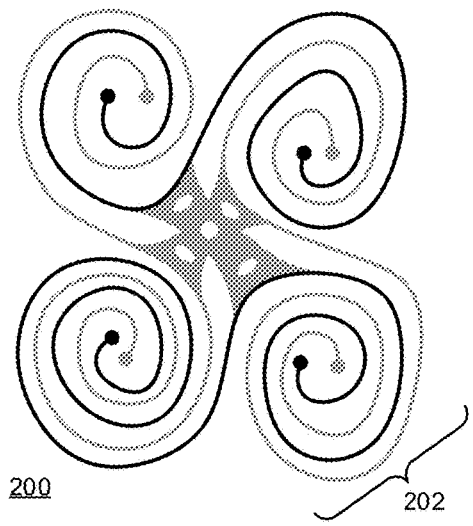
FIGS. 6-10 illustrate still further examples of a flexible pattern.

Other examples of flexible patterns with continuous lines of material are shown in FIGS. 6, 8, 9 and 10. FIG. 6 illustrates a flexible pattern 200 with a plurality of segments 202 in the form of swirls spaced around a central region. In the variation shown, there are four swirls in total, each one including a continuous line of material left from cutting a larger interbody structure. The continuous line of material extends from an outer dimension and spirals inward toward a center of the swirl. Each continuous line of material originates in a center material region centered between the swirls and includes a plurality of openings therein. In a variant, the central region may be solid and without swirls. FIG. 6 illustrates that each swirl is circumferentially offset with respect to the others around the center material region and each swirl is approximately the same distance from the center material region. In one variant, the flexible pattern 200 of FIG. 6 may be comprised of different materials, such as materials alternating with each continuous line. In this manner, the flexible pattern may be lamellar.

Figure 8:
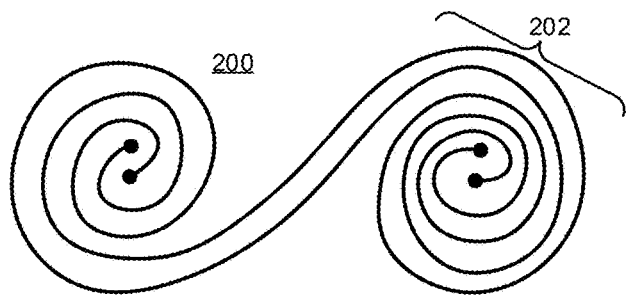
Figure 9:
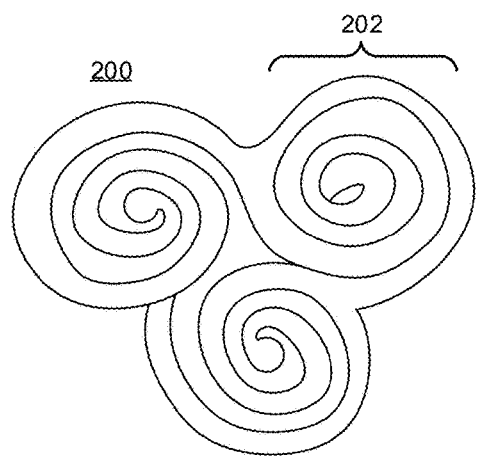

In FIG. 8, the flexible pattern 200 is defined by a continuous line of material defining an "S" shape. The flexible pattern includes two separate segments 202 in the form of swirls. Each continuous line of material is defined by a pair of material cut outs spiraling outward from a center of a respective spiral. At an outer perimeter of the spiral, the pair of cut outs extend across a central region to an opposing swirl. Each swirl has a similar structure, and both include a continuous line of material defined by a pair of cut outs that extend from a center of the swirl in a counterclockwise direction. Of course, a direction of one or both of the continuous lines of material from the center of the swirls may be reversed. FIG. 9 illustrates another flexible pattern 200 with three segments 202 combined so that the flexible pattern has a generally triangular shape. Each segment 202 is in the form of a swirl and is defined by a continuous line of material spiraling outward from a center of the respective swirl.

Figure 10:
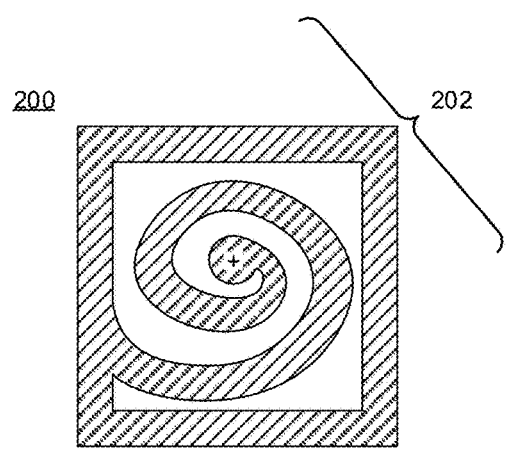

FIG. 10 illustrates yet another flexible pattern 200 in the form of a single spiral surrounded by solid material. A continuous line of material defines the spiral in this configuration.

The continuous line of material can be any biocompatible material, such as a metal, an alloy, a polymer, and combinations thereof, such as a blend of a metal and a polymer. The continuous line of material can have a uniform width. In an aspect, a width of the continuous line of material can vary. In an aspect, the continuous line of material can include straight areas and/or curved areas.

Figure 7:
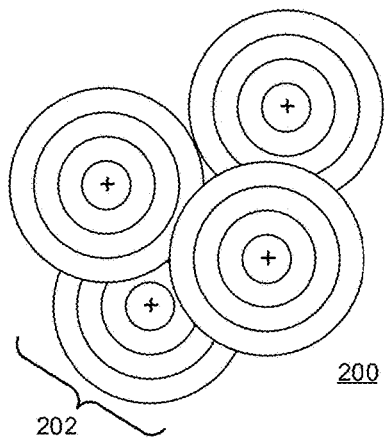

In yet another arrangement, a flexible pattern includes a plurality of concentric cut outs as shown in FIG. 7. At a center of each segment 202 is an opening abutted externally by a ring shaped portion of material, then a second opening having a ring shape, and so on. As shown, segment shapes may be overlapping. In other variations, solid material may exist in between each segment or the segments may be equal to one or more of the other segments and directly abut one another. Further variations based on the illustrated patterns are also contemplated.

Figure 18:
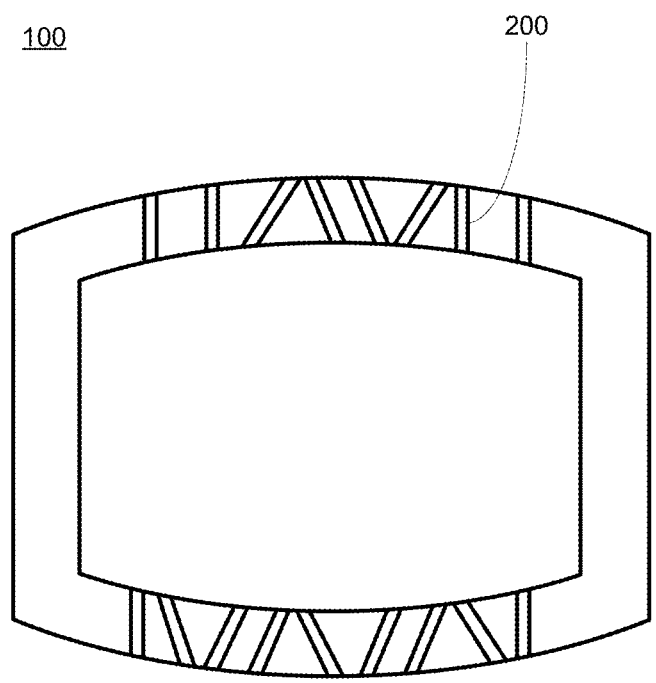
FIG. 18 is a cross sectional view of an interbody with angled gaps defining a flexible pattern.

In an aspect, the gaps, also referred to herein as cut outs, in the interbody 100 that define the flexible pattern can be oriented at an acute angle relative to a surface of the interbody 100, as shown in FIG. 18, for example. The gaps within a group of gaps may be oriented at varying angles to control a bias in the direction of flexibility of the interbody implant. For example, where a body of an implant includes ten gaps at one location on its length, three of these may be at a single acute angle relative to a surface of the body while seven may be perpendicular to the surface. In another example, two may be at a first angle, five may be at a second angle, while another three may be at a third angle. The gaps oriented at the same angle may be adjacent to one another or separated from one another. As these examples illustrate, the possible combinations of gap configurations is significant. Because the orientation of the gap(s) may alter the flexural properties of the material, it follows that the number of possibilities for a predetermined bias in deformation in any one or more parts of a surface is significant.

In any of the contemplated embodiments, cut outs that define the flexible pattern may be formed entirely through a thickness of the body of the implant. Alternatively, the cut outs may be formed through only a portion of the thickness of the body. In further alternatives, some flexible patterns may be defined by cut outs entirely through the thickness while others are formed through only a portion of the thickness. In still further alternatives, any one flexible pattern may include a first portion with cut outs through the thickness of the body and a second portion with cut outs through only part of a thickness of the body.

The at least one surface including a flexible pattern 200 can be formed by known manufacturing methods, such as additive layer manufacturing, e.g., three-dimensional printing, chemical etching, photo etching, laser cutting, water jet cutting, and traditional machining, etc. Examples of additive layer manufacturing (ALM) techniques include electron beam melting, selective laser sintering (SLS), selective laser melting (SLM), and other three-dimensional (3-D) processes. When employing these technologies, articles are produced in layer-wise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. In one example, a high energy beam is emitted from a beam-generating apparatus to heat metal powder sufficiently to sinter and preferably to at least partially melt or fully melt the metal powder. High energy beam equipment for manufacturing such structures may be one of many commercially available. The beam generation equipment may also be a custom-produced laboratory device. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664 ("the '664 patent"), the disclosure of which is incorporated by reference herein. The SLM and SLS technologies enable direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics.

Other non-powder based additive manufacturing technologies are also known to produce high resolution and dimensionally accurate articles. For example, in fused filament fabrication (FFF) or Plastic Jet Printing (PJP), strands of molten material are extruded from a nozzle to form layers onto a substrate in which the material hardens upon extrusion. Using digital light processing (DLP), photosensitive resin plastic is cured by light and built layer by layer from the bottom-up or a vat of liquid polymer is exposed to balanced levels of ultraviolet light and oxygen to produce a part often from the top-down. In inkjet 3D printing, a liquid binding material is selectively deposited across a thin layer of a powder and the process is repeated in which each new layer is adhered to the previous layer.

Figure 12D:
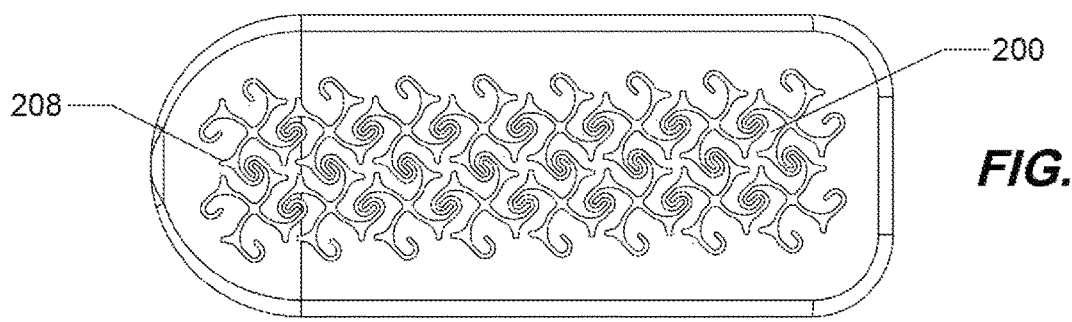
FIGS. 12A-D illustrate a top view of an interbody with various flexible patterns.
Figure 12C:
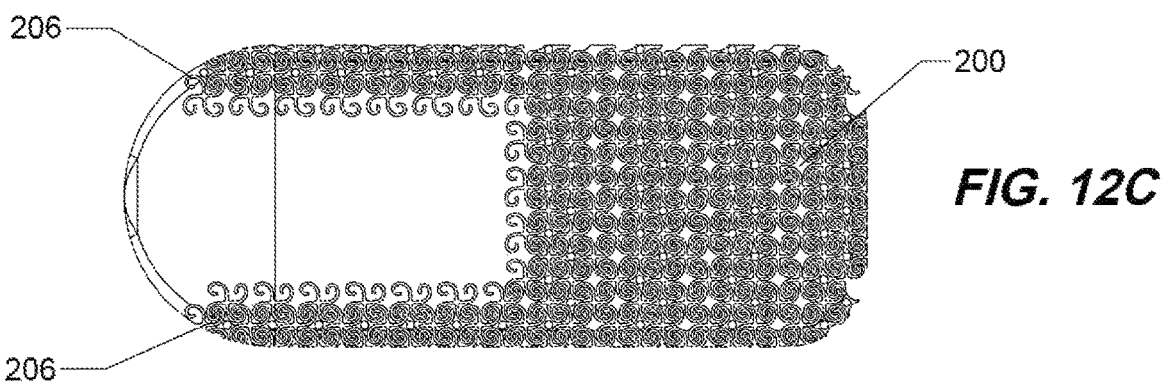
Figure 12B:
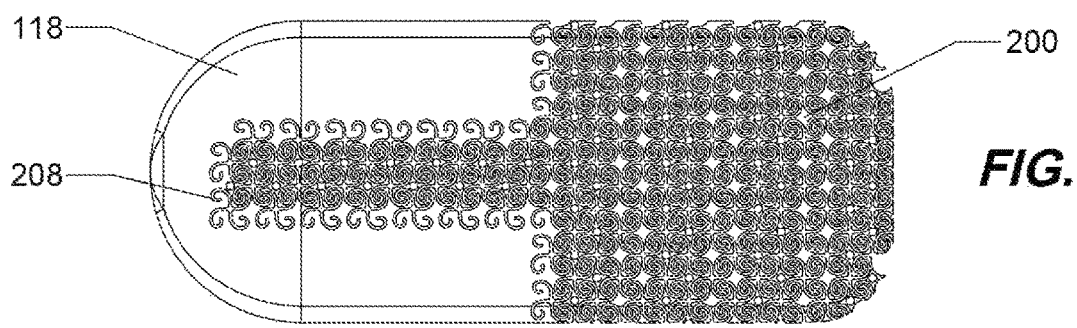
Figure 12A:
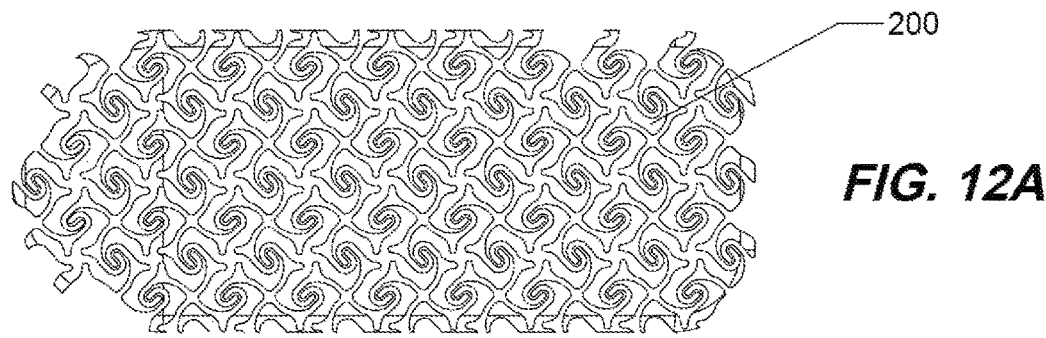

As shown in FIGS. 12A-12D, the flexible pattern 200 can be the same or different and/or can be present or absent across the at least one surface of the interbody 100. In an aspect, the flexible pattern 200 can be present across the entire surface, as shown in FIG. 12A, or can be present in sections (i.e., can be absent in sections) of the at least surface, such as shown in FIGS. 12B-12D. In another aspect, the flexible pattern 200 can be present in a section to form a perimeter 206 of the at least one surface without being present at an interior of the at least one surface, as shown FIG. 12C. The flexible pattern 200 can also be present in an interior 208, without extending to one or more edges, to form a center of the at least one surface, as shown in FIGS. 12B and 12D.

The flexible pattern 200 can transition from a perimeter to an interior so that the perimeter is more flexible than the interior and vice versa. For example, the flexible pattern 200 can transition from a less dense, i.e., farther apart, pattern at a perimeter to a more dense, i.e., closer together, pattern at an interior of the at least one surface. As a further example, the flexible pattern 200 can transition from a more dense, i.e., closer together, pattern at a perimeter to a less dense, i.e., farther apart, pattern at an interior of the at least one surface. The transition of the flexible pattern 200 can be equivalent from a perimeter to an interior and vice versa. The transition of the flexible pattern 200 can be graduated so that there are gradient zones of varying flexibility across the at least one surface.

The at least one surface can include alternating sections. For example, a first section of the at least one surface can be more rigid. A second section can be adjacent to the first section and can be more flexible. The number of alternating rigid and flexible sections can vary. The at least one surface can be more rigid depending upon variables, such as the density of the pattern and/or the thickness of the material used to form the pattern. Similarly, the at least one surface can be more flexible with, for example, a less dense pattern and/or a thinner material used to form the pattern. In another aspect, the at least one surface can include an alternating section of a first section with a flexible pattern 200 and a second section without a flexible pattern 200.

The at least one surface can have a uniform thickness, such as shown in the top engaging surface 112a in FIG. 11B. In another aspect, the at least one surface can have a thickness that varies, such as shown in the top engaging surface 112a in FIG. 15B. The thickness can vary by sections. For example, the at least one surface can have a first section that is thin adjacent to a second section that is thick (compared to the first section). The thin/thick sections can alternate across the at least one surface and can affect the flexibility of the at least one surface. In another aspect, the thickness can vary along a gradient of the at least one surface, such as from thick to thin or vice versa. It is expected that a section of the at least one surface that is thicker than another section will also be more rigid. Similarly, it is expected that a section of the at least one surface that is thinner than another section will also be more flexible, as shown in FIGS. 16A-C and FIGS. 17A-C.

Notwithstanding the presence of the flexible pattern 200, the at least one surface can be smooth or include the plurality of projections 122. A smooth surface can be even and regular, i.e., it does not include any projections 122 from the at least one surface. An array of projections 122 can inhibit movement of the interbody 102 when positioned in place. In an aspect, the interbody 100 has at least one smooth surface. In another aspect, the interbody 100 has at least one smooth surface with a flexible pattern. In another aspect, the interbody 100 has a least one surface with a flexible pattern and a plurality of projections. In another aspect, the interbody has at least one surface with a plurality of projections.

In an aspect, the interbody 100 can be symmetric. For example, the interbody 100 can be symmetric with respect to two surfaces each with a flexible pattern 200, e.g., can have the exact same surface and flexible pattern 200 opposite one another, such as a top surface 112a with a flexible pattern 200 that is exactly the same in all variables as a bottom surface 112b with a flexible pattern 200.

In another aspect, the interbody 100 can be asymmetric. For example, the interbody 100 can be asymmetric with respect to two surfaces with a flexible pattern 200, e.g., can have a different surface with a flexible pattern 200 opposite one another, such as a top surface 112a that is different with respect to one variable as a bottom surface 112b.

In an aspect, the interbody 100 can include at least one surface and at least one post 106. For example, the at least one post 106 can be positioned under a center of the interior of the at least one surface, as shown in FIGS. 11B and 11C. As a further example, the interbody 100 can include at least one surface 112a and at least one non-flexible surface 112b that are separated from one another by four posts 106 at a corner of each surface, as shown in FIGS. 11A-11C. The non-flexible surface can be smooth or can include a plurality of grooves. In another aspect, the interbody 100 can include any number of posts 106, such as two posts, three posts, four posts, etc. The posts 106 can be located anywhere within the interbody, such as anywhere between surfaces 112a, and 112b, such as along the perimeter and/or within the interior.

The interbody 100 can include at least one surface having a radius of curvature forming a curved surface. The curved surface can be a smooth surface or a surface having an array of projections 122. The curved surface can also be at least one surface with a flexible pattern 200. The curved surface can have a radius of curvature defining a convex surface. The curved surface can have a radius of curvature defining a concave surface. If the interbody 100 includes two or more curved surfaces, each curved surface may be the same or different. For example, the radius of curvature can be the same or different for each curved surface.

In another aspect, the interbody 100 can be distractible. Distractible interbodies are described in the following U.S. patents, the entirety of their disclosures are hereby incorporated by reference: U.S. Pat. Nos. 8,303,663; 8,932,302; 8,636,746; 8,771,360; 9,358,125; 9,474,626; and 9,498,270.

The interbody 100 can be filled with a bone support matrix. As used herein, a "bone support matrix" is a material that facilitates osteogenesis. Suitable bone support matrices can be resorbable or nonresorbable and osteoconductive or osteoinductive. Non-limiting examples of suitable bone support matrices include synthetic materials, bone morphogenic proteins (BMPs), and heterologous, homologous, or autologous bone and derivatives thereof. The bone support matrix may be radiolucent on x-rays.

In another aspect, the flexible interbody 100 is included in a method of placing an implant between vertebrae in a spine.

Through the inclusion of a flexible pattern on an interbody, engagement of the interbody with adjacent vertebrae is improved. In particular, surfaces of the interbody deform to adapt to the contours of the bone surfaces so that a close fit is obtained.

Fixation Member

In another aspect, the present disclosure is directed to a fixation member 300, including a head 312, and at least one surface with a flexible pattern 400, wherein the flexible pattern includes a continuous line of material. The flexibility of a surface can be determined by various techniques including determining the stiffness of a surface, i.e., the resistance of a surface to elastic deformation. Stiffness is a measure of the applied force divided by the deflection of the surface. Variables associated with the flexible pattern can alter the stiffness of the surface. By selecting certain variables, a specific stiffness can be achieved in response to a given load. The flexible pattern can provide a stiffness to a surface that can be measured, for example, using a compressive load. The stiffness of a surface including a flexible pattern relative to another surface without the flexible pattern can vary from about 25% to about 100%, for example, from about 35% to about 90%, and as a further example from about 50% to about 80%.

Figure 19A:
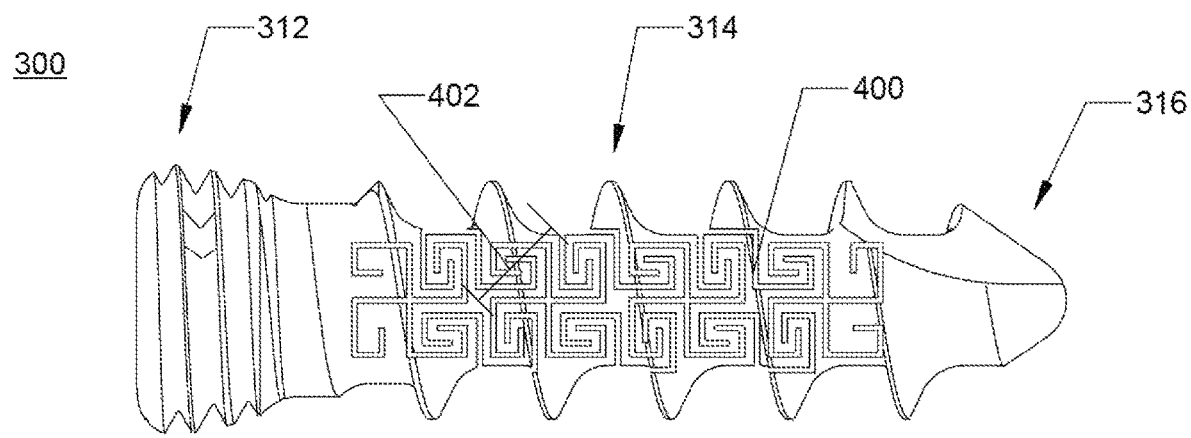
FIGS. 19A-B are front views of a fixation member in different states of flexure according to one embodiment of the disclosure.
Figure 19B:
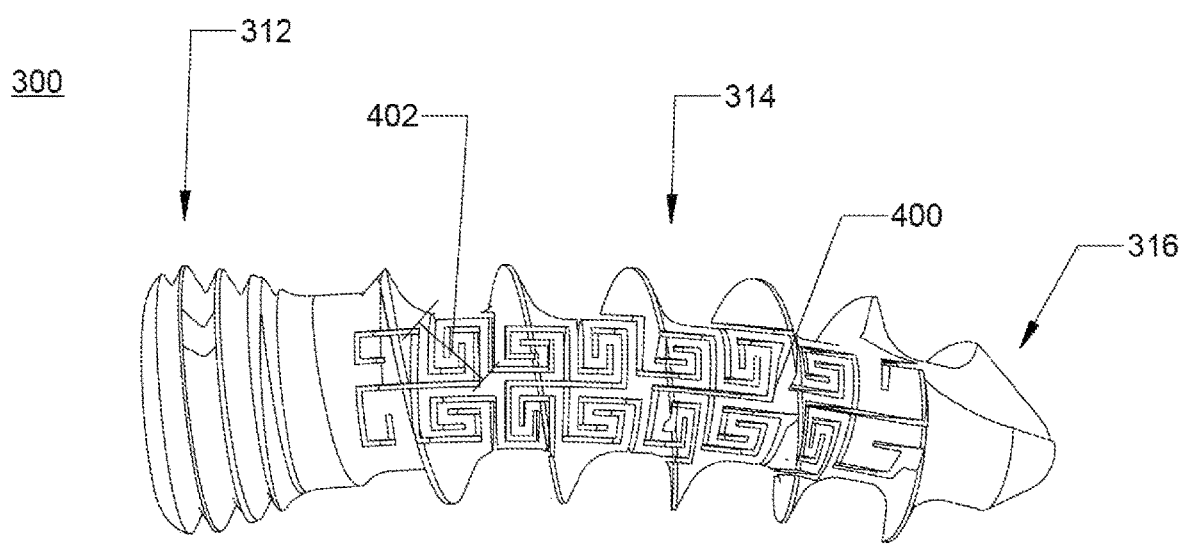
Figure 19C:
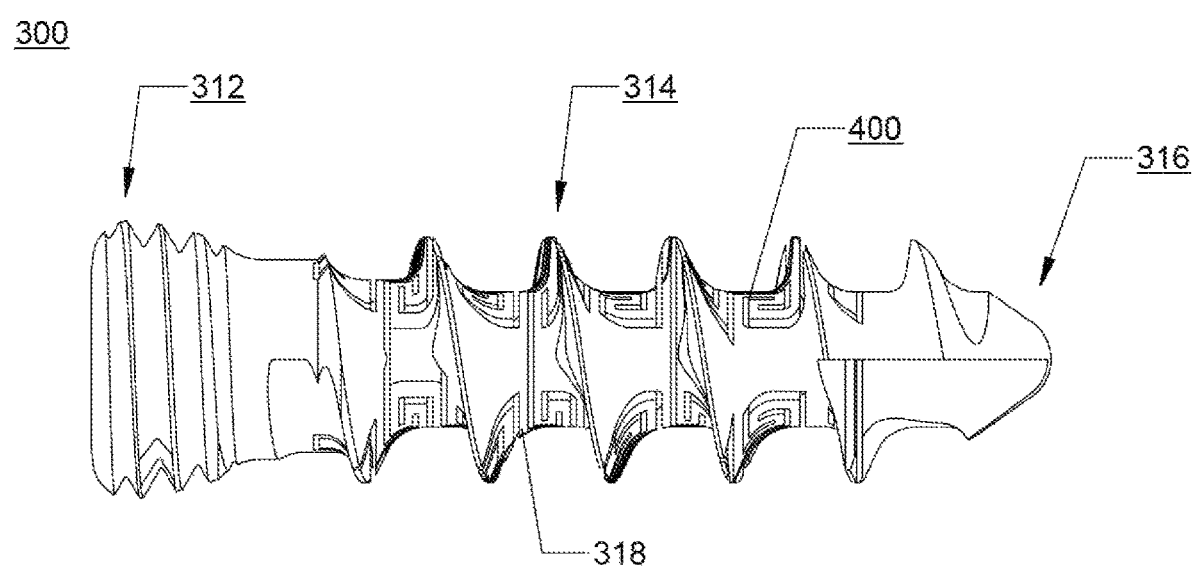
FIG. 19C is a side view of the fixation member of FIGS. 19A-B.

As shown in FIGS. 19A, 19B, and 19C, the head 312 of the fixation member 300 can be any shape, such as cylindrical, cupped, squared, polygonal, etc., so long as it can be used to manipulate the fixation member 300 into an osseous tissue. The head 312 can include an exterior helical thread with surfaces that can engage with osseous tissue. Alternatively, the head 312 can include a smooth surface. In another aspect, the head 312 can include an outer roughened surface to enhance the grip of a user and/or attachment of a screw assembly (not shown). Additionally, the head 312 may be configured and dimensioned, such as including a multi-faceted inner surface or can be keyed, to receive a driver (not shown).

The head 312 can extend from a proximal end of the fixation member 300 into a body 314. The body 314 can extend from the head 312 to a distal end 316 of the fixation member 300. In an aspect, the body 314 can include a consistent diameter throughout a length of the body. In another aspect, the body 314 can taper from the head 312 to the distal end 316 of the fixation member 300. The body 314 of the fixation member 10 can include an exterior helical thread with surfaces that can engage with osseous tissue. The exterior helical thread of the body 314 may be same or different from the exterior helical thread of the head 312. For example, the exterior helical thread of the head 312 may form a tighter, denser helix as compared to the exterior helical thread of the body 314 or vice versa. Alternatively, the body 314 can include a smooth surface.

The body 314 of the fixation member 300 can include a surface with a flexible pattern 400. The flexible pattern 400 can extend at least a quarter of a length of the fixation member 300. In another aspect, the flexible pattern 400 can extend at least a half of a length of the fixation member 300. The fixation member 300 can be configured and dimensioned to bend and/or flex when under stress, such as an applied force.

The distal end 316 of the fixation member 300 can have a blunt end or a pointed end. The distal end 316 can also include any exterior helical thread that extends from the body 314. In another aspect, the distal end 316 can include a non-flexible surface, e.g., a surface absent the flexible pattern 400.

The fixation member 300 can include at least one surface with a flexible pattern 400, in which the flexible pattern 400 includes a continuous line of material.

The fixation member 300 may be varied in many ways. As shown in FIG. 19C, the flexible pattern 400 can be present on the body 314 with a non-flexible surface 318. In another aspect, the flexible pattern 400 can be present on the entire body 314 without a non-flexible surface 318.

The flexible pattern of material on the fixation member may be varied in many ways, such as those shown in FIGS. 2A, 2B, 3A, 3B, 4A, and 4B. In these variations, the flexible pattern of fixation member 300 shown in FIGS. 19A-C may be substituted with flexible pattern 200 shown in any one of FIGS. 2A, 2B, 3A, 3B, 4A and 4B. The flexible patterns 200 can include a continuous line of material. As shown in FIGS. 2A, 2B, 3A, 3B, 4A, and 4B, the shaded area is the continuous line of material forming the flexible pattern 200. The white area is the absence of material. The flexible pattern 200 can include a plurality of segments 202 that interconnect to form rows and columns. A segment 202 can include a first end and a second end in which the first end of each segment 202 can interconnect with at least one second end of another segment 202 of the plurality of segments 202, for example in an adjacent row or column. In an aspect, a first end of a segment 202 can interconnect with three different segments to form the flexible pattern 200 with a continuous line of material. In a further aspect, a second end of a segment 202 can interconnect with three different segments to form the flexible pattern 200 with a continuous line of material.

In another aspect as shown in FIG. 5A, the segment 202 can flip orientations within the continuous line of material so that in a first configuration the segment 202 forms rows and in an adjacent second configuration the segment 202 forms columns. The flexible pattern can also increase in size. For example, as shown in FIG. 5A, the innermost columns and rows are smaller in size than the outermost columns and rows. Accordingly, the stiffness in the interior of the flexible pattern 200 is expected to be lower than a stiffness along the outer edges, e.g., perimeter, of the flexible pattern 200.

As shown in FIGS. 2A, 2B, and 5A, the flexible pattern 200 can include a continuous line of material that forms corners, which can be used to form smaller or denser patterns. A flexible pattern 200 with corners can be harder to manufacture. As shown in FIGS. 3A, 3B, 4A, and 4B, the flexible pattern 200 can comprise curves, arches, and/or curlicues, which can be used to form larger or less dense patterns. A flexible pattern 200 with curves, arches, and/or curlicues can be easier to manufacture.

The continuous line of material can be any biocompatible material, such as a metal, an alloy, a polymer, and combinations thereof, such as a blend of a metal and a polymer. The continuous line of material can have a uniform width. In an aspect, a width of the continuous line of material can vary. In an aspect, the continuous line of material can include straight areas and/or curved areas.

In further variations, the flexible pattern may also be as shown in FIGS. 6-10 and described above. The cut outs of the flexible pattern may all be perpendicular to a surface with the flexible pattern, some may be at an acute angle relative to the surface, or the cut outs may be any combination of orientations as described above. Further, the cut outs may be partially or entirely through a thickness of the structure, such as an outer wall structure, as described above.

The flexible pattern 400 can flex under application of a force or stress. In an aspect, a first area of the flexible pattern 400 can move in a direction relative to a second area of the flexible pattern 400 under an applied force, as shown in FIG. 19B. The distal end of the flexible pattern 400 in the body 314 moves in a direction away from the proximal end of the flexible pattern 400 in the body 314.

The fixation member 300 can be formed by known manufacturing methods, such as additive layer manufacturing, e.g., three-dimensional printing, chemical etching, photo etching, laser cutting, water jet cutting, and traditional machining, etc. Additive layer manufacturing may be performed in any of the ways described above, for example.

The flexible pattern 400 can be the same or different and/or can be present or absent across the at least one surface of the fixation member 300. In an aspect, the flexible pattern 400 can be present across the entire surface or can be present in sections, as shown in FIG. 19C (i.e., can include a non-flexible surface 318) of the at least one surface.

The flexible pattern 400 can transition from a less dense, i.e., farther apart, pattern at a proximal end of the body 314 to a denser, i.e., closer together, pattern at a distal end of the body 314. The transition of the flexible pattern 400 along a length of the body 314 can be equivalent from a proximal end to a distal end of the body 314 and vice versa. The transition of the flexible pattern 400 can also be graduated so that there are gradient zones of varying flexibility across the body 314 of the fixation member 300.

A method of using the fixation member 300 includes, forming an insertion hole in osseous tissue, such as a vertebra. For example, a user can use a drill or probe to form the insertion hole. Alternatively, a user can probe the osseous tissue using the fixation member 300 itself using a driver (not shown). The fixation member 300 can be inserted into the insertion hole. In an aspect, the fixation member 300 can be inserted into the insertion hole until the head 312 is within the vertebra. A user can then affix a driver (not shown) into the head 312 of the fixation member 300 and apply a force to the driver. The applied force can rotate the fixation member 300 about its longitudinal axis so that the exterior helical threads of the body 314 and/or the head 312 engage with the osseous tissue. If the fixation member 300 experiences stress, for example, by the distal end 316 abutting the osseous tissue, the fixation member 300 will flex/bend under the force, as shown in FIG. 19B, and will not breach the osseous tissue. A user can apply an opposite force to disengage the exterior helical threads to adjust placement of the fixation member 300 or to remove it completely.

Through the inclusion of a flexible pattern on a fixation member, the fixation member is advantageous as it provides a greater number of possibilities for an insertion angle and ultimately reduces the size of incision required to implant the fixation member.

Flexible Instrument

In one aspect, the present disclosure is directed to a flexible instrument 500 comprising at least one surface with a flexible pattern 600, wherein the flexible pattern 600 includes a continuous line of material. The flexible instrument 500 can be any instrument with the at least one surface with a flexible pattern 600, such as a retractor blade. The flexibility of a surface can be determined by various techniques including determining the stiffness of a surface, i.e., the resistance of a surface to elastic deformation. Stiffness is a measure of the applied force divided by the deflection of the surface. Variables associated with the flexible pattern 600 can alter the stiffness of the surface. By selecting certain variables, a specific stiffness can be achieved in response to a given load. The flexible pattern 600 can provide a stiffness to a surface that can be measured, for example, using a compressive load. The stiffness of a surface including a flexible pattern 600 relative to another surface without the flexible pattern can vary from about 25% to about 100%, for example, from about 35% to about 90%, and as a further example from about 50% to about 80%.

Figure 20A:
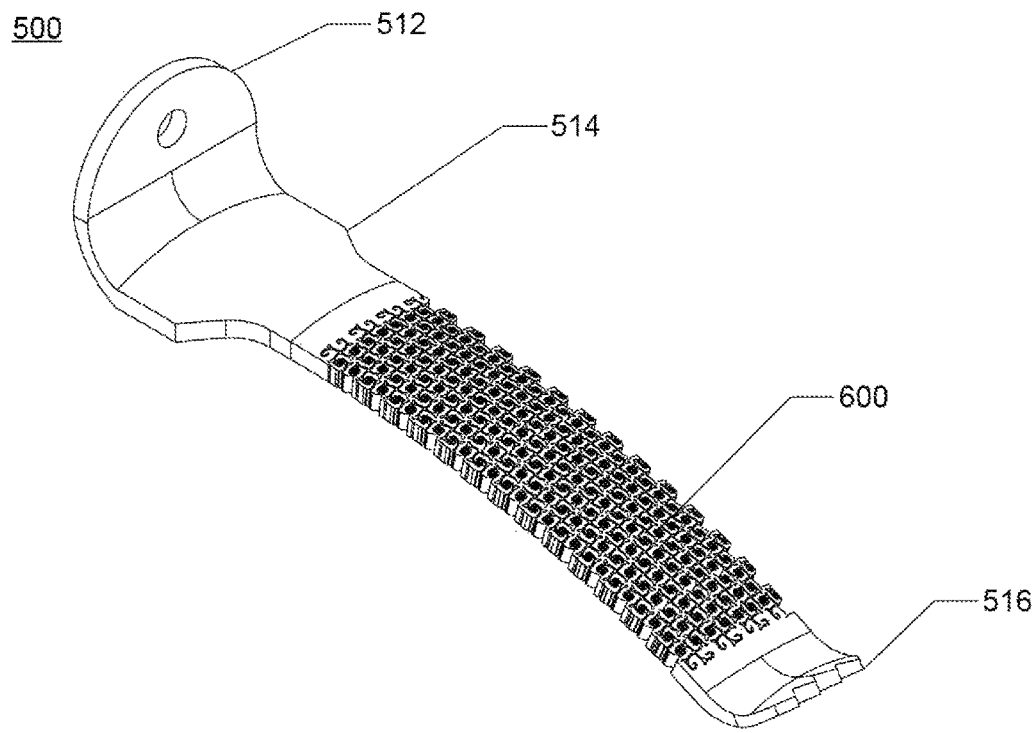
FIGS. 20A-B are isometric and front views, respectively, of a flexible instrument according to one embodiment of the disclosure.
Figure 20B:
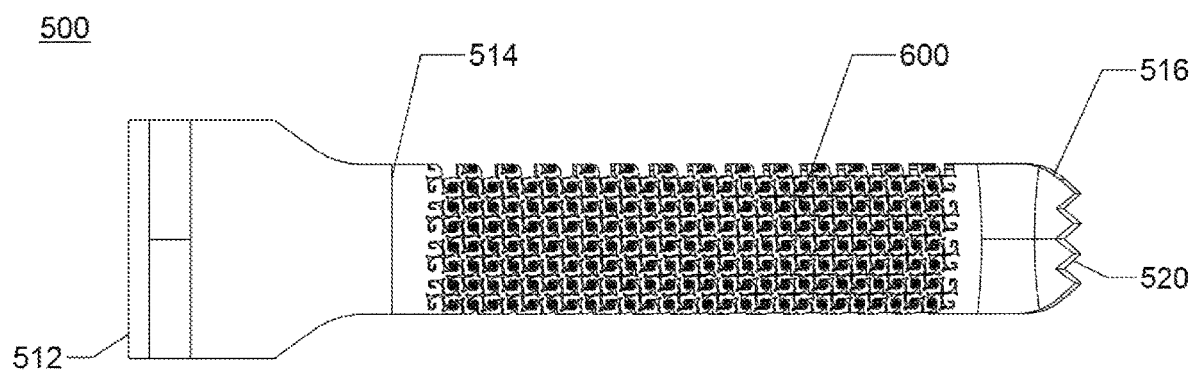
Figure 20C:
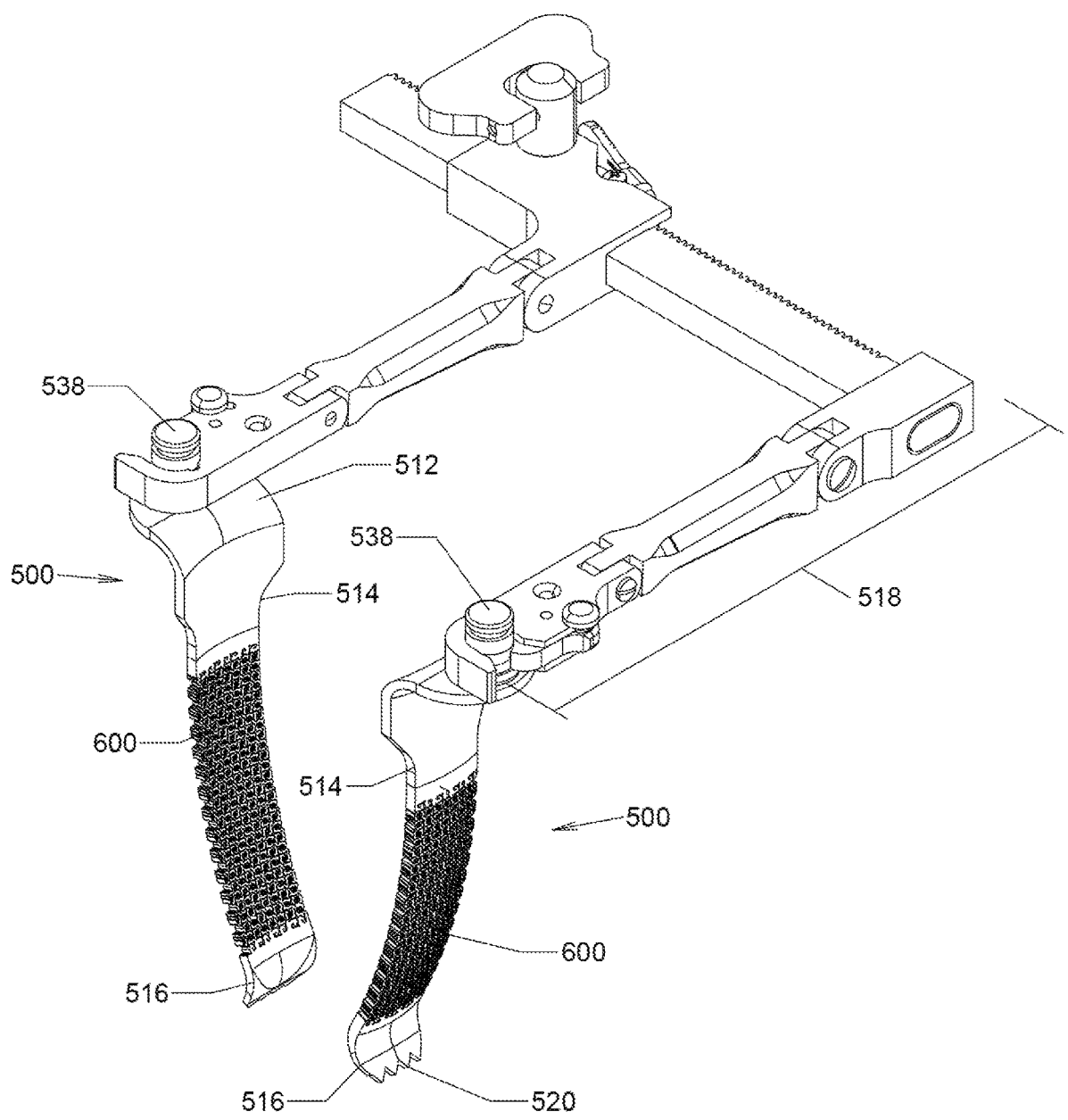
FIG. 20C is a perspective view of the flexible instrument of FIGS. 20A-B in a retraction system according to one embodiment of the disclosure.

The flexible instrument 500 can include an arm 512, and an elongated portion 514, as shown in FIGS. 20A-20C. The arm 512 can be configured and dimensioned to engage with a retraction system 518, as shown in FIG. 20C. The arm 512 can include a connecting pin 538, as shown in FIG. 20C, which can enable connection with the retraction system 518.

The elongated portion 514 can extend from the arm 512. The elongated portion 514 can include any height and width so long as the elongated portion 514 does not inhibit a view of a surgical field. In an aspect, the height and width of the elongated portion 514 should be configured and dimensioned to improve retraction of tissue in a surgical field.

In an aspect, the elongated portion 514 can include a distal end 516. The distal end 516 can include a curved surface. In an aspect, the curved surface of the distal end 516 can be configured and dimensioned to engage with tissue. For example, the distal end 516 can include a plurality of teeth 520.

The elongated portion 514 of the flexible instrument 500 can have at least one surface including a flexible pattern 600. In an aspect, the flexible pattern 600 can be present across the entire surface of the elongated portion 514, as shown in FIGS. 20A-20C, and in FIG. 12A for flexible pattern 200, or can be present in sections. For example, the extent of the flexible pattern for flexible instrument 500 shown in FIGS. 20A-C may be substituted with flexible pattern 200 shown in any one of FIGS. 12B-12D. In this manner, the elongated portion 514 can include a section of the surface of the elongated portion 514 with a flexible pattern 200, and can include a non-flexible surface 118, i.e., a surface of the elongated portion 14 without a flexible pattern 200, as shown in FIGS. 12B-12D. The non-flexible surface 118 of the elongated portion 514 can provide stability to the flexible instrument 500 and can influence the direction of flexibility of the flexible instrument 500.

The flexible pattern 600 can extend at least a quarter of a length of the elongated portion 514. In another aspect, the flexible pattern 600 can extend at least a half of a length of the elongated portion 514. In an aspect, the flexible pattern 600 can extend an entire length of the elongated portion 514, such as from the arm 512 to the distal end 516. The flexible instrument 500 can be configured and dimensioned to bend and/or flex when under stress, such as an applied force.

In an aspect, the flexible instrument 500 can include an elongated portion 514 with a non-flexible surface 518 that extends up to 25% of a length of the elongated portion 514 and the remainder of the length (75%) of the elongated portion 514 can include the flexible pattern 600.

In another aspect not shown, the flexible instrument 500 can include an elongated portion 514 with a flexible pattern 600 near the arm 512 and the distal end 516, and a non-flexible surface in between the flexible pattern 600. In a further aspect, the flexible instrument 500 can include an elongated portion 514 with a non-flexible surface 518 near the arm 512 and the distal end 516, and a flexible pattern 600 in between the non-flexible surface 518 areas, as shown in FIGS. 20A-C, for example.

The flexible pattern of material on the flexible instrument may be varied in many ways, such as those shown in FIGS. 2A, 2B, 3A, 3B, 4A, and 4B. In these variations, the flexible pattern of flexible instrument 500 shown in FIGS. 20A-C may be substituted with flexible pattern 200 shown in any one of FIGS. 2A, 2B, 3A, 3B, 4A and 4B. Thus, the flexible instrument 500 can include a surface with a flexible pattern 600, in which the flexible pattern 600 includes a continuous line of material, as shown in FIGS. 2A, 2B, 3A, 3B, 4A, and 4B. As shown in FIGS. 2A, 2B, 3A, 3B, 4A, and 4B, the shaded area is the continuous line of material forming the flexible pattern 200. The white area is the absence of material. The continuous line of material can include a plurality of segments 202 that interconnect to form rows and columns. A segment 202 can include a first end and a second end in which the first end of each segment 202 can interconnect with at least one second end of another segment 202 of the plurality of segments 202, for example in an adjacent row or column. In an aspect, a first end of a segment 202 can interconnect with three different segments to form the continuous line of material. In a further aspect, a second end of a segment 202 can interconnect with three different segments to form the flexible pattern 200 with a continuous line of material.

In another aspect as shown in FIG. 5A, the segment 202 can flip orientations within the continuous line of material so that in a first configuration the segment 202 forms rows and in an adjacent second configuration the segment 202 forms columns. The flexible pattern 200 can also increase in size. For example, as shown in FIG. 5A, the innermost columns and rows are smaller in size than the outermost columns and rows. Accordingly, the stiffness in the interior of the flexible pattern 200 is expected to be lower than a stiffness along the outer edges, e.g., perimeter, of the flexible pattern 200.

Also shown in FIGS. 2A, 2B, and 5A, the flexible pattern 200 can include a continuous line of material that forms corners, which can be used to form smaller or denser patterns. A flexible pattern 200 with corners can be harder to manufacture. As shown in FIGS. 3A, 3B, 4A, 4B, and 5C, the flexible pattern 200 can comprise curves, arches, and/or curlicues, which can be used to form larger or less dense patterns. A flexible pattern 200 with curves, arches, and/or curlicues can be easier to manufacture.

The continuous line of material can be any biocompatible material, such as a metal, an alloy, a polymer, and combinations thereof, such as a blend of a metal and a polymer. The continuous line of material can have a uniform width. In an aspect, a width of the continuous line of material can vary. In an aspect, the continuous line of material can include straight areas and/or curved areas.

In further variations, the flexible pattern may also be as shown in FIGS. 6-10 and described above. The material cut outs of the flexible pattern may all be perpendicular to a surface with the flexible pattern, some may be at an acute angle relative to the surface, or the cut outs may be any combination of orientations as described above. Further, the cut outs may be partially or entirely through a thickness of the structure, such as an outer wall structure, as described above.

The flexible instrument 500 can be formed by known manufacturing methods, such as additive layer manufacturing, e.g., three-dimensional printing, chemical etching, photo etching, laser cutting, water jet cutting, and traditional machining, etc. Additive layer manufacturing may be performed in any of the ways described above, for example.

The flexible pattern 600 can transition from a less dense, i.e., farther apart, pattern near the arm 512 of the elongated portion 514 to a denser, i.e., closer together, pattern at a distal end 516 of the elongated portion 514. The transition of the flexible pattern 600 along a length of the elongated portion 514 can be equivalent from near the arm 512 to a distal end 16 and vice versa. The transition of the flexible pattern 600 can also be graduated so that there are gradient zones of varying flexibility along a length of the elongated portion 514 of the flexible instrument 500.

As shown in FIGS. 12A-12D, the flexible pattern 600, shown as flexible pattern 200, as noted above, can be the same or different and/or can be present or absent across the at least one surface of the flexible instrument 500. In an aspect, the flexible pattern 200 can be present across the entire surface, as shown in FIG. 12A, or can be present in sections (i.e., can be absent in sections) of the at least surface, such as shown in FIGS. 12B-12D. In another aspect, the flexible pattern 200 can be present in a section to form a perimeter 206 of the at least one surface without being present at an interior of the at least one surface, as shown FIG. 12C. The flexible pattern 200 can also be present in an interior 208, without extending to one or more edges, to form a center of the at least one surface, as shown in FIGS. 12B and 12D.

The flexible pattern 600 can transition from a perimeter to an interior so that the perimeter is more flexible than the interior and vice versa. For example, the flexible pattern 600 can transition from a less dense, i.e., farther apart, pattern at a perimeter to a denser, i.e., closer together, pattern at an interior of the at least one surface. As a further example, the flexible pattern 600 can transition from a denser, i.e., closer together, pattern at a perimeter to a less dense, i.e., farther apart, pattern at an interior of the at least one surface. The transition of the flexible pattern 600 can be equivalent from a perimeter to an interior and vice versa. The transition of the flexible pattern 600 can be graduated so that there are gradient zones of varying flexibility across the at least one surface.

The at least one surface can include alternating sections. For example, a first section of the at least one surface can be more rigid. A second section can be adjacent to the first section and can be more flexible. The number of alternating rigid and flexible sections can vary. The at least one surface can be more rigid depending upon variables, such as the density of the pattern and/or the thickness of the material used to form the pattern. Similarly, the at least one surface can be more flexible with, for example, a less dense pattern and/or a thinner material used to form the pattern. In another aspect, the at least one surface can include an alternating section of a first section with a flexible pattern 600 and a second section with a non-flexible surface 118.

The at least one surface can have a uniform thickness, such as shown in the elongated portion 514 in FIG. 20C. In another aspect, the at least one surface can have a thickness that varies. The thickness can vary by sections. For example, the at least one surface can have a first section that is thin adjacent to a second section that is thick (compared to the first section). The thin/thick sections can alternate across the at least one surface and can affect the flexibility of the at least one surface. In another aspect, the thickness can vary along a gradient of the at least one surface, such as from thick to thin or vice versa. It is expected that a section of the at least one surface that is thicker than another section will also be more rigid. Similarly, it is expected that a section of the at least one surface that is thinner than another section will also be more flexible, as shown in FIGS. 16A-C and FIGS. 17A-C, where like reference numerals in the 100 and 200 series refer to like elements in the 500 and 600 series of numerals, respectively, and 162 refers to a surface.

In particular, FIGS. 16A-C illustrate the side view of, for example, a surface 162 having a flexible pattern 200, as shown in FIGS. 17A-C, respectively. FIG. 16A illustrates a surface 162 that is thicker than a surface as shown in FIG. 16B, which is thicker than a surface as shown in FIG. 16C.

FIGS. 16A-C and FIGS. 17A-C illustrate that a thin surface with a flexible pattern 200 (see, e.g., FIGS. 16C and 17C) can have a greater degree of flexibility as compared to a thicker surface with a flexible pattern 200 (see, e.g., FIGS. 16A and 17A).

In another aspect, flexible instrument 500 may be used in a method of retraction to create or modify a portal to a surgical site within a patient. Increased flexural properties on customized areas of the instrument provide a final retracted space for use in access to the surgical site that is closer to a desired size than would be possible without the flexural properties provided by the flexible regions.

One reason flexible instrument 500 is advantageous is that the inclusion of a flexible pattern surface provides the instrument with increased versatility, reducing surgical steps requiring both hands of a surgeon and otherwise minimizing a size of incision required for use of the instrument.

Flexible Rod

In one aspect, the present disclosure is directed to rod 700 including a first end 712, a second end 716, and a body 714 with a flexible pattern 800, wherein the flexible pattern 800 includes a continuous line of material. The flexibility of a surface can be determined by various techniques including determining the stiffness of a surface, i.e., the resistance of a surface to elastic deformation. Stiffness is a measure of the applied force divided by the deflection of the surface. Variables associated with the flexible pattern can alter the stiffness of the surface. By selecting certain variables, a specific stiffness can be achieved in response to a given load. The flexible pattern can provide a stiffness to a surface that can be measured, for example, using a compressive load. The stiffness of a surface including a flexible pattern relative to another surface without the flexible pattern can vary from about 25% to about 100%, for example, from about 35% to about 90%, and as a further example from about 50% to about 80%.

As shown in FIGS. 21A-21L, the rod 700 is an elongate member that extends from a first end 712 to a second end 716. The rod 700 includes a body 714 located between the first end 712 and the second end 716. Each of the first end 712 and the second end 16 may be independently configured and dimensioned, such as including a multi-faceted exterior surface, to receive a tool, driver, screw, etc. (not shown) to assist a user in manipulating, such as by flexing, the rod 700. The first end 712 and the second end 716 of the rod 700 can each independently have a blunt end or a pointed end. In another aspect, the first end 712 and the second end 716 can independently include a non-flexible surface, e.g., a surface absent the flexible pattern 800.

Figure 21A:
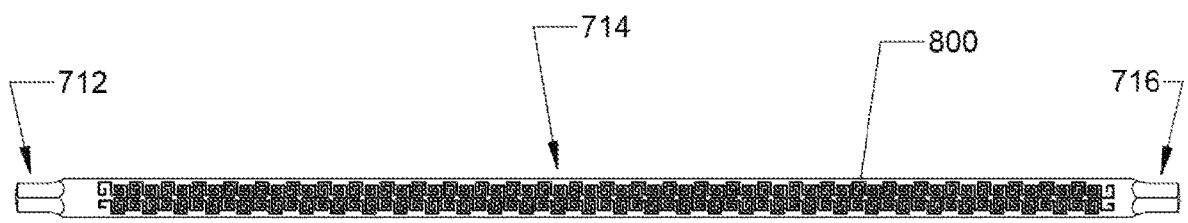
FIGS. 21A-D are views of a rod according to one embodiment of the disclosure.
Figure 21B:
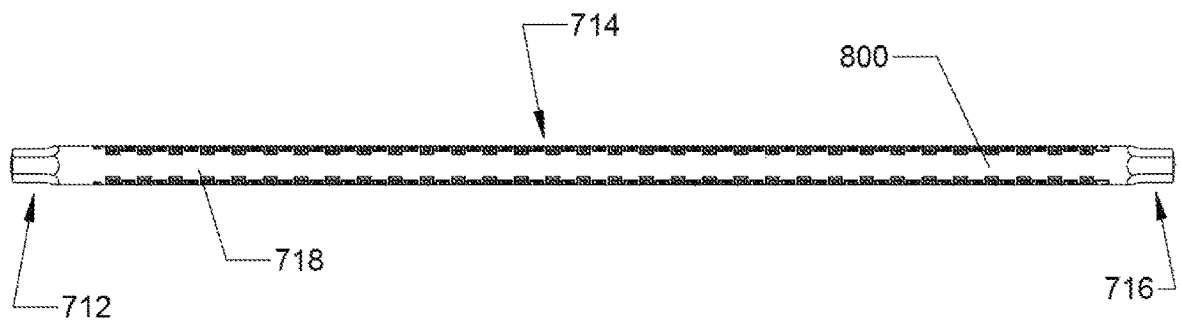

The rod 700 can have a body 714 with a surface including a flexible pattern 800. In an aspect, the flexible pattern 800 can be present across the entire surface of the body 714 or can be present in sections, as shown in FIGS. 21B-21L. For example, the body 714 can include a section of the surface of the body 714 with a flexible pattern 800, and can include a non-flexible surface 718, i.e., a surface of the body 714 without a flexible pattern 800. The non-flexible surface 718 of the body 714 can provide stability to the rod 700 and can influence the direction of flexibility of the rod 700. For example, as shown in FIG. 21D, the rod 700 can bend away from the non-flexible surface 718 of the body 714.

The flexible pattern 800 can extend at least a quarter of a length of the body 714. In another aspect, the flexible pattern 800 can extend at least a half of a length of the body 714, as shown in FIGS. 21E and 21F. In an aspect, the flexible pattern 800 can extend an entire length of the body 714, such as from the first end 712 to the second end 716, as shown in FIGS. 21A and 21B. The rod 700 can be configured and dimensioned to bend and/or flex when under stress, such as an applied force.

Figure 21C:
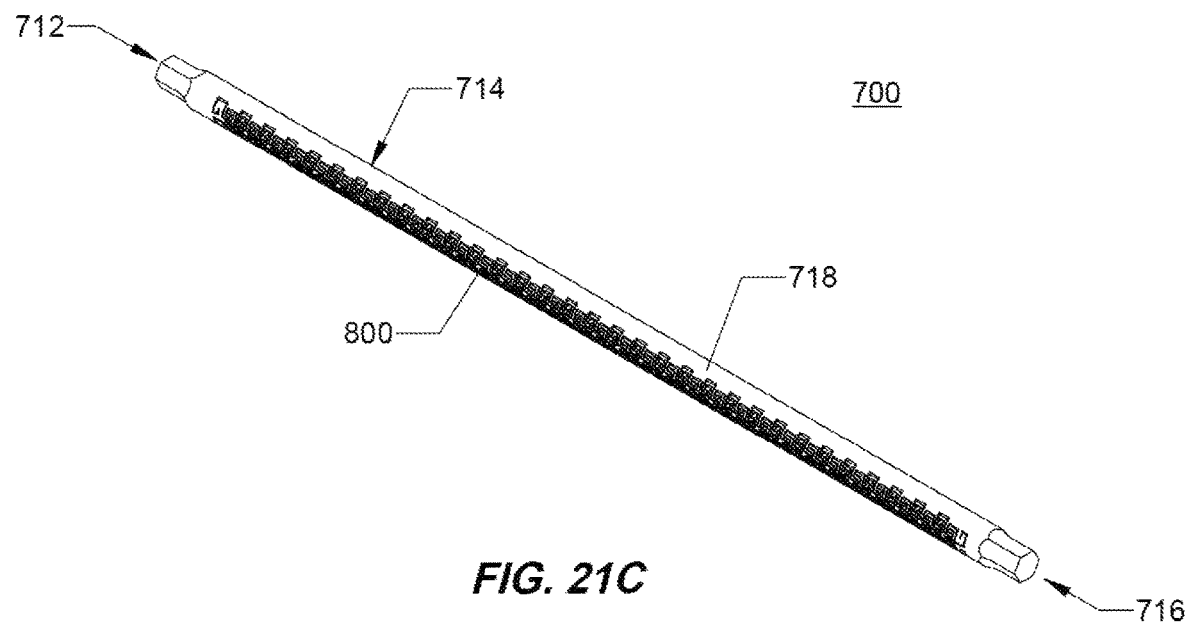
Figure 21D:
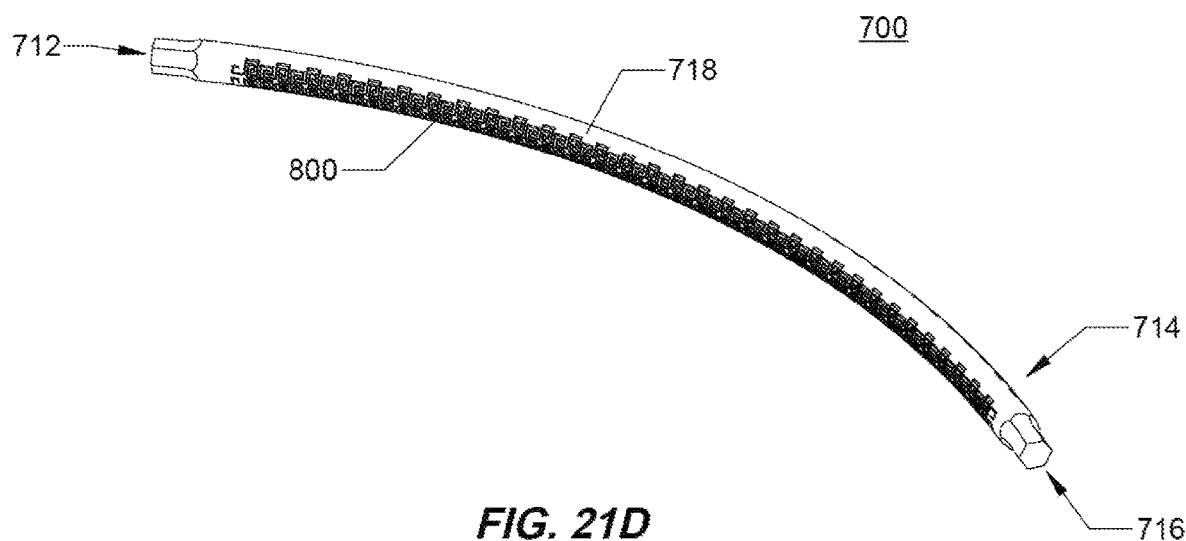
Figure 21E:
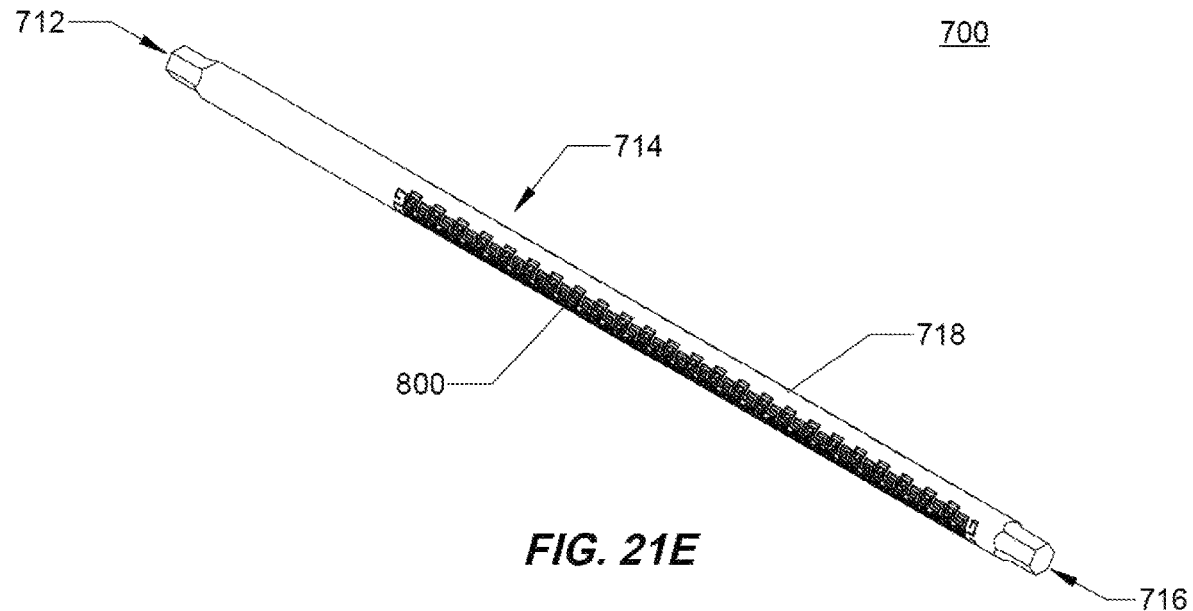
FIGS. 21E-F are isometric views of a rod according to one embodiment of the disclosure.
Figure 21F:
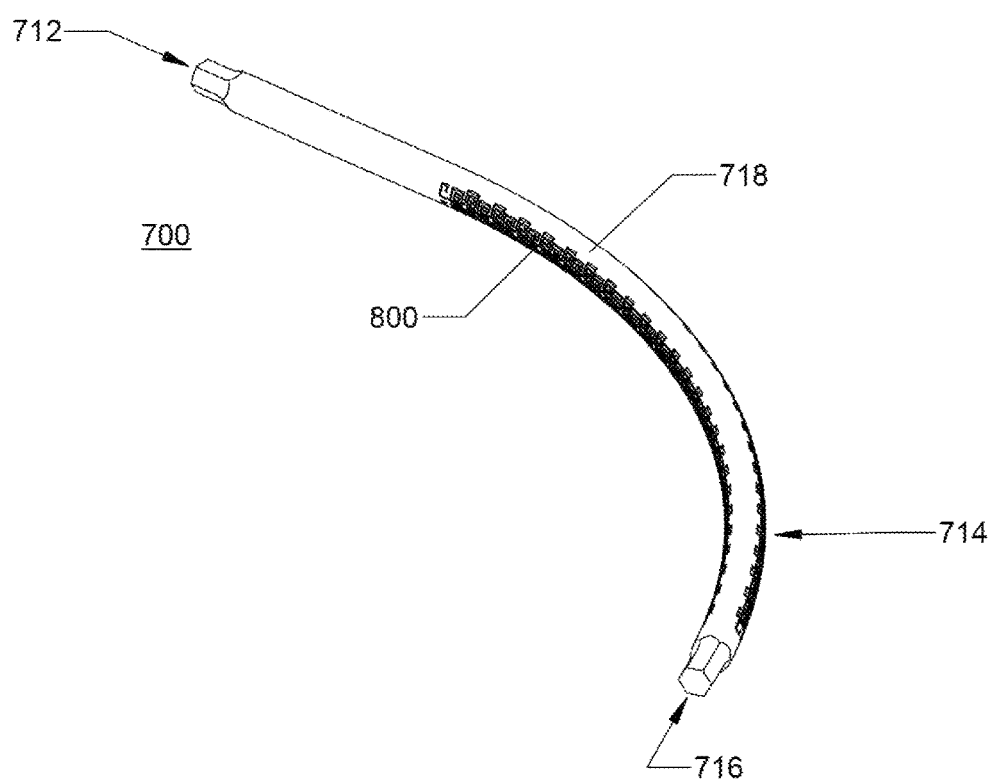
Figure 21G:
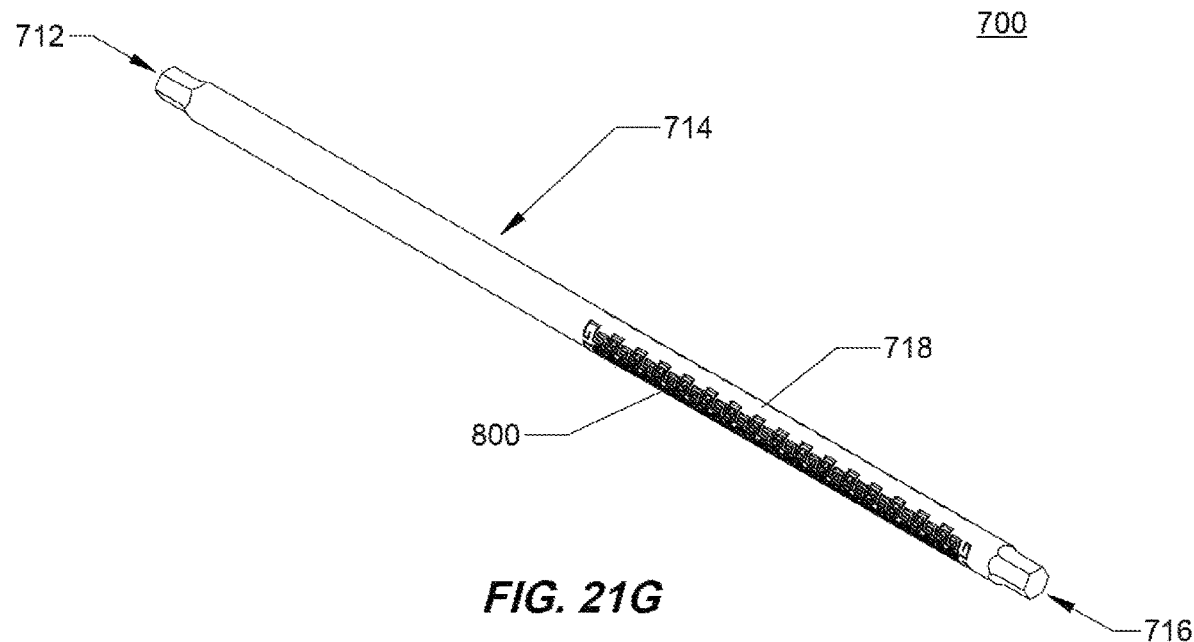
FIGS. 21G-H are isometric views of a rod according to one embodiment of the disclosure.
Figure 21H:
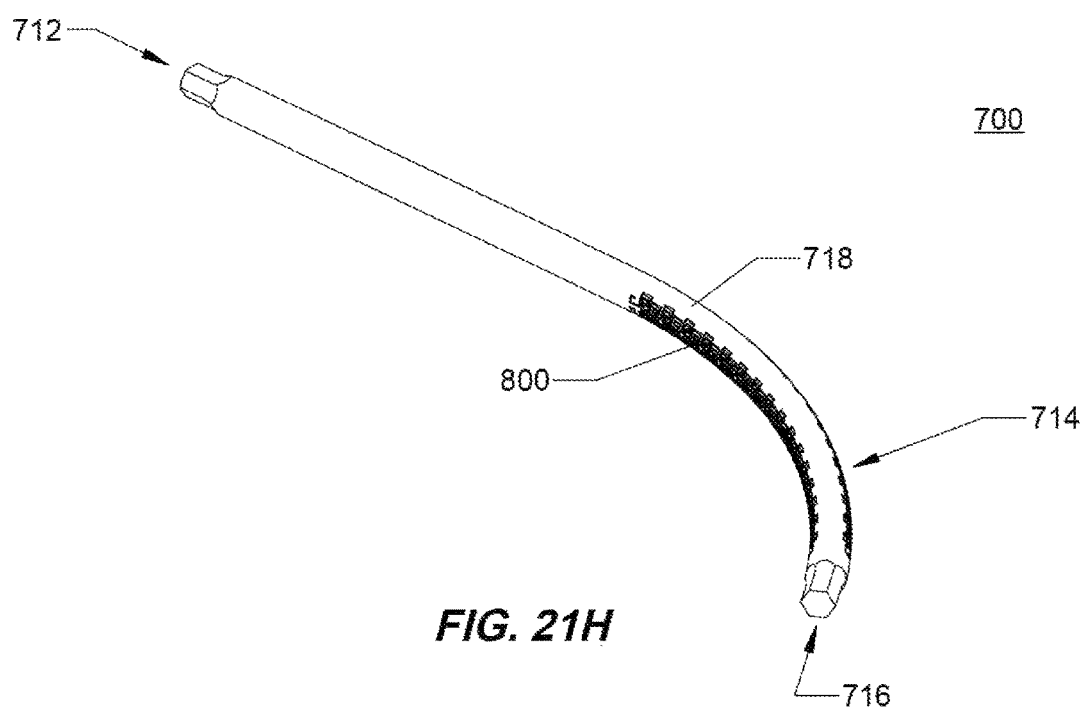

In an aspect, the rod 700 can include a body 714 with a non-flexible surface 718 that extends up to 25% of a length of the body 714 and the remainder of the length (75%) of the body 714 can include the flexible pattern 800, as shown in FIGS. 21G and 21H. The non-flexible surface 718 can provide strength when used in a diseased area of a spinal column. The transition in the rod 700 from a non-flexible surface 718 to a flexible pattern 800 can allow for a "softer" transition from instrumented levels to uninstrumented levels to reduce stress.

Figure 21I:
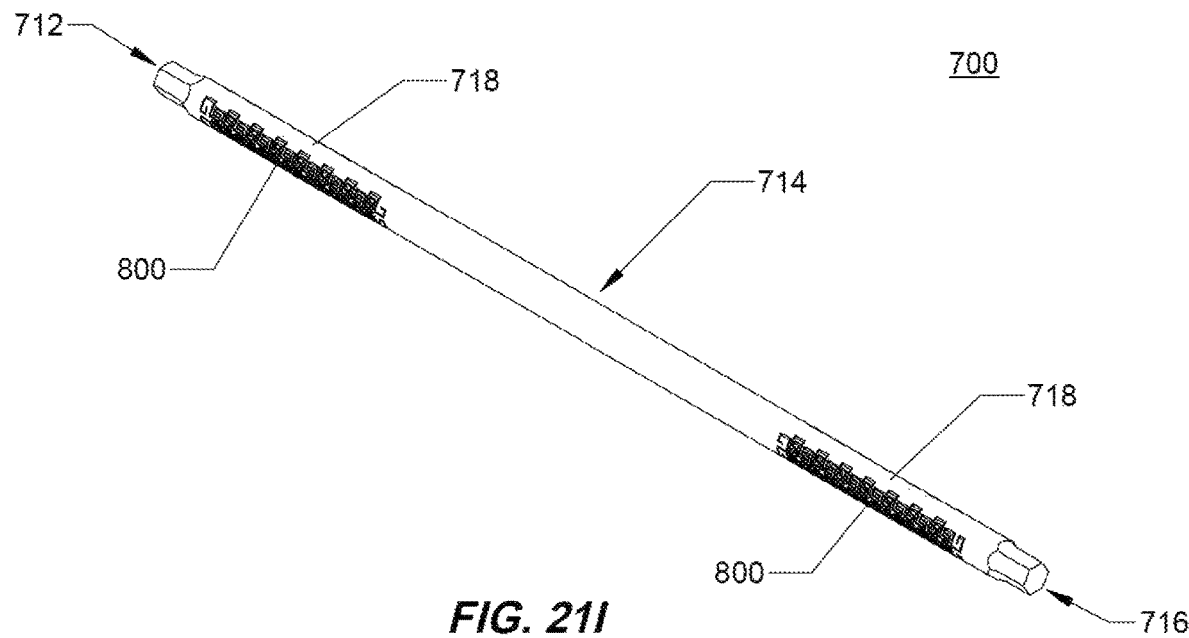
FIGS. 21I-J are isometric views of a rod according to one embodiment of the disclosure.
Figure 21J:
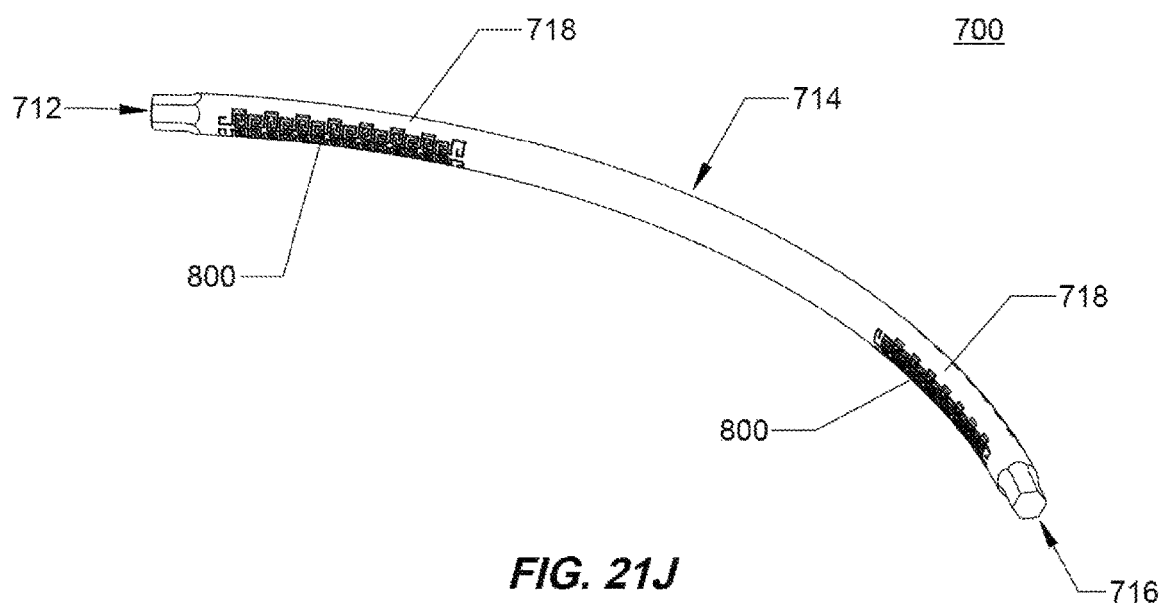
Figure 21K:
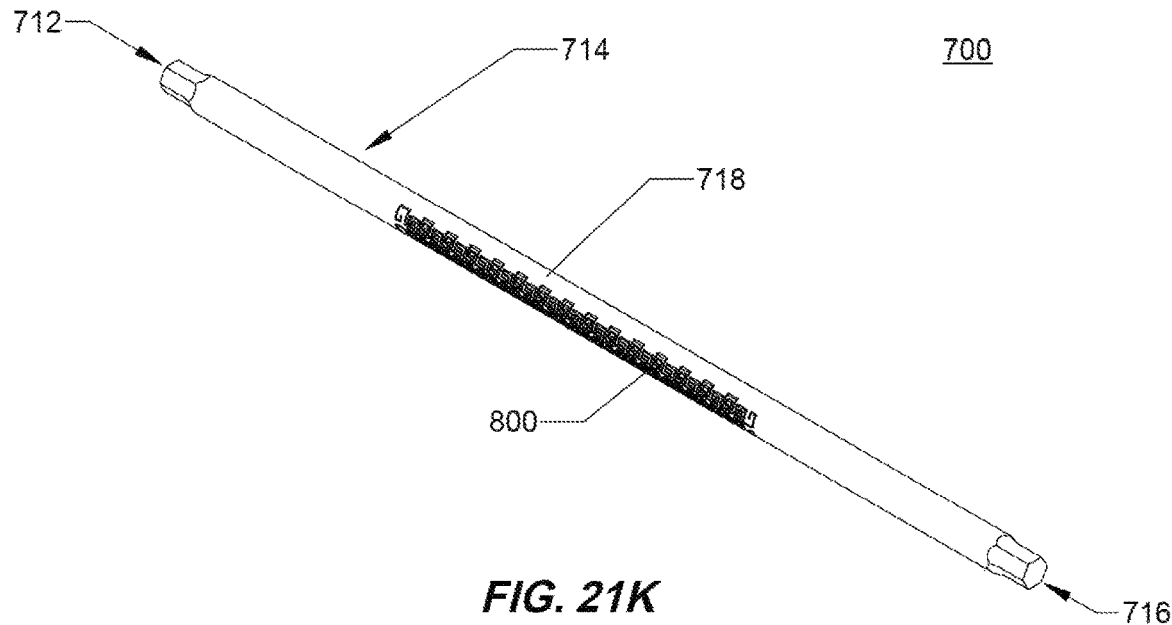
FIGS. 21K-L are isometric views of a rod according to one embodiment of the disclosure.
Figure 21L:
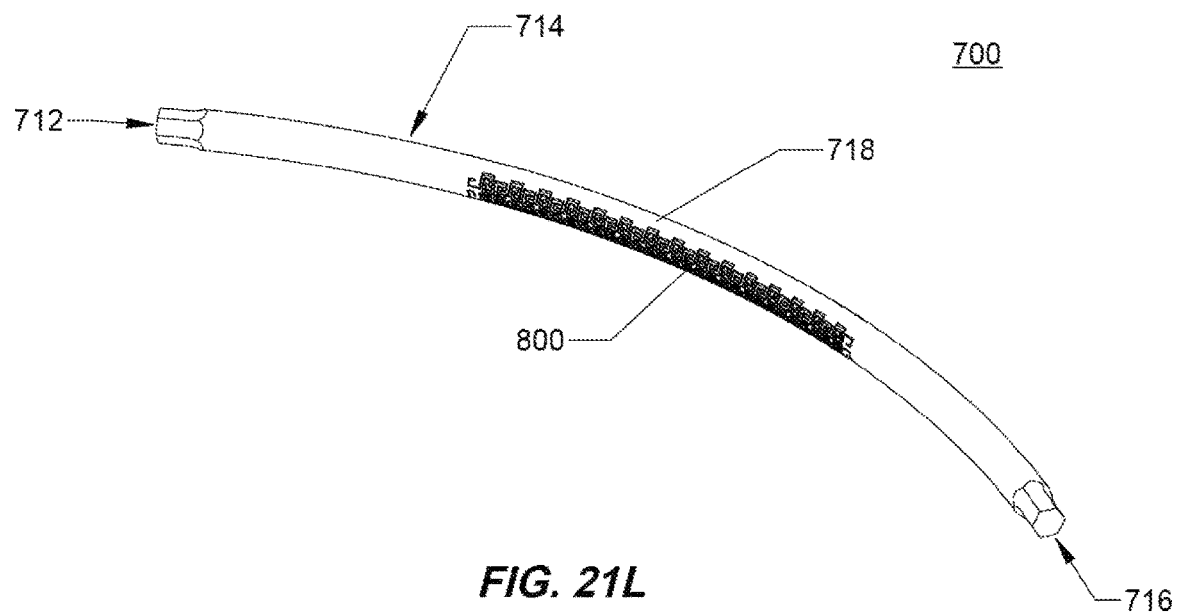

In another aspect, the rod 700 can include a body 714 with a flexible pattern 800 near the first end 712 and the second end 716, and a non-flexible surface 718 in between the flexible pattern 800, as shown in FIGS. 21I and 21J. In a further aspect, the rod 700 can include a body 714 with a non-flexible surface 718 near the first end 712 and the second end 716, and a flexible pattern 800 in between the non-flexible surface 718 areas, as shown in FIGS. 21K and 21L.

As shown in FIGS. 21B-21D, the flexible pattern 800 can be present on the body 714 with a non-flexible surface 718 that separates the flexible pattern 800 as it continues around the body 714. In another aspect, the flexible pattern 800 can be present on the entire body 714 without a non-flexible surface 718.

The rod 700 can include a surface with a flexible pattern 800, in which the flexible pattern 800 includes a continuous line of material, as shown in FIGS. 2A, 2B, 3A, 3B, 4A, and 4B. In these variations, the flexible pattern of rod 700 shown in FIGS. 21A-L may be substituted with flexible pattern 200 shown in any one of FIGS. 2A, 2B, 3A, 3B, 4A and 4B. As shown in FIGS. 2A, 2B, 3A, 3B, 4A, and 4B, the shaded area is the continuous line of material forming the flexible pattern 200. The white area is the absence of material. The continuous line of material can include a plurality of segments 202 that interconnect to form rows and columns. A segment 202 can include a first end and a second end in which the first end of each segment 202 can interconnect with at least one second end of another segment 202 of the plurality of segments 202, for example in an adjacent row or column. In an aspect, a first end of a segment 202 can interconnect with three different segments to form the continuous line of material. In a further aspect, a second end of a segment 202 can interconnect with three different segments to form the flexible pattern 200 with a continuous line of material.

In another aspect as shown in FIG. 5A, the segment 202 can flip orientations within the continuous line of material so that in a first configuration the segment 202 forms rows and in an adjacent second configuration the segment 202 forms columns. The flexible pattern can also increase in size. For example, as shown in FIG. 5A, the innermost columns and rows are smaller in size than the outermost columns and rows. Accordingly, the stiffness in the interior of the flexible pattern 200 is expected to be lower than a stiffness along the outer edges, e.g., perimeter, of the flexible pattern 200.

As shown in FIGS. 2A, 2B, and 5A, the flexible pattern 200 can include a continuous line of material that forms corners, which can be used to form smaller or denser patterns. A flexible pattern 200 with corners can be harder to manufacture. As shown in FIGS. 3A, 3B, 4A, 4B, and 5C, the flexible pattern 200 can comprise curves, arches, and/or curlicues, which can be used to form larger or less dense patterns. A flexible pattern 200 with curves, arches, and/or curlicues can be easier to manufacture.

The continuous line of material can be any biocompatible material, such as a metal, an alloy, a polymer, and combinations thereof, such as a blend of a metal and a polymer. The continuous line of material can have a uniform width. In an aspect, a width of the continuous line of material can vary. In an aspect, the continuous line of material can include straight areas and/or curved areas.

In further variations, the flexible pattern may also be as shown in FIGS. 6-10 and described above. The material cut outs of the flexible pattern may all be perpendicular to a surface with the flexible pattern, some may be at an acute angle relative to the surface, or the cut outs may be any combination of orientations as described above. Further, the cut outs may be partially or entirely through a thickness of the structure, such as an outer wall structure, as described above.

The rod 700 can be formed by known manufacturing methods, such as additive layer manufacturing, e.g., three-dimensional printing, chemical etching, photo etching, laser cutting, water jet cutting, and traditional machining, etc. Additive layer manufacturing may be performed in any of the ways described above, for example.

The flexible pattern 800 can transition from a less dense, i.e., farther apart, pattern at a first end of the body 714 to a denser, i.e., closer together, pattern at a second end of the body 714. The transition of the flexible pattern 800 along a length of the body 714 can be equivalent from a first end to a second end of the body 714 and vice versa. The transition of the flexible pattern 800 can also be graduated so that there are gradient zones of varying flexibility along a length of the body 714 of the rod 700.

In another aspect, the rod 700 may be used in a method of spinal alignment correction as an element to interconnect bone anchors on adjacent vertebrae. During adjustment of the rod during a procedure, the rod may bend to render adjustment simpler. With the rod, less force is required to adjust the rod relative to a rod without flexible regions.

One advantage of the flexible rod is its versatility during use in surgery. In particular, adjustment of the rod position to accommodate anchor placement is less difficult in view of the flexible regions on the rod.

Corpectomy

In one aspect, the present disclosure is directed an adjustable cage device 900 comprising at least one surface 915 with a flexible pattern 1000, wherein the flexible pattern 1000 includes a continuous line of material. The adjustable cage device 900 can be a foldable cage, such as shown in FIGS. 22A-22C or an expandable cage, such as shown in FIGS. 23A-23D. The flexibility of a surface 915 can be determined by various techniques including determining the stiffness of a surface, i.e., the resistance of a surface to elastic deformation. Stiffness is a measure of the applied force divided by the deflection of the surface. Variables associated with the flexible pattern can alter the stiffness of the surface. By selecting certain variables, a specific stiffness can be achieved in response to a given load. The flexible pattern can provide a stiffness to a surface that can be measured, for example, using a compressive load. The stiffness of a surface including a flexible pattern relative to another surface without the flexible pattern can vary from about 25% to about 100%, for example, from about 35% to about 90%, and as a further example from about 50% to about 80%.

FIGS. 22A-22B illustrate an adjustable cage device 900, such as a foldable cage, comprising at least one surface 915 with a flexible pattern 1000, wherein the flexible pattern 1000 includes a continuous line of material. The adjustable cage 900 device can be a foldable or rollable cage. In an aspect, the adjustable cage device 900 can include at least one endplate 920, for example two endplates.

The at least one endplate 920 can include an exterior surface that can be smooth (not shown) or can include a plurality of projections 922, as shown in FIGS. 22A-C. A smooth surface can be even and regular, i.e., it does not include any projections 922 from the at least one surface. The plurality of projections 922 can be adapted to engage a vertebra or any tissue. The plurality of projections 922 can be arranged in rows and/or columns spreading along the endplate 920. The plurality of projections 922 can inhibit movement of the adjustable cage device 900 when positioned in place.

In an aspect, the adjustable cage device 900 has an endplate 920 including at least one smooth surface. In another aspect, the adjustable cage device 900 has an endplate 920 including at least one smooth surface with a flexible pattern 1000. In another aspect, the adjustable cage device 900 has an endplate 920 including a least one surface with a flexible pattern 1000 and a plurality of projections 922, as shown in FIG. 22D. In another aspect, the adjustable cage device 900 has an endplate 920 including at least one surface with a plurality of projections 922.

The endplate 920 can include an interior surface that includes a channel 930 that extends along an inner edge of the endplate 920. For example, as shown in FIG. 22A, the channel 930 can extend along the circumference of the inner edge. The channel 930 can be configured and dimensioned to receive an edge 935*a*, 935*b* of the at least one surface including a flexible pattern 1000. The edge 935 of the at least one surface including a flexible pattern 1000 can fit within the channel. The flexible pattern 1000 can provide flexibility to the surface so that it bends along the circumference of the endplate 920.

The endplate 920 can vary in dimension. In an aspect, the endplate 920 can be any shape, such as a circle, a square, a triangle, or any other polygon. In another aspect, the endplate 920 can be any size. The adjustable cage device 900 can range from about 10 mm to about 60 mm, for example from about 12 mm to about 20 mm. The adjustable cage device 900 can also be a rectangular size ranging from about 11 mm×11 mm to about 45 mm×50 mm, such as from about 12 mm×14 mm to about 17 mm×20 mm. During an operation, a user can select from various sized endplates 920 and from various surfaces including the flexible pattern 1000 to make a suitable adjustable cage device 900 for the patient.

As shown in FIG. 22B, the adjustable cage device 900 can include an opening 940. The opening 940 can be configured and dimensioned so that a user can insert a bone support matrix into the adjustable cage device 900. As used herein, a "bone support matrix" is a material that facilitates osteogenesis. Suitable bone support matrices can be resorbable or nonresorbable and osteoconductive or osteoinductive. Non-limiting examples of suitable bone support matrices include synthetic materials, bone morphogenic proteins (BMPs), and heterologous, homologous, or autologous bone and derivatives thereof. The bone support matrix may be radiolucent on x-rays.

Figure 23A:
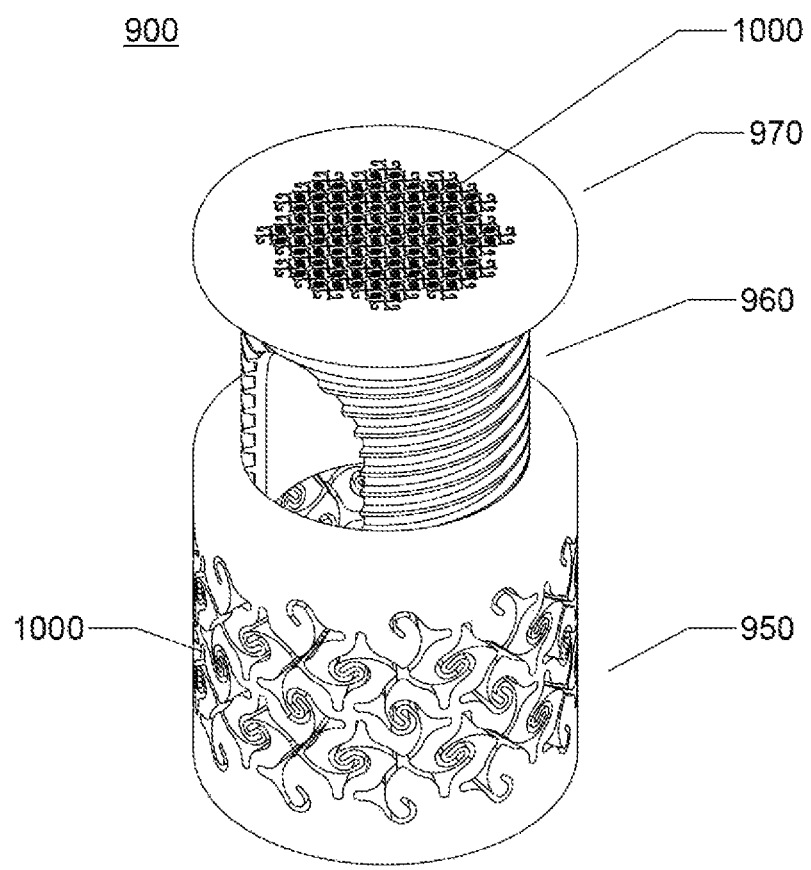
FIG. 23A is an isometric view of an adjustable cage according to one embodiment of the disclosure.
Figure 23B:
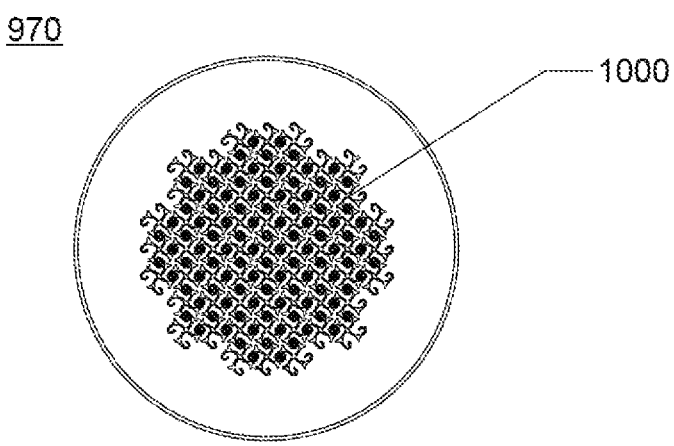
FIG. 23B is a top view of the adjustable cage of FIG. 23A.

FIGS. 23A-23D illustrate an adjustable cage device 900 according to another aspect of the disclosure. The adjustable cage device cage 900 can be a corpectomy cage and can be designed for supporting adjacent vertebra. A user may, in real time, independently adjust the height of the adjustable cage device 900. During operation, the user can adjust the height of the adjustable cage device 900 by moving a housing 950 relative to a support member 960 to accommodate adjustable cage device 900 in a variable space located between adjacent vertebrae. After placing adjustable cage device 900 in such a space, a top surface 970 with a flexible pattern 1000 (as shown in FIGS. 23A-23B) and/or a housing 950 with a flexible pattern 1000 can flex to mimic or closely match the surface of the adjacent vertebrae. As will be appreciated by one of ordinary skill in the art the ability to mimic or closely match the surface of the adjacent vertebra can improve the stability of the spine by providing a better fit between adjacent vertebrae and thereby improve osteogenesis.

Figure 23C:
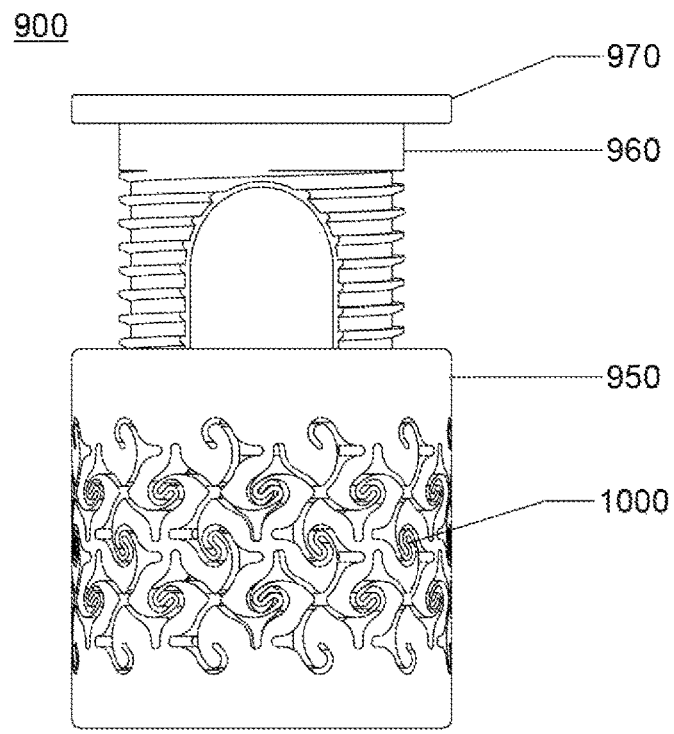
FIGS. 23C-D are side views of the adjustable cage of FIG. 23A.
Figure 23D:
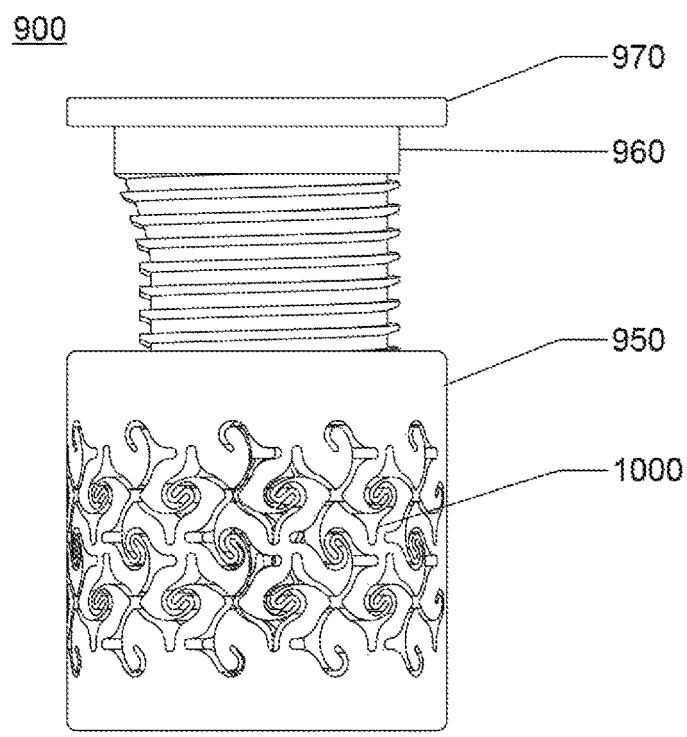

As shown in FIGS. 23A, 23C, and 23D, the adjustable cage device 900 can include a housing 950, a support member 960, and a top surface 970, wherein at least one of the housing 950 and the top surface 970 can include a flexible pattern 1000. In aspect, one of ordinary skill in the art could include additional support members (not shown) to the adjustable cage device 900, wherein the additional support members could be used to further increase the height of the adjustable cage device 900 and/or provide angled top surfaces 970 (not shown) in multiple planes.

In an aspect, an initial height of the adjustable cage device 900 can range from about 12 mm to about 130 mm. One of ordinary skill in the art will appreciate that the initial height of an adjustable cage device 900 can be based in part upon the initial footprint of the adjustable cage device 900. For example, an adjustable cage device 900 with a smaller footprint will likely have a smaller initial height. The initial height of the adjustable cage device 900 can be increased by, for example, an additional 4 mm. One of ordinary skill in the art will understand that the height of the adjustable cage device 900 can be increased in any increment from 0 mm and 16 mm, such as for example from about 0.5 mm to about 15.5 mm, from about 1.0 mm to about 14.0 mm, and as another example from about 2.0 mm to about 13.0 mm.

In an aspect, an angle of the top surface 970 of the adjustable cage device 900 can also be adjusted. In an aspect, an initial angle of the top surface 970 of the adjustable cage device 900 can be 0° with respect to an x-axis, as shown in FIGS. 23A-23D. However, this angle can be adjusted to better align the endplate 940 with an adjacent vertebra to more accurately align the adjustable cage device 900 with the adjacent vertebra. In an aspect, the angle can be adjusted to any increment from 0° to about 45°, including any angle in between, such as 15°, 20°, and 30°. One of ordinary skill in the art would be able to adjust the angle of the top surface 970.

The adjustable cage device 900 can be filled with a bone support matrix.

The housing 950 can include an elongate body and defining a longitudinal passage (not shown). The longitudinal passage can be dimensioned and configured to receive at least a portion of the support member 960. For example, a wall of the longitudinal passage can include a helical thread dimensioned and configured to engage with an external helical thread present on the support member 960.

The adjustable cage device 900 can include at least one surface that can include a flexible pattern 1000, wherein the flexible pattern 1000 includes a continuous line of material. As shown in FIGS. 22A and 22B, the at least one surface 915 can include the flexible pattern 1000. Additionally, FIG. 22C illustrates an endplate 920 of the adjustable cage device 900 having a surface including a flexible pattern 1000. FIGS. 23A-23D illustrate an adjustable cage device 900 with a housing 950 and a top surface 970, each independently, with a flexible pattern 1000.

The flexible pattern 1000 can be present on an entire surface, as shown in FIG. 22A. In another aspect, the flexible pattern 200 can be present on a portion of the surface, as shown in FIGS. 22C, and 23A-23D. For example, the flexible pattern 1000 can be present in vertical strips with a non-flexible surface in between the strips; horizontal strips with a non-flexible surface in between the strips; an inner area with a perimeter of non-flexible surface (for example, as shown in the top surface 970 of FIG. 23B); and a perimeter with an inner area of a non-flexible surface. Any and all variations of the flexible pattern 1000 on a surface are contemplated.

The flexible pattern of material on the adjustable cage device may be varied in many ways, such as those shown in FIGS. 2A, 2B, 3A, 3B, 4A, and 4B. In these variations, the flexible pattern of adjustable cage device 900 shown in FIGS. 22A-C and 23A-D may be substituted with flexible pattern 200 shown in any one of FIGS. 2A, 2B, 3A, 3B, 4A and 4B. As shown in FIGS. 2A, 2B, 3A, 3B, 4A, and 4B, the flexible pattern 200 can include a continuous line of material. As shown in FIGS. 2A, 2B, 3A, 3B, 4A, and 4B, the shaded area is the continuous line of material forming the flexible pattern 200. The white area is the absence of material. The flexible pattern 200 can include a plurality of segments 202 that interconnect to form rows and columns. A segment 202 can include a first end and a second end in which the first end of each segment 200 can interconnect with at least one second end of another segment of the plurality of segments, for example in an adjacent row or column. In an aspect, a first end of a segment 202 can interconnect with three different segments to form the flexible pattern 200 with a continuous line of material. In a further aspect, a second end of a segment 202 can interconnect with three different segments to form the flexible pattern 200 with a continuous line of material.

In another aspect as shown in FIG. 5A, the segment 202 can flip orientations within the continuous line of material so that in a first configuration the segment forms rows and in an adjacent second configuration the segment forms columns. The flexible pattern can also increase in size. For example, as shown in FIG. 5A, the innermost columns and rows are smaller in size than the outermost columns and rows. Accordingly, the stiffness in the interior of the flexible pattern 200 is expected to be lower than a stiffness along the outer edges, e.g., perimeter, of the flexible pattern 200.

In another aspect as shown in FIG. 5C, the flexible pattern 200 may include a plurality of segments 202 that interconnect to mimic a pattern of cortical bone. The segments 202 switch back and forth in an arching pattern and/or curlicue pattern. The stiffness in the interior of the flexible pattern 200 is expected to be higher than a stiffness along the outer edges, e.g., perimeter, of the flexible pattern 200. The flexible pattern 200 illustrated in FIG. 5C can be a single continuous radius across an entire or a portion of a surface. In another aspect, the flexible pattern 200 illustrated in FIG. 5C can be multiple separate spheres across an entire or a portion of a surface.

As shown in FIGS. 2A, 2B, and 5A, the flexible pattern 200 can include a continuous line of material that forms corners, which can be used to form smaller or denser patterns. A flexible pattern 200 with corners can be harder to manufacture. As shown in FIGS. 3A, 3B, 4A, 4B, and 5C, the flexible pattern 200 can comprise curves, arches, and/or curlicues, which can be used to form larger or less dense patterns. A flexible pattern 200 with curves, arches, and/or curlicues can be easier to manufacture.

The continuous line of material can be any biocompatible material, such as a metal, an alloy, a polymer, and combinations thereof, such as a blend of a metal and a polymer. For example, the continuous line of material may be made of polyetheretherketone (PEEK), titanium, stainless steel, cobalt chrome, polymeric materials, a combination thereof, or any other suitable material. The continuous line of material can have a uniform width. In an aspect, a width of the continuous line of material can vary. In an aspect, the continuous line of material can include straight areas and/or curved areas.

In further variations, the flexible pattern may also be as shown in FIGS. 6-10 and described above. The material cut outs of the flexible pattern may all be perpendicular to a surface with the flexible pattern, some may be at an acute angle relative to the surface, or the cut outs may be any combination of orientations as described above. Further, the cut outs may be partially or entirely through a thickness of the structure, such as an outer wall structure, as described above.

The at least one surface including a flexible pattern 1000 can be formed by known manufacturing methods, such as additive layer manufacturing, e.g., three-dimensional printing, chemical etching, photo etching, laser cutting, water jet cutting, and traditional machining, etc. Additive layer manufacturing may be performed in any of the ways described above, for example.

The flexible pattern 1000 can flex under application of a force. In an aspect, a first area of the flexible pattern 1000 can move in a direction relative to a second area of the flexible pattern 1000 under an applied force.

Each surface of the adjustable cage device 900 can be independent from any other surface of the adjustable cage device 900 in terms of variables, such as degree of flexibility, degree of rigidity, density of the flexible pattern 1000, form of the flexible pattern 1000, thickness of the surface including the flexible pattern 1000, and etc. One of these variables may impact another variable. For example, a thick housing 950 with a flexible pattern 1000 can have a higher degree of rigidity as compared to a thin top plate 970 with a flexible pattern 1000 within the same adjustable cage device 900.

In FIGS. 16A-C and 17A-C, like reference numerals in the 100 and 200 series refer to like elements in the 900 and 1000 series of numerals, respectively, and 162 refers to a surface. FIGS. 16A-C illustrate the side view of, for example, a surface 162 having a flexible pattern 200, as shown in FIGS. 17A-C, respectively. FIG. 16A illustrates a surface 162 that is thicker than a surface as shown in FIG. 16B, which is thicker than a surface as shown in FIG. 16C. FIGS. 16A-C and FIGS. 17A-C illustrate that a thin surface with a flexible pattern 200 (see, e.g., FIGS. 16C and 17C) can have a greater degree of flexibility as compared to a thicker surface with a flexible pattern 200 (see, e.g., FIGS. 16A and 17A).

As another example, of how one variable of the flexible pattern 1000 can effect another variable of the flexible pattern 1000, a housing 950, as shown in FIGS. 23A-23B, can have a dense flexible pattern 200 including a curved line as shown in FIG. 3B, and a top surface 970 can have a less dense flexible pattern 200 comprising squared lines as shown in FIG. 2B. It is appreciated that each surface with a flexible pattern 1000 of an adjustable cage device 900 can be designed to meet the requirements for its particular use.

As shown in FIGS. 12A-12D, the flexible pattern 200, in place of flexible pattern 1000, can be the same or different and/or can be present or absent across the at least one surface of the interbody 100. In an aspect, the flexible pattern 200 can be present across the entire surface, as shown in FIG. 12A, or can be present in sections (i.e., can be absent in sections) of the at least surface, such as shown in FIGS. 12B-12D. In another aspect, the flexible pattern 200 can be present in a section to form a perimeter 206 of the at least one surface without being present at an interior of the at least one surface, as shown FIG. 12C. The flexible pattern 200 can also be present in an interior 208, without extending to one or more edges, to form a center of the at least one surface, as shown in FIGS. 12B and 12D.

The flexible pattern 200 can transition from a perimeter to an interior so that the perimeter is more flexible than the interior and vice versa. For example, the flexible pattern 200 can transition from a less dense, i.e., farther apart, pattern at a perimeter to a denser, i.e., closer together, pattern at an interior of the at least one surface. As a further example, the flexible pattern 200 can transition from a denser, i.e., closer together, pattern at a perimeter to a less dense, i.e., farther apart, pattern at an interior of the at least one surface. The transition of the flexible pattern 200 can be equivalent from a perimeter to an interior and vice versa. The transition of the flexible pattern 200 can be graduated so that there are gradient zones of varying flexibility across the at least one surface.

The at least one surface can include alternating sections. For example, a first section of the at least one surface can be more rigid. A second section can be adjacent to the first section and can be more flexible. The number of alternating rigid and flexible sections can vary. The at least one surface can be more rigid depending upon variables, such as the density of the pattern and/or the thickness of the material used to form the pattern. Similarly, the at least one surface can be more flexible with, for example, a less dense pattern and/or a thinner material used to form the pattern. In another aspect, the at least one surface can include an alternating section of a first section with a flexible pattern 200 and a second section without a flexible pattern 200.

The at least one surface can have a uniform thickness. In another aspect, the at least one surface can have a thickness that varies. The thickness can vary by sections. For example, the at least one surface can have a first section that is thin adjacent to a second section that is thick (compared to the first section). The thin/thick sections can alternate across the at least one surface and can affect the flexibility of the at least one surface. In another aspect, the thickness can vary along a gradient of the at least one surface, such as from thick to thin or vice versa. It is expected that a section of the at least one surface that is thicker than another section will also be more rigid. Similarly, it is expected that a section of the at least one surface that is thinner than another section will also be more flexible, as shown in FIGS. 16A-C and FIGS. 17A-C.

In another aspect, the adjustable cage device 900 is used in a method of performing a corpectomy.

The adjustable cage device 900 is advantageous in that the flexible regions on the device are adaptable to natural and varying curvature and dimensions of a spine of a patient. For example, upper and lower surfaces of the device adapt to conform to a bone surface of a vertebra opposite a device surface when the device is positioned within the spine. This reduces or eliminates problems associated with gaps between a cage device and adjacent vertebral bodies.

Other Implant Structures

Figure 24:
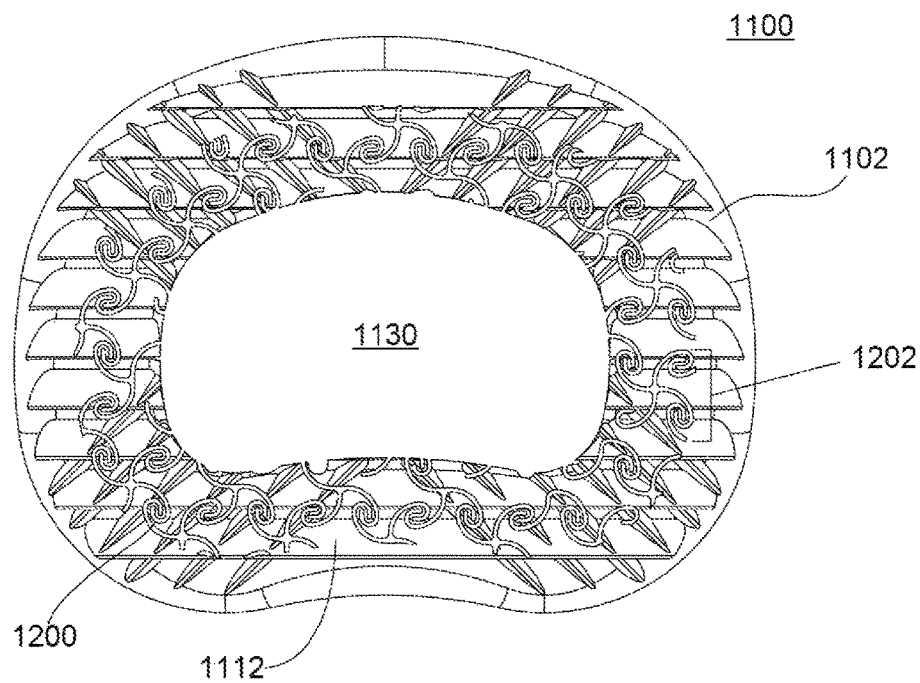
FIGS. 24-26 are perspective views of an interbody implant according to one embodiment of the disclosure.
Figure 25:
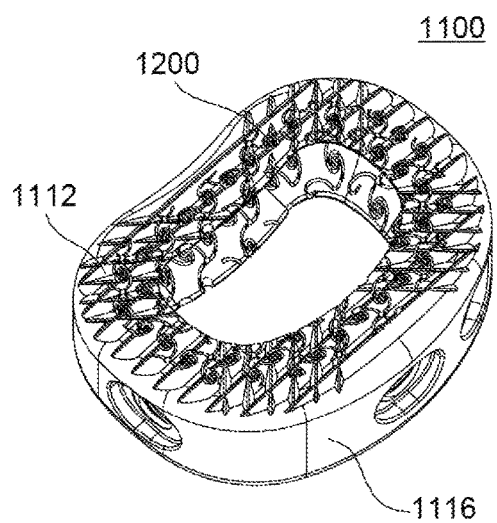
Figure 26:
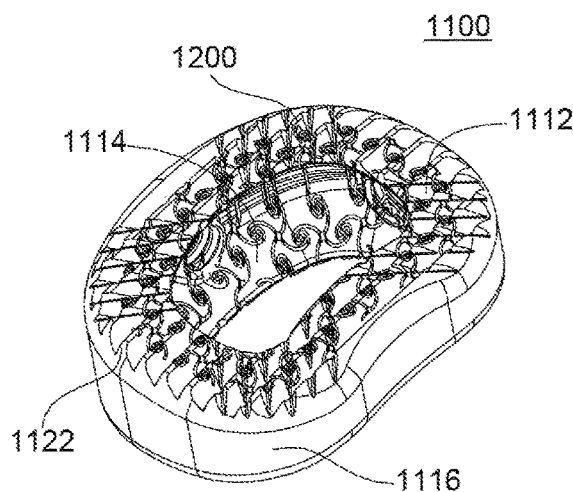

In one aspect, the present disclosure relates to a flexible interbody 1100 as shown in FIGS. 24-26. Interbody 110 includes a ring shaped body 1102 surrounding an opening 1130. An inner side surface 1114 defines a boundary of opening 1130 while outer side surface 1116 defines an outer perimeter of body 1102. Top surface 1112 and an opposite bottom surface (not shown) are symmetrical about a plane passing centrally therebetween and perpendicular to outer side surface 1116. Both top surface 1112 include protrusions 1122 thereon in the form of teeth angled in a single direction. An inner portion of top surface 1112 remote from outer side surface 1116 and abutting inner side surface 1114 includes a flexible pattern 1200. As shown, flexible pattern 1200 is the same as that shown in FIGS. 3A and 3B. A segment 1202 is illustrative of the aforementioned pattern. Flexible pattern 1200 extends from top surface throughout inner side surface 1114, as shown in FIG. 26, and through a portion of the bottom surface in a manner similar to top surface 1112. The performance of implant 1100 with flexible pattern 1200 may be as described above for flexible pattern 200. In variants, pattern 1200 shown may be substituted with another pattern such as that shown in FIGS. 1C, 2A, 2B, 4A-4B, 5A-5D and 6-10.

Figure 27:
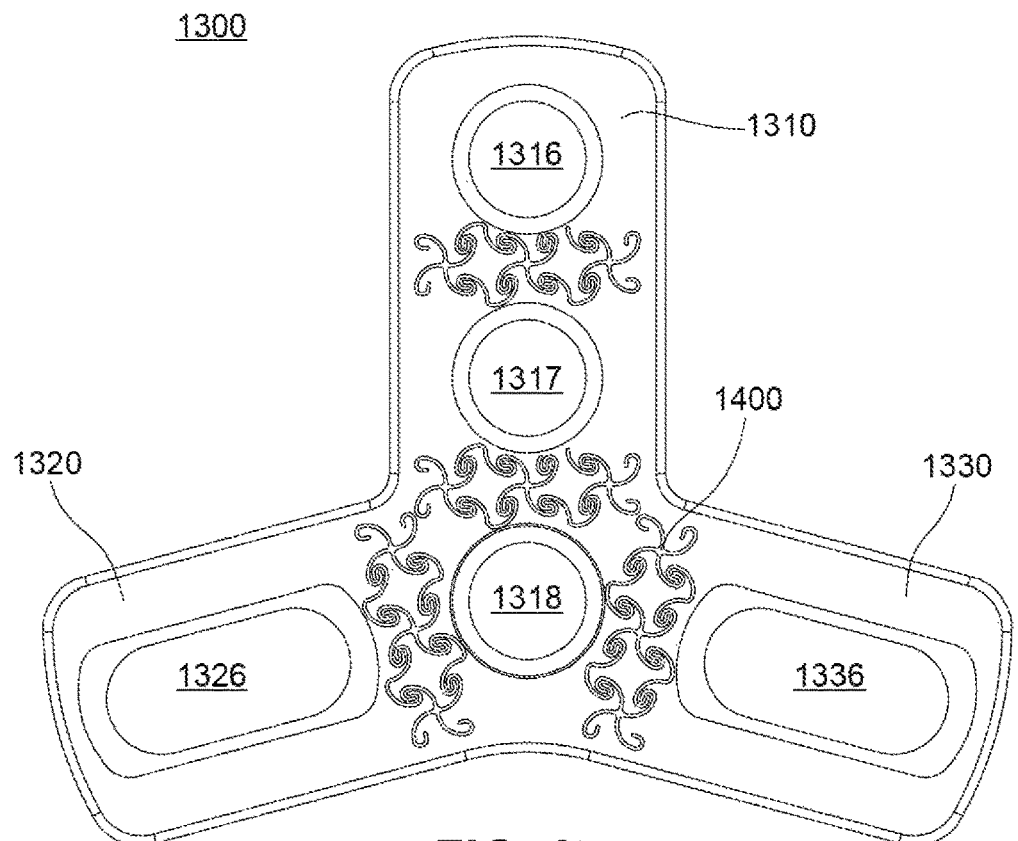
FIGS. 27-28 are top and perspective views of a plate according to one embodiment of the disclosure.
Figure 28:
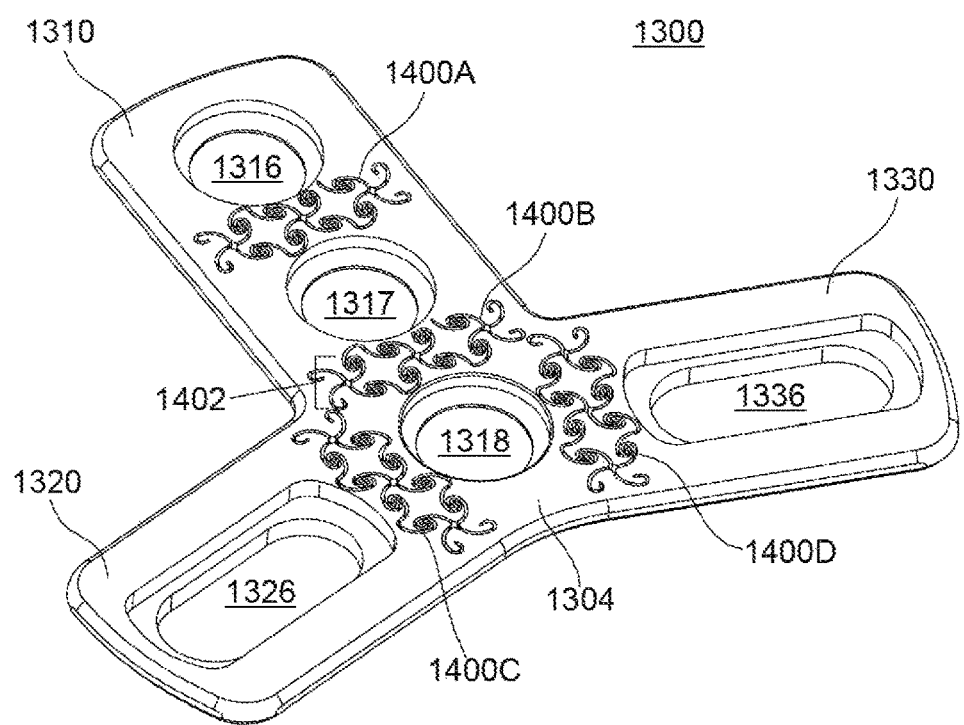

In another aspect, the present disclosure relates to a plate 1300 as illustrated in FIGS. 27 and 28. Plate 1300 is symmetrical about one axis and includes a body 1302 with a first portion 1310, a second portion 1320 and a third portion 1330, each extending in a linear manner from a central area 1304 surrounding an opening 1318. First portion 1310 includes three openings 1316, 1317, 1318, each having a countersink. Second and third portions 1320, 1330 each include a slot 1326, 1336, respectively, therein. Each slot includes a counterbore as shown. Flexible pattern 1400A-D is located over various areas on plate 1300 between openings, slots or openings and slots. In particular, flexible pattern 1400A is located between openings 1316 and 1317 and flexible pattern 1400B is located between openings 1317 and 1318. Similarly, flexible patterns 1400C and 1400D are located between opening 1318 and slots 1326 and 1336, respectively. In this manner, flexible pattern 1400B-D surrounds opening 1318 on three sides in central area 1304. Here, a segment 1402 illustrates that flexible pattern 1400 is the same as that shown in FIGS. 3A-B. In variants, the flexible pattern may be may be substituted with another pattern such as that shown in FIGS. 1C, 2A, 2B, 4A-4B, 5A-5D and 6-10. Through the inclusion of flexible regions, the plate is more versatile in its application on a target anatomical surface. For example, it may deform to match contours of a surface thereby minimizing gaps between the plate and the surface to which it is applied.

Figure 29:
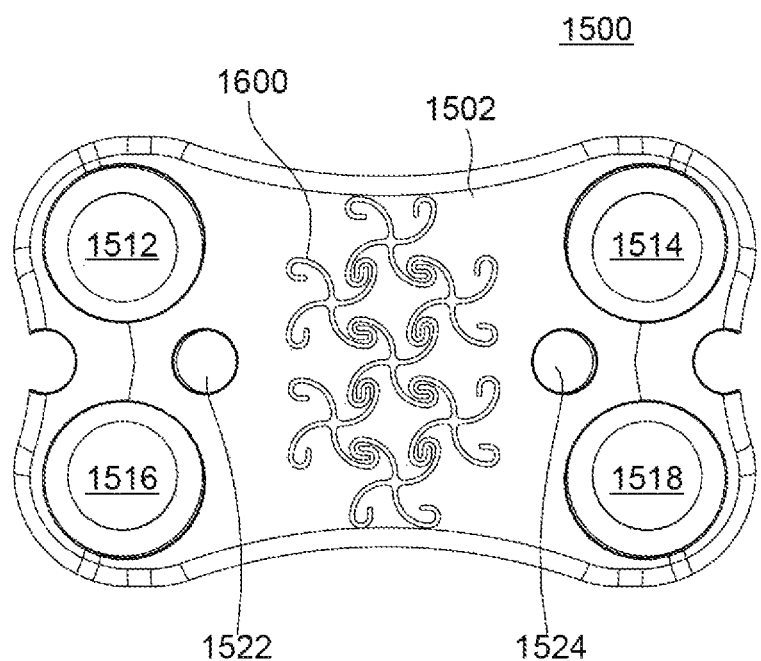
FIGS. 29-30 are top and perspective views of a plate according to one embodiment of the disclosure.
Figure 30:
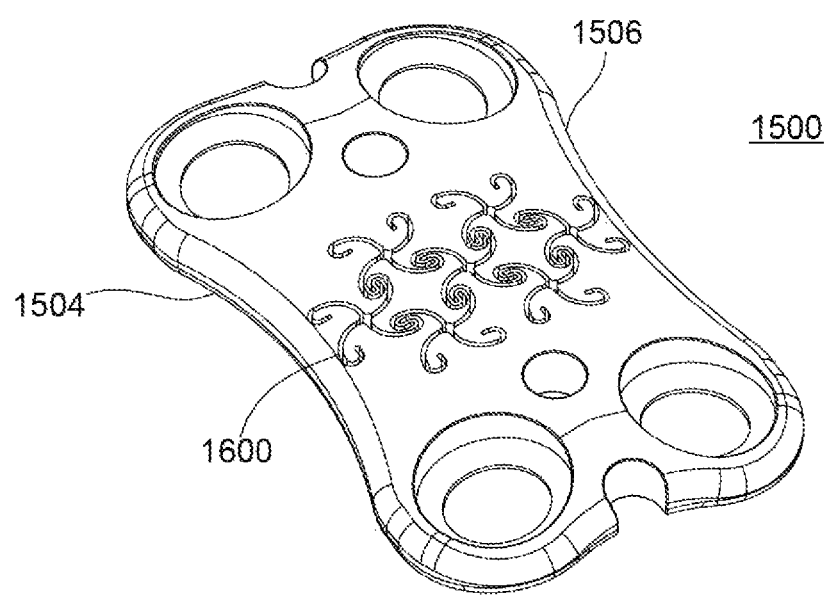

In yet another aspect, the present disclosure relates to a plate 1500 shown in FIGS. 29 and 30. Plate 1500 includes body 1502 with peripheral openings 1512, 1514, 1516, 1518 located at respective corners of the plate and additional openings 1522, 1524 located slightly interior and central to opening pairs 1512, 1516 and 1514, 1518, respectively. In a central region of plate 1500 is flexible pattern 1600, the pattern also shown in FIGS. 3A-B. In variants, the flexible pattern may be may be substituted with another pattern such as that shown in FIGS. 1C, 2A, 2B, 4A-4B, 5A-5D and 6-10.

Figure 31:
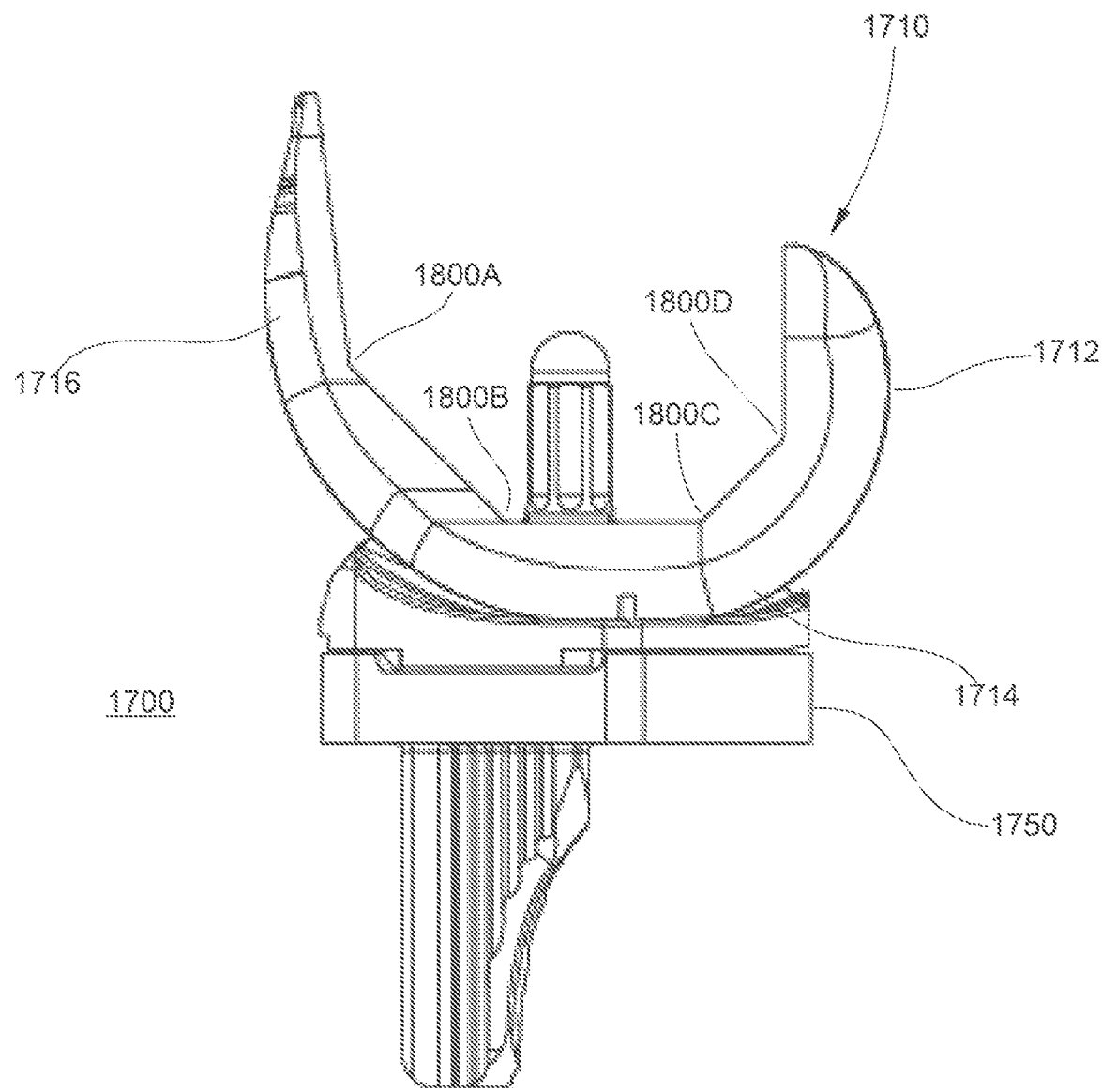
FIG. 31 is a side view of a femoral implant included as part of a knee implant system according to one embodiment of the disclosure.

In another aspect, the present disclosure relates to a knee implant system 1700 that includes a femoral component 1710 and a tibial component 1750. Femoral component 1710 includes a condyle portion 1712, a contact portion 1714 and an anterior portion 1716. In this arrangement, each angulation on an interior surface of femoral component 1710 includes a surface with a flexible pattern thereon. Specifically, and as shown in FIG. 31, flexible pattern 1800A-D is formed at respective angulations on the interior surface of femoral component 1710. The inclusion of flexible pattern 1800A-D in the manner described is advantageous in that the femoral component may change shape during implantation to accommodate any irregularities in the surface of the resected femur to which the implant is to be attached. This in turn reduces or otherwise eliminates the need to perform resurfacing prior to final positioning of the implant. The flexible pattern on the implant may be one or more of those shown in FIGS. 1C, 2A, 2B, 3A-B, 4A-4B, 5A-5D and 6-10, for example.

As with other aspects of the disclosure described above, the cut outs of the flexible pattern of each implant may all be perpendicular to a surface with the flexible pattern, some may be at an acute angle relative to the surface, or the cut outs may be any combination of orientations as described above. Further, the cut outs may be partially or entirely through a thickness of the structure, such as an outer wall structure, as described above. Further, the implants may be formed by known manufacturing methods, such as additive layer manufacturing, e.g., three-dimensional printing, chemical etching, photo etching, laser cutting, water jet cutting, and traditional machining, etc. Additive layer manufacturing may be performed in any of the ways described above, for example.

In another aspect, the present disclosure relates to an interbody implant 1900 shown in FIGS. 32-35. Interbody 1900 includes body 1902 with a first surface 1916, second surface 1918, top surface 1912 and bottom surface 1914. Extending through interbody 1900 at angles with respect to each other are openings 1922, 1924. Each opening 1922, 1924 defines an axial path for a fastener or other anchoring element. To form a complete enclosure around each opening while also preserving a full diameter pathway through the interbody, each opening is partially defined by an opening enclosure element in the shape of an arch and much narrower than the remainder of body 1902. In particular, opening 1922 is partially defined by first opening enclosure 1913 while opening 1924 is partially defined by second opening enclosure 1915.

Figure 32:
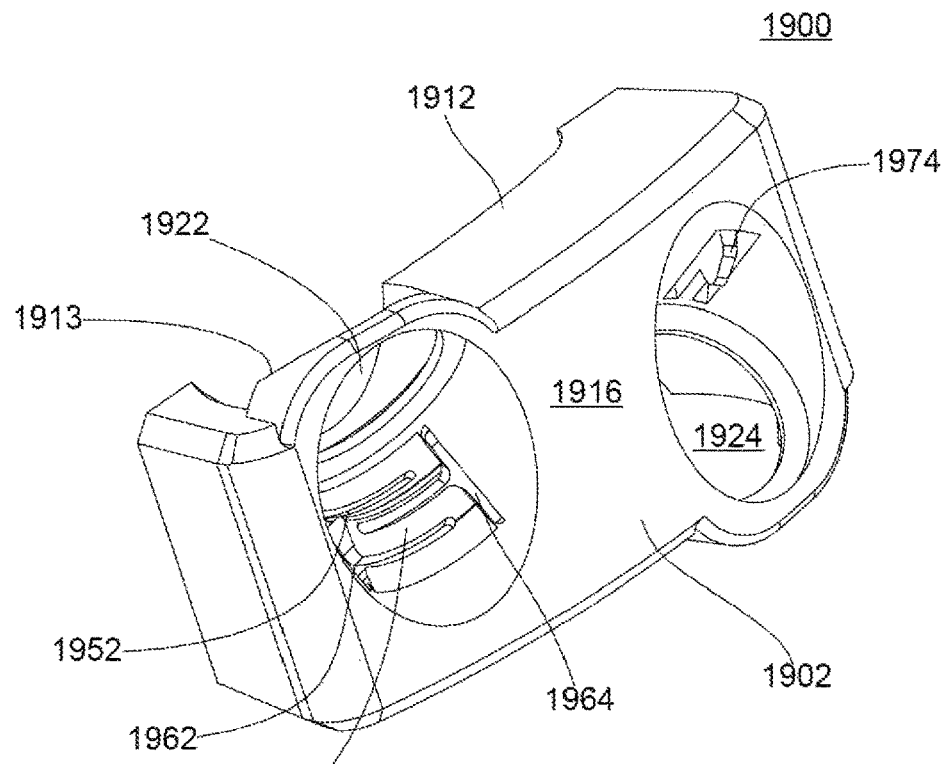
FIGS. 32-35 are various views of an interbody implant according to one embodiment of the disclosure.
Figure 33:
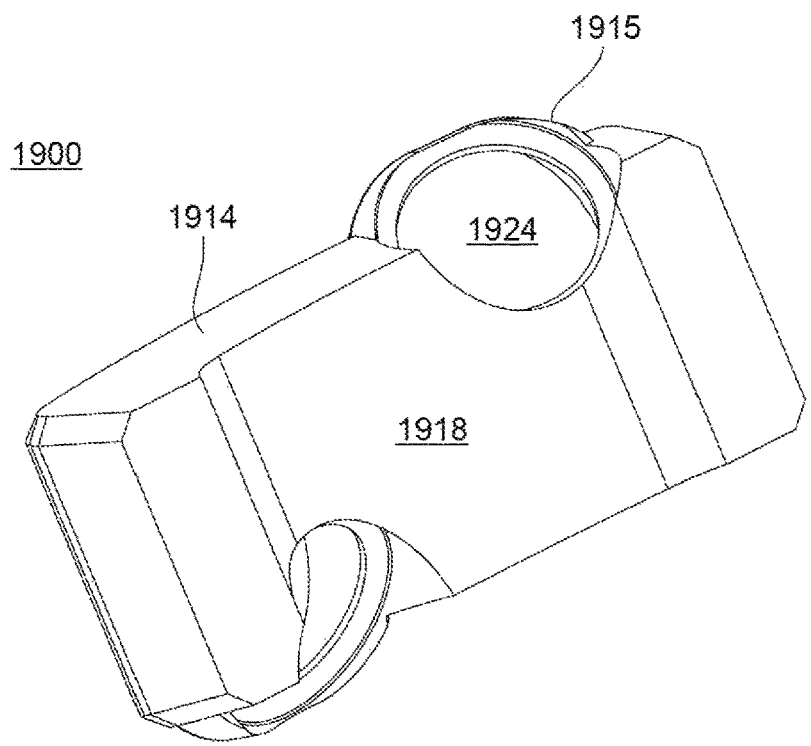
Figure 34:
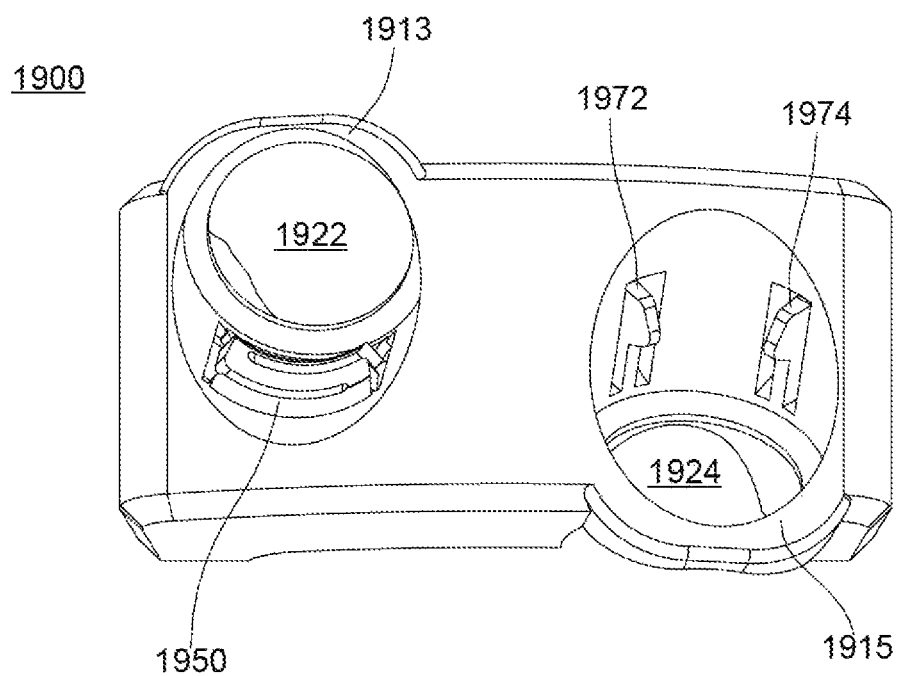
Figure 35:
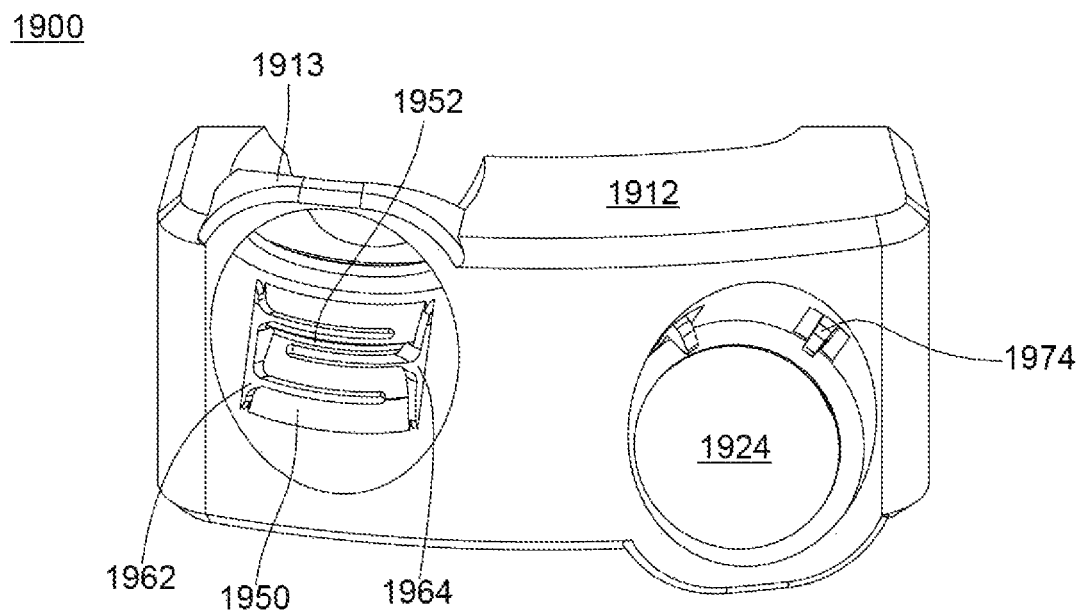

Each opening includes unique flexible features to allow engagement with an element inserted therein. Within opening 1922 is a continuous strip of material 1950 over a portion of opening perimeter, as shown in FIGS. 32, 34 and 35. Two separate gaps 1962, 1964 define a shape of continuous strip 1950, while a portion of continuous strip 1950 protrudes 1952 relative to the rest. As shown in the depicted embodiment, gap 1962 is C-shaped and gap 1964 is T shaped. In alternative arrangements, the geometry of gaps 1962, 1964 may vary from that shown. Gaps 1962, 1964 may be between 0.003 to 0.200 inches in width. In one preferred arrangement, gaps 1962, 1964 are between 0.006 and 0.080 inches in width. When an object is placed through opening 1922, strip 1950, having elastic properties, deforms to allow the object to pass and then returns to its original shape upon passage of the object. In this manner, the object may be secured in place within the opening. Turning to opening 1924, a surface defining such opening includes a pair of hooks 1972, 1974, best shown in FIG. 34. Each hook is freestanding within an opening in an inner surface defining opening 1924 and includes an end tip in the form of a hook that extends inward into opening 1924. In this manner, the tips of each hook 1972, 1974 protrude relative to the cylindrical surface that defines opening 1924. Each hook 1972, 1974 has a degree of flexibility permitting bending during insertion of an object therethrough so that upon passage of the object, the applicable hook returns to its undeformed shape, thereby providing a secure connection between the interbody and the inserted object. Interbody implant 1900 may be attached to or formed with a plate (not shown) or another standalone device. Thus, in one non-limiting example, fasteners may be used to secure an interbody 1900 that includes a plate to a bone. Specifically, fasteners may be inserted through the openings in the interbody and into the bone, locking to both the interbody and the bone in the process. Because the plate is part of the interbody, the plate is also locked in place.

In any one of the above embodiments, a single structure with flexible surface regions may have two or more types of flexible patterns. Any combination of patterns described or otherwise contemplated herein may be included in these combinations.

In another aspect, the present disclosure relates to a flexible surface that includes a flexible pattern. The material of the surface may be any contemplated for use in a surgical procedure. In one embodiment, the flexible pattern is as shown in FIGS. 2A-2B and described above. In other embodiments, the flexible pattern is one of the patterns shown in FIGS. 3A-3B, 4A-4B, 5A-5B, 5C-5D and 6-10 and described above. The flexible surface may also include other patterns as contemplated by the present disclosure. In other embodiments, the flexible pattern may include any combination of the aforementioned patterns.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An intervertebral implant comprising:
an upper endplate, a lower endplate opposite the upper endplate and an intermediate support connecting the upper endplate and the lower endplate, the upper endplate and the lower endplate defining a void therebetween, wherein the upper and lower endplates are both adapted to contact a vertebral body of a spine; and
a first portion on one of the upper endplate and the lower endplate, the first portion including a first flexible surface with a plurality of segments that define a plurality of slits, the plurality of slits including a first slit and a second slit, the first slit crossing the second slit between first and second ends of the second slit,
wherein the first portion inclusive of each of the plurality of segments is monolithic, and
wherein the first flexible surface has a surface contour that changes as a function of force borne by the first flexible surface such that when the intervertebral implant is disposed between vertebral bodies, the first flexible surface deforms to adapt to the contours of a bone surface bearing thereon.

2. The intervertebral implant of claim 1, wherein the first flexible surface is flexible in a direction transverse to a plane that is approximately aligned with the first flexible surface.

3. The intervertebral implant of claim 1, wherein the first slit has a length extending from a first enclosed end to a second enclosed end opposite the first enclosed end.

4. The intervertebral implant of claim 1, wherein the plurality of segments include a first segment, a second segment, a third segment and a fourth segment, each segment extending radially from a first location and each segment being oriented differently relative to the first location than the other segments.

5. The intervertebral implant of claim 4, wherein the plurality of segments are positioned such that a first axis passing through a first midpoint of a first length of the first segment and a second midpoint of a second length of the second segment is orthogonal to a second axis passing through the first midpoint of the first segment and a third midpoint of a third length of the third segment.

6. The intervertebral implant of claim 1, wherein the plurality of segments interconnect to form rows and columns.

7. The intervertebral implant of claim 4, wherein each of the first, second, third and fourth segments have the same shape.

8. The intervertebral implant of claim 1, further comprising a second flexible surface with a second plurality of slits, the second flexible surface being different from the first flexible surface.

9. The intervertebral implant of claim 4, wherein the first segment includes a first portion, a second portion and a third portion, the first portion being linear and oriented in a first direction, the second portion being linear and oriented in a second direction different from the first direction, and the third portion being linear and oriented in a third direction different from the second direction.

10. The intervertebral implant of claim 1, further comprising at least one non-flexible surface.

11. The intervertebral implant of claim 1, wherein each of the plurality of slits extend entirely through the one of the upper endplate and the lower endplate of the intervertebral implant.

12. The intervertebral implant of claim 11, wherein the plurality of slits include at least two slits that are oriented at different angles relative to the first flexible surface.

13. A method of using an intervertebral implant comprising:
   providing the intervertebral implant, the intervertebral implant including a first endplate having a flexible surface, the flexible surface including a first slit with a first length extending between a first enclosed end and a second enclosed end and a second slit with a second length extending between a third enclosed end and a fourth enclosed end, the second slit intersecting the first slit between the first and second enclosed ends, wherein the flexible surface is a monolithic surface;

inserting the intervertebral implant into a final operative location within a patient such that the first endplate abuts a first vertebral body and a second endplate of the intervertebral implant abuts a second vertebral body, and deforming the first endplate of the intervertebral implant based on force applied to the flexible surface by the first vertebral body, the force causing a uniform surface contour of the flexible surface to become a non-uniform surface contour, wherein before, during and after the deformation, the first, second, third and fourth enclosed ends remain enclosed such that each enclosed end remains a terminal end of a respective slit in the flexible surface.

14. The method of claim 13, wherein deforming the endplate of the intervertebral implant occurs while the intervertebral implant is being disposed in the final operative location, the flexible surface conforming to a shape of a surface that applies force to the flexible surface.

15. The method of claim 13, wherein deforming occurs only in the flexible surface and a peripheral surface of the first endplate retains its shape before and after being subject to force.

16. The method of claim 13, wherein providing the intervertebral implant includes providing the first endplate such that the first endplate including an entirety of the flexible surface is monolithic.

\* \* \* \* \*